(12) United States Patent
Reshetnyak et al.

(10) Patent No.: US 11,274,126 B2
(45) Date of Patent: Mar. 15, 2022

(54) PH-SENSITIVE CYCLIC PEPTIDES

(71) Applicant: University of Rhode Island Board of Trustees, Kingston, RI (US)

(72) Inventors: Yana K. Reshetnyak, South Kingstown, RI (US); Oleg A. Andreev, South Kingstown, RI (US); Keykavous Parang, Irvine, CA (US)

(73) Assignee: University of Rhode Island Board of Trustees, Kingston, RI (US)

( * ) Notice: Subject to any disclaimer, the term of this patent is extended or adjusted under 35 U.S.C. 154(b) by 128 days.

(21) Appl. No.: 16/087,628

(22) PCT Filed: Mar. 21, 2017

(86) PCT No.: PCT/US2017/023458
§ 371 (c)(1),
(2) Date: Sep. 21, 2018

(87) PCT Pub. No.: WO2017/165452
PCT Pub. Date: Sep. 28, 2017

(65) Prior Publication Data
US 2019/0382448 A1    Dec. 19, 2019

Related U.S. Application Data

(60) Provisional application No. 62/311,156, filed on Mar. 21, 2016.

(51) Int. Cl.
*A61K 38/12* (2006.01)
*C07K 7/64* (2006.01)
(Continued)

(52) U.S. Cl.
CPC .................. *C07K 7/64* (2013.01); *A61K 8/44* (2013.01); *A61K 8/64* (2013.01); *A61K 45/06* (2013.01);
(Continued)

(58) Field of Classification Search
None
See application file for complete search history.

(56) References Cited

U.S. PATENT DOCUMENTS 6,492,326 B1  12/2002  Robinson et al.
6,620,419 B1   9/2003  Lintner
(Continued)

FOREIGN PATENT DOCUMENTS

WO    WO 2015/067712    *  11/2014   ............. A61K 38/17
WO    2015/161820 A1       10/2015
WO    2017/165452 A1        9/2017

OTHER PUBLICATIONS

Andreu D., et al. (1994) Formation of Disulfide Bonds in Synthetic Peptides and Proteins. In: Pennington M.W., Dunn B.M. (eds.) Peptide Synthesis Protocols. Methods in Molecular Biology, vol. 35. pp. 91-169; Humana Press, Totowa, NJ.*
(Continued)

*Primary Examiner* — Kevin S Orwig
(74) *Attorney, Agent, or Firm* — Mintz Levin Cohn Ferris Glovsky and Popeo, P.C.; Ingrid A. Beattie

(57) ABSTRACT

The present subject matter provides pH triggered peptides, as well as compositions methods, devices, and systems comprising the same. The pH triggered peptides include cyclic and short linear peptides, and may have higher affinity to a membrane lipid bilayer at low pH than at neutral or high pH.

27 Claims, 20 Drawing Sheets
Specification includes a Sequence Listing.

(51) Int. Cl.
| | |
|---|---|
| A61K 8/44 | (2006.01) |
| A61K 8/64 | (2006.01) |
| A61K 45/06 | (2006.01) |
| A61K 49/00 | (2006.01) |
| A61Q 17/00 | (2006.01) |
| A61Q 19/08 | (2006.01) |
| C07K 7/08 | (2006.01) |
| A61K 38/00 | (2006.01) |

(52) U.S. Cl.
CPC ...... *A61K 49/0043* (2013.01); *A61K 49/0056* (2013.01); *A61Q 17/005* (2013.01); *A61Q 19/08* (2013.01); *C07K 7/08* (2013.01); *A61K 38/00* (2013.01)

(56) References Cited

U.S. PATENT DOCUMENTS

| | | |
|---|---|---|
| 8,025,907 B2 | 9/2011 | Belfer |
| 2005/0118277 A1 | 6/2005 | Wormser |
| 2005/0282755 A1 | 12/2005 | Hart et al. |
| 2006/0147371 A1 | 7/2006 | Tuszynski et al. |
| 2007/0048236 A1 | 3/2007 | Huang et al. |
| 2007/0148222 A1 | 6/2007 | Dorogi et al. |
| 2008/0152606 A1 | 6/2008 | Reinhart et al. |
| 2009/0005292 A1 | 1/2009 | Holmes et al. |
| 2009/0298707 A1 | 12/2009 | Yarbrough et al. |
| 2013/0064895 A1 | 3/2013 | Dittrich |
| 2013/0172272 A1* | 7/2013 | Gallagher ............ C07K 14/001 514/21.1 |
| 2013/0210724 A1 | 8/2013 | Feizer et al. |
| 2014/0044649 A1 | 2/2014 | Boden et al. |
| 2014/0315810 A1 | 10/2014 | Endo |
| 2015/0051153 A1 | 2/2015 | Reshetnyak et al. |
| 2015/0133630 A1 | 5/2015 | Suga et al. |
| 2016/0058693 A1 | 3/2016 | Widgerow |

OTHER PUBLICATIONS

Katsara, M., et al. Curr. Med. Chem. (2006), 13; 2221-2232.*
International Search Report and Written Opinion corresponding to International Patent Application No. PCT/US2017/023458, dated Aug. 25, 2017, 21 pages.
Adochite (Jul. 30, 2015) "Design and Development of pH-Sensitive Peptides for Cancer Diagnostics", Available at: https://digitalcommons.uri.edu/cgi/viewcontent.cgi?article=1372&context=oa_diss, 3 pages.
Ali (May 2013) "Skin pH: from Basic Science to Basic Skin Care", Acta Dermato-Venereologica, 93(3):261-267.
Andreev et al. (Mar. 13, 2014) "Targeting Diseased Tissues by pHLIP Insertion at Low Cell Surface pH", Frontiers in Physiology, 5(97):7 pages.
Caputo et al. (Mar. 25, 2003) "Using a Novel Dual Fluorescence Quenching Assay for Measurement of Tryptophan Depth within Lipid Bilayers to Determine Hydrophobic Alpha-helix Locations within Membranes", Biochemistry, 42 (11):3265-3274.
Chu et al. (1990) "Efficiency of Cytoplasmic Delivery by pH-Sensitive Liposomes to Cells in Culture", Pharmaceutical Research, 7:824-834.
Clausell et al. (2006) "Membrane Association and Contact Formation by a Synthetic Analogue of Polymyxin B and its Fluorescent Derivatives", The Journal of Physical Chemistry B, 110(9):4465-4471.
Wimley et al. (Apr. 23, 1996) "Solvation Energies of Amino Acid Side Chains and Backbone in a Family of Host-Guest Pentapeptides", Biochemistry, 35(16):5109-5124.
Eckhardt et al. (2005) "Genomic Analysis of a Spontaneous Model of Breast Cancer Metastasis to Bone Reveals a Role for the Extracellular Matrix", Molecular Cancer Research, 3(1):1-14.
Gatenby et al. (Jan. 2008) "A Microenvironmental Model of Carcinogenesis", Nature Reviews Cancer, 8(1):56-61.
Harris et al. (Feb. 2002) "Structural Basis of Perturbed pKa Values of Catalytic Groups in Enzyme Active Sites", International Union of Biochemistry and Molecular Biology Life, 53(2):85-98.
Johansson et al. (Dec. 15, 2006) "Amino-Acid Solvation Structure in Transmembrane Helices from Molecular Dynamics Simulations", Biophysical Journal, 91(12):4450-4463.
Karabadzhak et al. (Apr. 2012) "Modulation of the pHLIP Transmembrane Helix Insertion Pathway", Biophysical Journal, 102(8): 1846-1855.
Karanth et al. (Feb. 18, 2010) "pH-Sensitive Liposomes-Principle and Application in Cancer Therapy", Journal of Pharmacy and Pharmacology, 59(4):469-483.
Katsara et al. (2006) "Round and Round We Go: Cyclic Peptides in Disease", Current Medicinal Chemistry, 13(19):2221-2232.
Killian et al. (Sep. 2000) "How Proteins Adapt to a Membrane-Water Interface", Trends in Biochemical Sciences, 25(9):429-434.
Kornhauser (2010) "Applications of Hydroxy Acids: Classification, Mechanisms, and Photoactivity", Clinical, Cosmetic and Investigational Dermatology, 3:135-142.
Lambers et al. (Oct. 2006) "Natural Skin Surface pH is on Average Below 5, which is Beneficial for its Resident Flora", International Journal of Cosmetic Science, 28(5):359-370.
Lamonte et al. (2013) "Acidosis Induces Reprogramming of Cellular Metabolism to Mitigate Oxidative Stress", Cancer & Metabolism, 1(1):1-19.
Liu et al. (Apr. 3, 2013) "Zwitterionic Chitosan-Polyamidoamine Dendrimer Complex Nanoparticles as a Ph-Sensitive Drug Carrier", Molecular Pharmaceutics, 10(5):1695-1704.
MacCallum et al. (May 1, 2008) "Distribution of Amino Acids in a Lipid Bilayer from Computer Simulations", Biophysical Journal, 94(9):3393-3404.
Mahoney et al. (Oct. 1, 2003) "Tumor Acidity, Ion Trapping and Chemotherapeutics: I. Acid pH Affects the Distribution of Chemotherapeutic Agents in Vitro", Biochemical Pharmacology, 66(7):1207-1218.
Mandal et al. (Oct. 4, 2011) "Cell-Penetrating Homochiral Cyclic Peptides as Nuclear-Targeting Molecular Transporters", Angewandte Chemie International Edition, 50(41):9633-9637.
McIntyre et al. (Dec. 24, 1991) "Fluorescence Assay for Phospholipid Membrane Asymmetry", Biochemistry, 30(51):11819-11827.
Moon et al. (Jun. 21, 2011) "Side-Chain Hydrophobicity Scale Derived from Transmembrane Protein Folding into Lipid Bilayers", Proceedings of the National Academy of Sciences of the United States of America, 108 (25):10174-10177.
Moshnikova et al. (2013) "Antiproliferative Effect of pHLIP-Amanitin", Biochemistry, 52(7):1171-1178.
Nuutila et al. (Jun. 2005) "Flow Cytometric Quantitative Determination of Ingestion by Phagocytes Needs the Distinguishing of Overlapping Populations of Binding and Ingesting Cells", Cytometry Part A, 65(2):93-102.
Nwe et al. (Sep. 17, 2013) "Gd-Labeled Glycol Chitosan as a pH-Responsive Magnetic Resonance Imaging Agent for Detecting Acidic Tumor Microenvironments", Journal of Medicinal Chemistry, 56(20):7862-7869.
Okada et al. (Jan. 22, 2014) "Ratiometric MRI Sensors Based on Core-Shell Nanoparticles for Quantitative pH Imaging", Advanced Materials, 26(19):2989-2992.
Petkova et al. (Jan. 14, 1999) "Arginine Activity in the Proton-Motive Photocycle of Bacteriorhodopsin: Solid-State NMR Studies of the Wild-Type and D85N Proteins†", Biochemistry, 38(5):1562-1572.
Poon et al. (Jun. 28, 2011) "Layer-by-Layer Nanoparticles with a pH Sheddable Layer for In Vivo Targeting of Tumor Hypoxia", ACS Nano, 5(6):4284-4292.
Roy et al. (2005) "Peptide Hairpins with Strand Segments Containing α- and β- Amino Acid Residues : Cross—Strand Aromatic Interactions of Facing Phe Residues", Biopolymers, 80(6):787-799.
Sela et al. (May 1997) "Different Roles of D-Amino Acids in Immune Phenomena", The FASEB Journal, 11(9):449-456.
Serganova et al. (Oct. 1, 2011) "Metabolic Imaging: A Link Between Lactate Dehydrogenase A, Lactate, and Tumor Phenotype", Clinical Cancer Research, 17(19):6250-6261.

(56) References Cited

OTHER PUBLICATIONS

Shirazi et al. (2014) "Cyclic Peptide-Capped Gold Nanoparticles for Enhanced siRNA Delivery", Molecules, , 19(9):13319-13331.

Shirazi et al. (May 6, 2013) "Efficient Delivery of Cell Impermeable Phosphopeptides by a Cyclic Peptide Amphiphile Containing Tryptophan and Arginine", Molecular Pharmaceutics, 10(5):2008-2020.

Shirazi et al. (2013) "Peptide Amphiphile Containing Arginine and Fatty Acyl Chains as Molecular Transporters", Molecular Pharmaceutics, 10(12):4717-4727.

Styczynski et al. (2008) "BLOSUM62 Miscalculations Improve Search Performance", Nature Biotechnology, 26(3):274-275.

Subbarao et al. (Jun. 2, 1987) "The pH-Dependent Bilayer Destabilization by an Amphipathic Peptide", Biochemistry, 26(11):2964-2972.

Tao et al. (2008) "Imagable 4T1 Model for the Study of Late Stage Breast Cancer", BMC Cancer, 8(228):19 pages.

Van Der Wel et al. (Jun. 26, 2007) "Orientation and Motion of Tryptophan Interfacial Anchors in Membrane-Spanning Peptides†", Biochemistry, 46(25):7514-7524.

Van Der Wel et al. (2000) "Tryptophan-Anchored Transmembrane Peptides Promote Formation of Nonlamellar Phases in Phosphatidylethanolamine Model Membranes in a Mismatch-Dependent Manner†", Biochemistry, 39(11):3124-3133.

Wang (Nov. 1999) "A Theory for the Mechanism of Action of the Alpha-hydroxy Acids Applied to the Skin", Medical Hypotheses, 53(5):380-382.

Weerakkody et al. (2013) "Family of pH (low) Insertion Peptides for Tumor Targeting", Proceedings of the National Academy of Sciences, 110(15):5834-5839.

Weerakkody et al. (Aug. 12, 2016) "Novel pH-Sensitive Cyclic Peptides", Scientific Reports, 6(31322):13 pages.

Wojtkowiak et al. (Dec. 5, 2011) "Drug Resistance and Cellular Adaptation to Tumor Acidic pH Microenvironment", Molecular Pharmaceutics, 8(6):2032-2038.

Yang et al. (Jun. 25, 2004) "Twist, a Master Regulator of Morphogenesis, Plays an Essential Role in Tumor Metastasis", Cell, 117(7):927-939.

Zheng et al. (Feb. 16, 2015) "Development of Bioorthogonal Reactions and Their Applications in Bioconjugation", Molecules, 20(16):3190-3205.

\* cited by examiner

|     | Ala | Arg | Asn | Asp | Cys | Gln | Glu | Gly | His | Ile | Leu | Lys | Met | Phe | Pro | Ser | Thr | Trp | Tyr | Val |
|-----|-----|-----|-----|-----|-----|-----|-----|-----|-----|-----|-----|-----|-----|-----|-----|-----|-----|-----|-----|-----|
| Ala | 4   |     |     |     |     |     |     |     |     |     |     |     |     |     |     |     |     |     |     |     |
| Arg | -1  | 5   |     |     |     |     |     |     |     |     |     |     |     |     |     |     |     |     |     |     |
| Asn | -2  | 0   | 6   |     |     |     |     |     |     |     |     |     |     |     |     |     |     |     |     |     |
| Asp | -2  | -2  | 1   | 6   |     |     |     |     |     |     |     |     |     |     |     |     |     |     |     |     |
| Cys | 0   | -3  | -3  | -3  | 9   |     |     |     |     |     |     |     |     |     |     |     |     |     |     |     |
| Gln | -1  | 1   | 0   | 0   | -3  | 5   |     |     |     |     |     |     |     |     |     |     |     |     |     |     |
| Glu | -1  | 0   | 0   | 2   | -4  | 2   | 5   |     |     |     |     |     |     |     |     |     |     |     |     |     |
| Gly | 0   | -2  | 0   | -1  | -3  | -2  | -2  | 6   |     |     |     |     |     |     |     |     |     |     |     |     |
| His | -2  | 0   | 1   | -1  | -3  | 0   | 0   | -2  | 8   |     |     |     |     |     |     |     |     |     |     |     |
| Ile | -1  | -3  | -3  | -3  | -1  | -3  | -3  | -4  | -3  | 4   |     |     |     |     |     |     |     |     |     |     |
| Leu | -1  | -2  | -3  | -4  | -1  | -2  | -3  | -4  | -3  | 2   | 4   |     |     |     |     |     |     |     |     |     |
| Lys | -1  | 2   | 0   | -1  | -3  | 1   | 1   | -2  | -1  | -3  | -2  | 5   |     |     |     |     |     |     |     |     |
| Met | -1  | -1  | -2  | -3  | -1  | 0   | -2  | -3  | -2  | 1   | 2   | -1  | 5   |     |     |     |     |     |     |     |
| Phe | -2  | -3  | -3  | -3  | -2  | -3  | -3  | -3  | -1  | 0   | 0   | -3  | 0   | 6   |     |     |     |     |     |     |
| Pro | -1  | -2  | -2  | -1  | -3  | -1  | -1  | -2  | -2  | -3  | -3  | -1  | -2  | -4  | 7   |     |     |     |     |     |
| Ser | 1   | -1  | 1   | 0   | -1  | 0   | 0   | 0   | -1  | -2  | -2  | 0   | -1  | -2  | -1  | 4   |     |     |     |     |
| Thr | 0   | -1  | 0   | -1  | -1  | -1  | -1  | -2  | -2  | -1  | -1  | -1  | -1  | -2  | -1  | 1   | 5   |     |     |     |
| Trp | -3  | -3  | -4  | -4  | -2  | -2  | -3  | -2  | -2  | -3  | -2  | -3  | -1  | 1   | -4  | -3  | -2  | 11  |     |     |
| Tyr | -2  | -2  | -2  | -3  | -2  | -1  | -2  | -3  | 2   | -1  | -1  | -2  | -1  | 3   | -3  | -2  | -2  | 2   | 7   |     |
| Val | 0   | -3  | -3  | -3  | -1  | -2  | -2  | -3  | -3  | 3   | 1   | -2  | 1   | -1  | -2  | -2  | 0   | -3  | -1  | 4   |

FIG. 17

PH-SENSITIVE CYCLIC PEPTIDES

CROSS-REFERENCES TO RELATED APPLICATIONS

This application is a national stage application filed under 35 U.S.C. § 371, of International Patent Application No. PCT/US2017/023458, filed Mar. 21, 2017, which claims the benefit of and priority under 35 U.S.C. § 119(e) to U.S. Provisional Application No. 62/311,156, filed Mar. 21, 2016, the entire content of which are incorporated herein by reference in its entirety for all purposes.

STATEMENT AS TO FEDERALLY SPONSORED RESEARCH

This invention was made with government support under grant number GM073857 and CA133890 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 20, 2018, is named 40984_506001WO_SEQUENCE_LISTING.txt and is 49,636 bytes in size.

INCORPORATION-BY-REFERENCE OF SEQUENCE LISTING

The contents of the sequence listing text file named "40984_506001WO_SEQUENCE_LISTING.txt", which was created on Mar. 20, 2017 and is 47,649 bytes in size, is hereby incorporated by reference in its entirety.

FIELD OF THE INVENTION

The invention generally relates to compositions and methods for delivery of molecules to cell membranes, cells, and tissues, peptides with increased affinity membrane lipid bilayers at low pH, as well as insertion into and passage across membrane lipid bilayers by peptides.

BACKGROUND

It has been observed that many diseased tissues and some normal tissues are acidic, and that tumors are especially so. Tumor development, progression, and invasiveness, as well as other pathological states such as ischemia, stroke, inflammation, arthritis, infection, atherosclerosis are associated with the elevation of extracellular acidosis. Extracellular acidity is established at early stages of tumor development, during the avascular phase of carcinoma in situ. As a tumor continues to grow, acidosis increases due to the poor blood perfusion, switch of cancer cells to glycolytic mechanism of energy production even in the presence of oxygen and overexpression of carbonic anhydrases (CA). Adaptations to the highly acidic microenvironment are critical steps in the transition from an avascular pre-invasive tumor to a malignant invasive carcinoma (Wojtkowiak et al. (2011) Mol Pharm 8(6):2032-2038; Mahoney et al. (2003) Biochem Pharmacol 66(7):1207-1218; Gatenby R A & Gillies R J (2008) Nat Rev Cancer 8(1):56-61; Lamonte et al. (2013) Cancer Metab 1(1):23).

Among normal tissues, the surface of healthy skin is naturally acidic (pH<6.0).

New compositions and methods for targeting acidic diseased tissues, such as tumor tissues, and normal acidic tissues, such as the surface of skin, are needed.

SUMMARY OF THE INVENTION

The present disclosure provides pH triggered cyclic peptides and short linear peptides. A cyclic peptide is one that comprises a circle geometry or structure. For example, the entire structure of the peptide is circular or a portion of the structure is circular. For example, in the latter case the peptide comprises a cyclic portion and a linear (or tail) portion. In various embodiments, a pH triggered peptide comprises at least 4 amino acids, where (a) at least 2 of the at least 4 amino acids of the peptide are non-polar amino acids, (b) at least 1 of the at least 4 amino acids of the peptide is a protonatable amino acid, and (c) the peptide has a higher affinity to a membrane lipid bilayer at pH 5.0 compared to at pH 8.0. In certain embodiments, a pH triggered peptide comprises at least 4 amino acids, where (a) at least 2 of the at least 4 amino acids of the peptide are non-polar amino acids, (b) at least 1 of the at least 4 amino acids of the peptide is a protonatable amino acid, and (c) a net neutral charge at a low pH and a net negative charge at a neutral or high pH. In various embodiments, 1 or more of the at least 2 non-polar acids is an aromatic amino acid. A peptide is pH triggered if it has, e.g., a higher affinity to a membrane lipid bilayer at pH 5.0 compared to at pH 8.0. In various embodiments, a pH triggered peptide has a net neutral charge at a low pH and a net negative charge at a neutral or high pH. In some embodiments, a pH triggered peptide has a net neutral charge at a pH of less than about 7, 6.5, 6.0, 5.5, 5.0, 4.5, or 4.0 and a net negative charge at a pH of about 7, 7.25, 7.5, or 7.75 in water, e.g., distilled water. In certain embodiments, a pH triggered peptide has a net neutral charge at a pH of less than about 7 and a net negative charge at a pH of about 7 in water. In some embodiments, a pH triggered peptide has a net neutral charge at a pH of less than about 6.5 and a net negative charge at a pH of about 7 in water. In various embodiments, a pH triggered peptide has a net neutral charge at a pH of less than about 6.0 and a net negative charge at a pH of about 7. In some embodiments, a pH triggered peptide has a net neutral charge at a pH of less than about 5.5 and a net negative charge at a pH of about 7in water. In certain embodiments, a pH triggered peptide has a net neutral charge at a pH of less than about 5.0 and a net negative charge at a pH of about 7 in water. In various embodiments, a pH triggered peptide has a net neutral charge at a pH of less than about 4.5 and a net negative charge at a pH of about 7 in water. In some embodiments, a pH triggered peptide has a net neutral charge at a pH of less than about 4.0 and a net negative charge at a pH of about 7 in water. Cyclical pH triggered membrane peptides are referred to herein as "cyclic peptides."

Aspects of the present subject matter also provide a pH triggered peptide comprising at least 4 amino acids, where at least 2 of the at least 4 amino acids of the peptide are non-polar amino acids, at least 1 of the non-polar amino acids of the peptide is an aromatic amino acid, at least 1 of the at least 4 amino acids of said peptide is an amino acid that is protonatable at low pH, and the partitioning or binding of the peptide to a membrane lipid bilayer is stronger at low pH (e.g., pH<6.5 or pH<7.0) compared to the partitioning or binding of the peptide to a membrane lipid bilayer at normal, neutral, or high pH (e.g., pH>6.5 or pH>7.0).

In some embodiments, the cyclic peptide has a net negative charge at a pH of about 7, 7.25, 7.5, or 7.75 in water. Alternatively or in addition, the cyclic peptide may have an acid dissociation constant at logarithmic scale (pKa) of less than about 4.0, 4.5, 5.0, 5.5, 6.0, 6.5, or 7.

In various embodiments, a protonatable amino acid is an amino acid with a pKa of less than about 4.0, 4.5, 5.0, 5.5, 6.0, 6.5, or 7. In certain embodiments, a protonatable amino acid is an amino acid with a pKa of less than about 6.5. In some embodiments, a protonatable amino acid is an amino acid with a pKa of less than about 5.5. In certain embodiments, a protonatable amino acid is an amino acid with a pKa of less than about 4.5. In various embodiments, a protonatable amino acid is an amino acid with a pKa of less than about 4.0. In some embodiments, a protonatable amino acid comprises a carboxyl group.

Aspects of the present subject matter relate to cyclic peptides of various sizes. For example, a cyclic peptide may have 4, 5, 6, 7, 8, 9, 10, 11, 12, 13, 14, 15, 16, 17, 18, 19, or 20 or more amino acids; 4 to 15 amino acids; 8 to 15 amino acids; 8 to 12 amino acids; 8 to 10 amino acids; less than about 20 amino acids; less than 8, 9, 10, 11, 12, 13, 14, or 15 amino acids; less than 10 amino acids; or 10 or less amino acids. In some embodiments, less than 1, 2, 3, 4, or 5 of the amino acids in the cyclic peptide have a net positive charge at a pH of 7, 7.25, 7.5, or 7.75 in water. In certain embodiments, the cyclic peptide comprises 0 amino acids having a net positive charge at a pH of about 7, 7.25, 7.5, or 7.75 in water.

In various implementations of the present subject matter, a cyclic peptide has a functional group to which a cargo compound may be attached. In a non-limiting example, the functional group is a side chain of an amino acid of the cyclic peptide. In certain embodiments, the functional group is an amino acid side chain to which a cargo compound may be attached via a disulfide bond. In some embodiments, the functional group to which a cargo compound may be attached comprises a free sulfhydryl (SH) or selenohydryl (SeH) group. For example, a functional group may be present within a sidechain of a cysteine, homocysteine, selenocysteine, or homoselenocysteine, or a derivative thereof having at least one, e.g., 1, 2, 3, 4, 5, or more, free SH and/or SeH groups. In various embodiments, the functional group comprises a primary amine. For example, a functional group may be present within a sidechain of a lysine or a derivative thereof having at least one, e.g., 1, 2, 3, 4, 5, or more, primary amines.

In certain embodiments, cyclic peptides have about 1, 2, 3, 4, 5, 6, 7, 8, 9, 10 or more aromatic amino acids. For example, the aromatic amino acids may be one or more of a tryptophan, a tyrosine, a phenylalanine, and an artificial aromatic amino acid.

Cyclic peptides of the present subject matter have at least 1 protonatable amino acid. For example, a cyclic peptide may comprise 1 protonatable amino acid which is aspartic acid, glutamic acid, or gamma-carboxyglutamic acid; or at least 2, 3, 4, 5, 6, 7, 8, 9, 10 or more protonatable amino acids, wherein the protonatable amino acids comprise one or more of aspartic acid, glutamic acid, and gamma-carboxyglutamic acid. In some embodiments, the protonatable amino acid is an artificial amino acid. In a non-limiting example, a cyclic peptide has at least 2, 3, 4, 5, 6, 7, 8, 9, 10 or more protonatable amino acids, wherein the protonatable amino acids comprise aspartic acid, glutamic acid, gamma-carboxyglutamic acid, or any combination thereof.

Aspects of the present subject matter provide cyclic peptides having artificial amino acids, such as at least 1 artificial protonatable amino acid. In various embodiments, the artificial protonatable amino acid comprises at least 1, 2, 3, 4 or 5 carboxyl groups and/or the cyclic peptide may have at least 1, 2, 3, 4, 5, 6, 7, 8, 9, 10, 11, 12, 13, 14, or 15 carboxyl groups. In some embodiments, a cyclic peptide has at least 1, 2, 3, 4, 5, 6, 7, 8, 9, 10, 11, 12, 13, 14, 15, 16, 17, 18, 19, or 20 artificial amino acids. In a non-limiting example, every amino acid of the cyclic peptide is an artificial amino acid. In certain embodiments, a cyclic peptide may include at least 1, 2, 3, 4, 5, 6, 7, 8, 9, 10, 11, 12, 13, 14, 15, 16, 17, 18, 19, or 20 D-amino acids.

Various implementations of the present subject matter relate to cyclic peptides having at least one artificial amino acid which is a cysteine derivative, an aspartic acid derivative, a glutamic acid derivative, a phenylalanine derivative, a tyrosine derivative, or a tryptophan derivative. For example, a cyclic peptide may contain a cysteine derivative selected from the group consisting of D-Ethionine, Seleno-L-cystine, S-(2-Thiazolyl)-L-cysteine, and S-(4-Tolyl)-L-cysteine; an aspartic acid derivative which is a N-phenyl (benzyl)amino derivative of aspartic acid; a glutamic acid derivative selected from the group consisting of γ-Carboxy-DL-glutamic acid, 4-Fluoro-DL-glutamic acid, and (4S)-4-(4-Trifluoromethyl-benzyl)-L-glutamic acid; a phenylalanine derivative selected from the group consisting of (S)—N-acetyl-4-bromophenylalanine, N-Acetyl-2-fluoro-DL-phenylalanine, N-Acetyl-4-fluoro-DL-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, 4-(Hydroxymethyl)-D-phenylalanine, N-(3-Indolylacetyl)-L-phenylalanine, p-Iodo-D-phenylalanine, α-Methyl-DL-phenylalanine, 4-Nitro-DL-phenylalanine, and 4-(Trifluoromethyl)-D-phenylalanine; a tyrosine derivative selected from the group consisting of α-Methyl-DL-tyrosine, 3-Chloro-L-tyrosine, 3-Nitro-L-tyrosine, and DL-o-Tyrosine; and/or a tryptophan derivative selected from the group consisting of 5-Fluoro-L-tryptophan, 5-Fluoro-DL-tryptophan, 5-Hydroxy-L-tryptophan, 5-Methoxy-DL-tryptophan, or 5-Methyl-DL-tryptophan.

Cyclic peptides of various symmetries are provided. In a non-limiting example, a cyclic peptide is symmetric on either side of an axis drawn from the functional group through the center of the cyclic peptide. Alternatively, a cyclic peptide may be asymmetric on either side of an axis drawn from the functional group through the center of the cyclic peptide.

In various embodiments, a cyclic peptide has at least 8 amino acids, wherein, at least 2, 3, 4, 5, or 6 of the 8 amino acids of said cyclic peptide are non-polar, and at least 1 or 2 of the at least 8 amino acids of said cyclic peptide is protonatable. For example, the cyclic peptide may have 8-10 amino acids, including at least 2, 3, 4, 5, or 6 of the 8-10 amino acids that are non-polar, and at least 1 or 2 amino acids that are protonatable. In certain embodiments, a cyclic peptide has the sequence $c[(XY)_n(XZ)_m]$ or $c[X_mY_kZ_m]$, wherein X is tryptophan, phenylalanine, tyrosine, or any combination thereof; Y is aspartic acid, glutamic acid, or any combination thereof; Z is a functional group to which a cargo compound may be attached; n is an integer from 1 to 10; m is an integer from 1 to 5; and k is an integer from 1 to 10. In some embodiments, a cyclic peptide may have the sequence $c[(X_nY_m)_kZ_p]$ or $c[Y_mX_nZ_p]$, wherein X is tryptophan, phenylalanine, tyrosine, or any combination thereof; Y is aspartic acid, glutamic acid, or any combination thereof; Z is any amino acid; X and Y and Z can be in any position within a sequence; n is an integer from 1 to 15; m is an integer from 1 to 15; k is an integer from 1 to 8; p is an integer from 0 to 14; and n+m+p≤16.

Also provided herein are cyclic peptides that are covalently attached to a linear peptide. A linear peptide that is covalently attached to a cyclic peptide may optionally be referred to herein as a "tail." Thus, a "cyclic peptide with a tail" a "cyclic peptide comprising a tail" and the like refer to a compound comprising a cyclic peptide that is covalently attached to a linear peptide. In some non-limiting examples, the covalent attachment comprises an ester bond, a disulfide bond, a bond between two selenium atoms, a bond between a sulfur and a selenium atom, an acid-liable bond, or a bond that has been formed by a click reaction. Non-limiting examples of click reactions include reactions between an azide and an alkyne; an alkyne and a strained difluorooctyne; a diaryl-strained-cyclooctyne and a 1,3-nitrone; a cyclooctene, trans-cycloalkene, or oxanorbornadiene and an azide, tetrazine, or tetrazole; an activated alkene or oxanorbornadiene and an azide; a strained cyclooctene or other activated alkene and a tetrazine; or a tetrazole that has been activated by ultraviolet light and an alkene. In various embodiments, the tail is attached to the cyclic peptide via an amino acid sidechain (sometimes referred to as an "R group") of the cyclic peptide. In certain embodiments, the cyclic peptide and the tail are connected via a disulfide bond. In some embodiments, the tail is attached to a cyclic peptide via a disulfide bond that has been formed by reacting a thiol (e.g., on a cysteine or an artificial amino acid) of the cyclic peptide with a thiol (e.g., on a cysteine or an artificial amino acid) of the linear peptide. In some embodiments, the cyclic peptide and the tail are connected via a peptide bond. In various embodiments, the peptide bond has been formed between a primary amine of the cyclic peptide (e.g., on a lysine sidechain or an artificial amino acid) and a carboxyl group at the C-terminus of the tail. In some embodiments, the peptide bond has been formed between a primary amine of the tail (e.g., at the N-terminus, on a lysine sidechain, or on an artificial amino acid) and a carboxyl group of the cyclic peptide (e.g., on a glutamic acid or aspartic acid sidechain, or the sidechain of an artificial amino acid). Preferably, the cyclic peptide comprises 4-8 amino acids (e.g., 4, 5, 6, 7, or 8 amino acids) and the tail comprises 2-8 amino acids (e.g., 2, 3, 4, 5, 6, 7, or 8 amino acids). In some embodiments, the N-terminus of the tail is attached to the cyclic peptide. In certain embodiments, the C-terminus of the tail is attached to the cyclic peptide. In non-limiting examples, the C-terminus of the tail is attached to the cyclic peptide, and another compound is covalently attached to the N-terminus of the tail, e.g., so as to form a methoxy or ethoxy group. Optionally, a cargo compound may be attached to the cyclic peptide, the tail, or the cyclic peptide and the tail. In various embodiments, the tail comprises a cysteine (e.g., to which a cargo molecule may be attached). In some embodiments, the N-terminus of the tail is attached to the cyclic peptide and the C-terminus of the tail is attached to a cargo molecule (e.g., a cargo compound as disclosed herein such as an imaging, therapeutic, prophylactic, or cosmetic agent). In some embodiments, the C-terminus of the tail is attached to the cyclic peptide and the N-terminus of the tail is attached to a cargo molecule (e.g., a cargo compound as disclosed herein such as an imaging, therapeutic, prophylactic, or cosmetic agent).

Aspects of the present disclosure provide cyclic peptides linked to a cargo compound. In various implementations, the cyclic peptide is directly linked to a cargo compound by a covalent bond. In some non-limiting examples, the covalent bond is an ester bond, a disulfide bond, a bond between two selenium atoms, a bond between a sulfur and a selenium atom, or an acid-liable bond.

In some embodiments, the covalent bond between the cyclic peptide and the cargo compound is a bond that has been formed by a click reaction. Non-limiting examples of click reactions include reactions between an azide and an alkyne; an alkyne and a strained difluorooctyne; a diaryl-strained-cyclooctyne and a 1,3-nitrone; a cyclooctene, trans-cycloalkene, or oxanorbornadiene and an azide, tetrazine, or tetrazole; an activated alkene or oxanorbornadiene and an azide; a strained cyclooctene or other activated alkene and a tetrazine; or a tetrazole that has been activated by ultraviolet light and an alkene.

Some implementations provide a cyclic compound that is attached to a linker compound by a covalent bond, wherein the linker compound is attached to the cargo compound by a covalent bond. In non-limiting examples, the covalent bond between the cyclic peptide and the linker compound and/or the covalent bond between the linker compound and the cargo compound is a disulfide bond, a bond between two selenium atoms, a bond between a sulfur and a selenium atom, or a bond that has been formed by a click reaction.

In various embodiments, the cargo has a weight of (a) at least about 0.5, 1, 1.5, 2, 2.5, 5, 6, 7, 8, 9, or 10 kilodaltons (kDa); or (b) less than about 0.5, 1, 1.5, 2, 2.5, 5, 6, 7, 8, 9, or 10 kDa. In a non-limiting example, a cyclic peptide is linked to a cargo compound having a weight of at least about 15 kDa. The cargo may be, e.g., polar or nonpolar.

In certain embodiments, the cargo is a marker and/or a therapeutic, diagnostic, radiation-enhancing, radiation-sensitizing, imaging, gene regulation, cytotoxic, apoptotic, or research reagent. In some embodiments, a cyclic peptide is linked to one or more cargo molecules used as a therapeutic, diagnostic, imaging, immune activation, gene regulation or cell function regulation agent, radiation-enhancing agent, radiation-sensitizing agent, or as a research tool. In various non-limiting examples, the cargo comprises a dye, a fluorescent dye, a fluorescent protein, a nanoparticle, or a radioactive isotope. For example, the cargo may include, e.g., phalloidin, phallo toxin, amanitin toxin, a DNA intercalator, or a peptide nucleic acid. In some embodiments, the cargo comprises a magnetic resonance, positron emission tomography, x-ray contrast agent, single photon emission computed tomography, or fluorescence imaging agent.

In some implementations of the present subject matter, 1 or more of the amino acid side chains of the cyclic peptide are chemically modified to be radioactive or detectable by probing radiation. In various embodiments one or more atoms of a cyclic peptide are replaced by a radioactive isotope or a stable isotope.

Aspects of the present subject matter relate to the use of a cyclic peptide as an agent to deliver a cargo molecule across cell membranes to cells in a diseased tissue with a naturally acidic extracellular environment or in a tissue with an artificially induced acidic extracellular environment relative to normal physiological pH. In a non-limiting example, the diseased tissue is selected from the group consisting of inflamed tissue, ischemic tissue, arthritic tissue, tissue infected with a microorganism, and atherosclerotic tissue.

In various embodiments, artificially inducing an acidic extracellular environment relative to normal physiological pH comprises administering glucose or an acidic solution to the subject. For example, glucose or an acidic solution (e.g., comprising lactic acid) may be administered to the skin or a tissue (e.g., tumor) site. In non-limiting examples relating to the skin, a composition comprising an acid such as lactic acid or hyaluronic acid (used, e.g., in a cosmetic composition) may be applied to the skin.

Alternatively or in addition, a cyclic peptide may be used as an agent to facilitate the attachment of a cargo molecule to the surface of skin. For example, a cyclic peptide may be linked to a cargo molecule that is a cosmetic compound. In some embodiments, the cosmetic compound is a colorant.

In various embodiments, the cargo is a compound that treats, reverses, reduces, or prevents hair loss. Non-limiting examples of such compounds include vasodilators, 5-alpha-reductace inhibitors, finasteride, dutasteride, fluridil, spironolactone latanoprost, bimatoprost, minoxidil, tretinoin, ketoconazole, alfatradiol, topilutamide, and melatonin. Aspects of the present subject matter provide a method of treating a subject afflicted with hair loss comprising administering an effective amount of the cyclic peptide of claim 57 to the scalp of the subject. For example, the hair loss may be androgenetic alopecia.

The present disclosure also provides cyclic compounds linked to an antibiotic compound.

In various embodiments, the cargo balances skin surface pH, and/or is useful for treating acne or eczema, and/or for reducing the development of a scar or the visibility of a scar and/or for reducing visible signs of aging.

In another example, the cargo is a chemotherapeutic compound.

Aspects of the present subject matter also provide a topical composition comprising a cyclic peptide in a topically suitable carrier. For example, the composition may be a cosmetic composition. Also provided is a cosmetic system that includes (a) a cyclic peptide covalently bound to a cosmetic compound, and (b) a cyclic peptide removal composition comprising a pH of at least about 7, 7.5, 8, or 8.5. In various embodiments, the cyclic peptide removal composition is suitable for topical application. In a non-limiting example, the cosmetic compound comprises a coloring agent. Optionally, a cosmetic system may further include (c) a moisturizer and/or a composition that lowers the pH of the skin to a pH less than about 7 or 7.5, wherein (c) is for application to the skin after the cyclic peptide removal composition.

Various implementations of the present subject matter relate to a diagnostic conjugate comprising a cyclic peptide and a pharmaceutically acceptable detectable marker linked thereto. In some embodiments, the detectable marker comprises a dye or a nanoparticle.

The peptide has a higher affinity for a membrane lipid bilayer at low pH compared to that at normal pH. For example, the affinity is at least 5 times higher at pH 5.0 than at pH 8.0. In some embodiments, the affinity is at least 10 times higher at pH 5.0 than at pH 8.0. In some embodiments, the binding/association/partitioning of a cyclic peptide with a membrane lipid bilayer is stronger at low pH (e.g., pH<6.5 or 7.0) compared to a higher pH (e.g., pH≥6.5 or 7.0).

In some embodiments, the non-polar amino acid or amino acids comprise alanine, valine, isoleucine, leucine, methionine, phenylalanine, tyrosine, or tryptophan. In some embodiments, a polar amino acid or amino acids comprise serine, threonine, asparagine, or glutamine. In some embodiments, the non-polar amino acid is an artificial amino acid such as 1-methyl-tryptophan.

In various embodiments, a non-polar amino acid is defined as one having a side-chain solvation energy≥0.5 kcal/mol. The values of solvation energy ($\Delta G_X^{corr}$) for the 20 common natural amino acids are known, e.g., as determined by Wimley W C, Creamer T P & White S H (1996) Biochemistry 35, 5109-5124 or by Moon and Fleming, (2011) Proc. Nat. Acad. Sci. USA 101:10174-10177 (hereinafter Wimley et al. 2011), the entire content of which is incorporated herein by reference. the table below provides exemplary side chain solvation energies for naturally occurring amino acids.

TABLE 1

Solvation Free Energies of the Side Chains (X) of the 20 Natural Amino Acids in AcWL-X-LL and Ac-X-Amide

| residue[a] | charge | mole fraction[b] | | | | Flory-Higging[c] | |
|---|---|---|---|---|---|---|---|
| | | $\Delta G_X^{cor\ d}$ | $\Delta G_X^{GXG\ e}$ | $\Delta G_X^{FP\ f}$ | $\Delta G_X^{KS\ g}$ | $\Delta G_X^{cor\ d}$ | $\Delta G_X^{GXG\ e}$ |
| Ala | | +0.65 | +0.81 | +0.42 | +0.13 | +0.69 | +0.99 |
| Arg | +1 | −0.66 | −0.47 | −1.37 | | +1.44 | +1.81 |
| Asa | | +0.30 | +0.32 | −0.79 | | +1.06 | +1.10 |
| Asp | 0 | +0.72 | +0.75 | | | +1.33 | +1.39 |
| Asp | −1 | −2.49 | −2.46 | −2.46(−1.05) | −3.50 | −1.88 | −1.83 |
| Cys | | +1.17 | +1.39 | +1.39(+2.10) | | +1.72 | +2.14 |
| Glu | | +0.38 | +0.50 | −0.30 | | +1.66 | +1.90 |
| Glu | 0 | +1.04 | +1.17 | | | +2.19 | +2.44 |
| Glu | −1 | −2.48 | −2.35 | −2.35(−0.87) | −3.12 | −1.33 | −1.08 |
| GLY* | | 0 | 0 | 0[h] | 0[h] | 0[h] | 0[h] |
| His | +1 | −1.18 | −0.96 | | | +0.24 | +0.68 |
| His | 0 | +1.04 | +1.27 | +0.18 | +0.16 | +2.46 | +2.90 |
| Ile | | +2.27 | +2.70 | +2.46 | | +3.72 | +4.56 |
| Leu | | +2.40 | +2.77 | +2.30 | | +4.20 | +4.92 |
| Lys | +1 | −1.65 | −1.39 | −1.35 | | +0.17 | +0.67 |
| Met | | +1.82 | +2.18 | +1.68 | | +3.45 | +4.14 |
| Phe | | +2.86 | +3.24 | +2.44 | +2.19 | +4.96 | +5.71 |
| Pro | | +1.01 | +1.35 | +0.67 | +0.29 | +1.59 | +2.28 |
| Ser | | +0.69 | +0.74 | −0.05 | | +0.78 | +0.89 |
| Thr | | +0.90 | +1.08 | +0.35 | | +1.58 | +1.93 |
| Trp | | +3.24 | +3.62 | +3.07 | +2.52 | +6.15 | +6.88 |

TABLE 1-continued

Solvation Free Energies of the Side Chains (X) of the 20 Natural Amino Acids in AcWL-X-LL and Ac-X-Amide

| residue[a] | charge | mole fraction[b] | | | | Flory-Higgins[c] | |
|---|---|---|---|---|---|---|---|
| | | $\Delta G_X^{cor}$ [d] | $\Delta G_X^{GXG}$ [e] | $\Delta G_X^{FP}$ [f] | $\Delta G_X^{KS}$ [g] | $\Delta G_X^{cor}$ [d] | $\Delta G_X^{GXG}$ [e] |
| Tyr | | +1.86 | +2.21 | +1.31 | | +4.08 | +4.75 |
| Val | | +1.61 | +1.99 | +1.66 | | +2.86 | +3.61 |

[a]Residue solvation free energies of the 20 natural amino acids relative to glycine calculated from the data in Table 1 of Wimley et al. 2011. Free energies were corrected for the occlusion of neighboring residue areas (see text) and for the anomalous properties of glycine (see text).
[c]Residue solvation free energies calculated with mole-fraction units.
[b]Residue solvation free energy calculated with the Flory-Huggins correction (Sharp et al. 1991; De Young & Dill, 1990) (see Appendix of Wimley et al. 2011). Constituent molar volumes were taken from Makhatadze et. al. (1990).
[d] Residue solvation free energies for the X residue in the context of a AcWL-X-LL peptide calculated from the free energies in Table 1 or Wimley et al. 2011 using the virtual glycine (GLY*) as the reference (see text of Wimley et al. 2011). $\Delta G_X^{cor} = \Delta G_{WLXLL} - \Delta G_{WLG*LL} + \Delta o_{np} \Delta A_{host}$ where $A_{host}(X) = A_{Trp}(WLXLL) - A_{Xnp}(WLXLL)$. These "corrected" values account for X-dependent changes in the nonpolar ASA of the host peptide. Values for Arg and Lys were calculated from experimental free energies measured at pH 1 where the ionic interaction between the side chain and carboxyl group does not occur. $\Delta G_X^{cor}$ is the best estimate of the solvation energy of residues occluded by neighboring residues of moderate size.
[e] Residue solvation free energies for the X residue in the context of a AcGG-X-GG peptide calculated from $\Delta G_X^{cor}$ and the data in Table 1 of Wimley et al. 2011. $\Delta G_X^{GXG} = \Delta G_X^{cor} + 22.8 \Delta A_y$ where $\Delta A_y = \Delta A_{Xnp}(WLXLL) - \Delta A_{Xnp}(GGXGG)$. This additional correction accounts for occlusion of the guest residue by the host (see text of Wimley et al. 2011). $\Delta G_X^{GXG}$ is the best estimate of the solvation energy of the fully exposed residue.
[f] Modified Fauchère and Pliška (1983) solvation energies, relative to Gly, for the transfer of acetyl amino acid amides from n-octanol to unbuffered aqueous phase. In this modified scale, the original values of FP for Asp, Glu. and Cys have been replaced by the $\Delta G_X^{GXG}$ in the left-hand adjacent column (see text of Wimley et al. 2011). The original values of FP for Asp, Glu, and Cys are shown in parentheses.
[g] Residue solvation free energies relative, relative to Gly, for thetransfer of AcA-X-AtBu tripeptides from n-octanol to buffer, pH 7.2. Data are those of Kim and Szoka (1992).
[h]Reference state is the experimentally determined Gly value rather than GLY*.

Coded amino acids and exemplary non-coded amino acids are listed below in Table 5.

In some embodiments, the cyclical pH triggered membrane peptide comprises one or more cysteine residues. The cysteine residue(s) serves as a point of conjugation of cargo, e.g., using thiol linkage. Other means of linking cargo to the cyclic peptide include esters and/or acid-liable linkages. Ester linkages are particularly useful in humans, the cells of which contain esterases in the cytoplasm to liberate the cargo inside the cells. This system is less useful in the mouse or other rodents, which species are characterized by a high level of esterases in the blood (thereby leading to premature release of cargo molecules). Non cleavable covalent chemical linkages may also be made to secure a cargo permanently to a cyclic peptide.

The cyclic peptides of the composition are useful for topical, dermatological and internal medical applications, e.g., as therapeutic, diagnostic, prophylactic, imaging, gene regulation, or as research reagents/tools, e.g., to evaluate cell function regulation, apoptosis, or other cell activities. For such applications, the composition further comprises a moiety attached to a functional group. Exemplary moieties include cosmetic and other skin care products; imaging agents, dyes, or other detectable labels; and prophylactic, therapeutic and cytotoxic agents. For example, in some implementations cyclic peptides translocate cell permeable and/or cell impermeable cargo molecules, such as nanoparticles, organic dyes, peptides, peptide nucleic acids and toxins, across the membrane. In certain embodiments, the cyclic peptides target cargo (e.g., an imaging agent such as a dye or another detectable label) to cell surfaces in tissues such as acidic tissues. For example, a cyclic peptide linked to an imaging cargo such as a dye or stain can be used during a chromoendoscopy procedure (such as during a colonoscopy) to enhance tissue differentiation or characterization. In various embodiments, the cyclic peptide itself is non-toxic, especially when an effective amount of the cyclic peptide is used. Non-limiting examples of cargo molecules are magnetic resonance (MR), positron emission tomography (PET), single photon emission computed tomography (SPECT), x-ray contrast agents, fluorescence imaging agents, natural toxins, deoxyribonucleic acid (DNA) intercalators, peptide nucleic acids (PNA), morpholino (e.g., morpholino oligomers), peptides, and naturally-occurring or synthetic drug molecules. Other examples of therapeutic or diagnostic moieties or cargo compounds include radiation-enhancing or radiation-sensitizing compounds such as nanogold particles to enhance imaging or cell destruction, e.g., tumor cell killing, by radiation or boron-containing compounds such as Disodium mercapto-closo-dodecaborate (BSH) for boron neutron capture therapy (BNCT) that kills labeled target cells while sparing unlabeled non-target (non-diseased) cells. For imaging or other applications for which detection is desired, one or more atoms are optionally replaced by radioactive isotopes. For example, one or more of the amino acid side chains are chemically modified to render them radioactive or detectable by probing radiation. Further examples include skin care and cosmetic products, where a cyclic peptide may be used to enhance stabilization of a cosmetic, therapeutic or prophylactic moiety on the skin. In some instances, the binding to skin may be reversed by changes in the pH to reverse the cyclic peptide stabilization.

In various embodiments, the moiety or cargo molecule comprises a marker. As used herein, a "marker" may be any compound that provides an identifiable signal. Non-limiting examples of markers are fluorescent dyes, phosphorescent dyes, and quantum dots.

In some embodiments, the marker is a fluorophore. Non-limiting examples of fluorophores include fluorescent dyes, phosphorescent dyes, quantum dots, xanthene derivatives, cyanine derivatives, naphthalene derivatives, coumarin derivatives, oxadiaxol derivatives, pyrene derivatives, acridine derivatives, arylmethine derivatives, or tetrapyrrole derivatives. Xanthene derivatives include but are not limited to fluorescein, rhodamine, Oregon green, eosin, Texas red, and Cal Fluor dyes. Cyanine derivatives include but are not limited to cyanine, indocarbocyanine, indocyanine green (ICG), oxacarbocyanine, thiacarbocyanine, merocyanine, and Quasar dyes. Naphthalene derivatives include but are not limited to dansyl and prodan derivatives. Oxadiazole derivatives include but are not limited to pyridyloxazol, nitrobenzoxadiazole and benzoxadiazole. A non-limiting example of a pyrene derivative is cascade blue. Oxadine derivatives include but are not limited to Nile red, Nile blue, cresyl violet, and oxazine 170. Acridine derivatives include but are not limited to proflavin, acridine orange, and acridine yellow. Arylmethine derivatives include but are not limited to auramine, crystal violet, and malachite green. Tetrapyrrole derivatives include but are not limited to porphin, phtalocyanine, and bilirubin.

In various embodiments, the moiety is covalently attached to the cyclic peptide via linkage such as a thiol linkage or ester linkage or acid-liable linkage. Other types of linkages, chemical bonds, or binding associations are also used. Exemplary linkages or associations are mediated by disulfide, and/or a peptide with a protein binding motif, and/or a protein kinase consensus sequence, and/or a protein phosphatase consensus sequence, and/or a protease-reactive sequence, and/or a peptidase-reactive sequence, and/or a transferase-reactive sequence, and/or a hydrolase-reactive sequence, and/or an isomerase-reactive sequence, and/or a ligase-reactive sequence, and/or an extracellular metalloprotease-reactive sequence, and/or a lysosomal protease-reactive sequence, and/or a beta-lactamase-reactive sequence, and/or an oxidoreductase-reactive sequence, and/or an esterase-reactive sequence, and/or a glycosidase-reactive sequence, and/or a nuclease-reactive sequence.

In certain embodiments, the moiety is covalently attached to the cyclic peptide via a non-cleavable linkage. In various embodiments a non-cleavable linkage is a covalent bond that is not cleaved by an enzyme expressed by a mammalian cell, and/or not cleaved by glutathione and/or not cleaved at conditions of low pH. Non-limiting examples of non-cleavable linkages include maleimide linkages, linkages resulting from the reaction of a N-hydroxysuccinimide ester with a primary amine (e.g., a primary amine of a lysine side-chain), linkages resulting from a click reaction, thioether linkages, or linkages resulting from the reaction of a primary amine (—NH$_2$) or thio (—SH) functional group with succinimidyl-4-(N-maleimidomethyl)cyclohexane-1-carboxylate (SMCC). Exemplary non-cleavable linkages include a maleimide alkane linker,

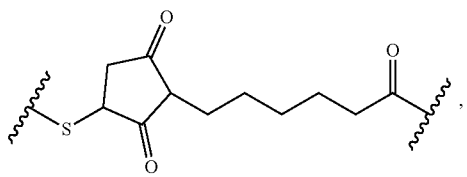 [SMILES: *SC1CC(=O)C(CCCCCC(*)=O)C1=O]

and a maleimide cyclohexane linker,

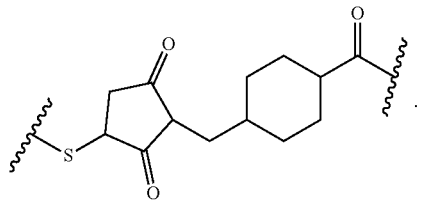 [SMILES: *SC1CC(=O)C(CC2CCC(C(*)=O)CC2)C1=O]

One use of the environmentally-sensitive compositions is to tether molecules to a membrane and/or shuttle molecules across a membrane. For example, the composition is used as an agent to deliver a functional moiety (diagnostic, therapeutic, or cosmetic) to or across cell membranes to cells in a tissue with a naturally acidic extracellular environment or in a tissue with an artificially or disease induced acidic extracellular environment relative to normal physiological pH. Many diseased tissues and normal skin are characterized by an acidic microenvironment. However, acidity in tumors or non-tumor target tissues is optionally induced by co-injection of glucose or a diluted solution of acid at the tissue site at which therapy using the compositions is desired. For example, an acidifying composition (e.g., glucose or dilute acid) is administered, e.g., injected subcutaneously, before delivery of the pH sensitive compositions (30 s, 1 min, 5 min, 10 min, 30 min, 1 hr., 2 hrs, 6 hrs, 12 hrs, 24 hrs, 48 hrs, or more prior to administration of the environmentally sensitive composition to the target tissue site). Alternatively, the tissue acidifying agent and the cyclic peptide composition are co-administered. For example, the diseased tissue is selected from the group consisting of cancer, inflammation/inflamed tissue, ischemia/ischemic tissue, tissue affected by stroke, arthritis, infection with a microorganism (e.g., a bacteria, virus, or fungus), or atherosclerotic plaques. The compositions are also useful to deliver a functional moiety to cell surfaces in a diseased tissue with a naturally acidic extracellular environment or in a tissue with an artificially induced acidic extracellular environment relative to normal physiological pH. Administration of a neutralizing agent to an acidic site, e.g., a bicarbonate solution, is used to reduce cyclic peptide binding/insertion and cyclic peptide labeling or targeting of cells at that site. The compositions are also useful to tether and deliver a cosmetic and/or skin care product to the surface of skin with a naturally acidic environment or to a skin with an artificially induced acidic environment; further, such delivery may be reversed by raising the pH of the environment or skin.

As is described above, the compositions may be used in a clinical setting for diagnostic and therapeutic applications as well as cosmetic applications in humans as well as animals (e.g., companion animals such as dogs and cats as well as livestock such as horses, cattle, goats, sheep, llamas). A diagnostic conjugate comprises the environmentally-sensitive composition and a pharmaceutically-acceptable detectable marker linked thereto. Exemplary detectable markers include a fluorescent dye, and MR, PET, SPECT, optoacoustic, x-ray or CT and other imaging agents. Such conjugates are used in a variety of clinical diagnostic methods, including real-time image-guided therapeutic interventions. For example, a method of guiding surgical tumor excision is carried out by administering to an anatomical site comprising a tumor the conjugate to an anatomical site described above, removing a primary tumor from the site, and detecting residual tumor cells by virtue of binding of the conjugate to residual tumor cells.

Included herein are compositions that are administered to the body for diagnostic and therapeutic use, e.g., using methods known in the art. For example, the methods are carried out by infusing into a vascular lumen, e.g., intravenously, via a jugular vein, peripheral vein or the perivascular space. In some embodiments, the composition is infused into the lungs of said mammal, e.g., as an aerosol or lavage. In certain embodiments, the composition of the invention is administered by injection, e.g., into an anatomical region of interest such as a tumor site or site of another pathological condition or suspected pathological condition. In various embodiments, the composition of the invention is administered by intravesical instillation into a human or animal bladder, oral cavity, intestinal cavity, esophagus, or trachea.

In some embodiments, the injection can be into the peritoneal cavity of the mammal, subdermally, or subcutaneously. The compositions can also be administered transdermally. Solutions containing the imaging conjugates or therapeutic conjugates are administered intravenously, by lavage of the area (e.g., peritoneal tissue or lung tissue), topically, transdermally, by inhalation, or by injection (e.g., directly into a tumor or tumor border area). For example, 1-50 mg in 100 mL is used for lavage and 0.1-100 mg/kg is used for other routes of administration.

Targeting of acidity provides a predictive marker for tumor invasiveness and disease development. In addition to image-guided therapies, the compositions are useful to diagnose or measure the severity of a pathological condition. For example, a method of determining the aggressiveness of a primary tumor is carried out by contacting the tumor with the environmentally-sensitive composition, and an increased level of binding of the composition compared to a control level of binding indicates an increased risk of metastasis from primary tumor. Thus, the compositions aid the physician in determining a prognosis for disease progression and appropriately tailoring therapy based on the severity or aggressiveness of the disease.

A method of preferentially inhibiting proliferation of tumor cells is carried out by administering to a subject suffering from or at risk of developing a tumor the therapeutic conjugate compositions described above to the subject. Tumor cells are preferentially inhibited compared to normal non-tumor cells. The cyclic peptide delivery system, e.g., exemplified by the therapeutic conjugates, are therefore used in a method of manufacturing a pharmaceutical composition or medicament for treatment of tissues characterized by disease or an acid microenvironment.

A method of delivering of cosmetic and skin care products to human or animal skin is carried out by topical administration. Skin pH is normally less than 6.0. The cyclic peptide delivery system, e.g., exemplified by the functional conjugates, are therefore used in a method of manufacturing skin care and cosmetic products.

Aspects of the present subject matter also provide a pH triggered linear peptide comprising a linear counterpart of any cyclic peptide disclosed herein. As used herein, a "linear counterpart" of a cyclic peptide is a linear peptide comprising a stretch of consecutive amino acids in a sequence that is the same as the sequence of consecutive amino acids in the cyclic peptide starting at any amino acid within the cyclic peptide and proceeding around the cyclic peptide.

The present disclosure provides a pH triggered linear peptide comprising (a) a total of at less than 19, 18, 16, 15, 14, 13, 12, 11, 10, 8, 7, 6, or 5 amino acids; (b) at least 2 non-polar amino acids, wherein at least 1 of the at least 2 non-polar amino acids is an aromatic amino acid; and (c) at least 1 protonatable amino acid, wherein the peptide has a higher affinity to a membrane lipid bilayer at pH 5.0 compared to at pH 8.0.

In various embodiments, the linear peptide has the sequence $(X_nY_m)_kZ_p$ or $Y_mX_nZ_p$, wherein X is tryptophan, phenylalanine, tyrosine, or any combination thereof; Y is aspartic acid, glutamic acid, or any combination thereof; Z is any amino acid; X and Y and Z could be in any position within a sequence; n is an integer from 1 to 15; m is an integer from 1 to 15; k is an integer from 1 to 8; p is an integer from 0 to 14; and n+m+p≤16.

Aspects of the present invention provide linear peptides that are not linked to a cargo compound. Such linear peptides may be useful as, e.g., moisturizers or otherwise as an alternative to a hydroxyl acid for topical administration. In some embodiments, the linear peptide may have at least 2, 3, 4, 5, 6, 7, 8, 9, 10, 11, 12, 13, 14, or 15 carboxyl groups.

Certain implementations of the present subject matter provide linear peptides having at least 2, 3, 4, 5, 6, 7, 8, 9, 10, 11, 12, 13, 14, or 15 aromatic amino acids or wherein at least about 10, 15, 20, 25, 30, 35, 40, 45, 50, 55, 60, 65, 70, or 75% of the amino acids in the linear peptide are aromatic amino acids.

In various embodiments, a linear peptide has an amino acid with a side chain to which a cargo compound may be attached. In some embodiments, a linear peptide further comprises a cargo compound. For example, a cargo compound may be covalently linked to an amino acid at the N-terminal or C-terminal side of the linear peptide. Alternatively or in addition, a cargo compound is covalently linked to an amino acid of the linear peptide, wherein the amino acid is other than an amino acid at the N-terminal or C-terminal side of the linear peptide.

In some embodiments a linear peptide not form a helical structure at a pH of about 4.0, 4.5, 5.0, 5.5, 6.0, 6.5, or 7, or forms a helical structure that is too short to span a lipid bilayer.

Any cargo compound mentioned herein may be linked to a linear peptide. For example, a cargo compound may be a cosmetic compound or an antimicrobial compound.

Disclosures relating to cyclic peptides and topical applications may be applied to linear peptides.

Aspects of the present subject matter provide a method for altering the appearance of skin comprising applying a linear peptide to the surface of the skin. Non-limiting examples of altering the appearance of the skin include reducing the appearance of a wrinkle or a dark spot, or altering the color of the skin.

Further aspects of the present subject matter provide a method for treating or preventing a microbial infection of skin or a mucous membrane comprising applying a linear peptide to the skin or the mucous membrane.

Non-limiting descriptions relating to cyclic peptides are provided in Weerakkody et al. (2016) Sci Rep. 6:31322, the entire content of which (including supplementary information, is incorporated herein by reference.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 17 is the BLOSUM62 matrix.

DETAILED DESCRIPTION OF THE INVENTION

Figure 1B:
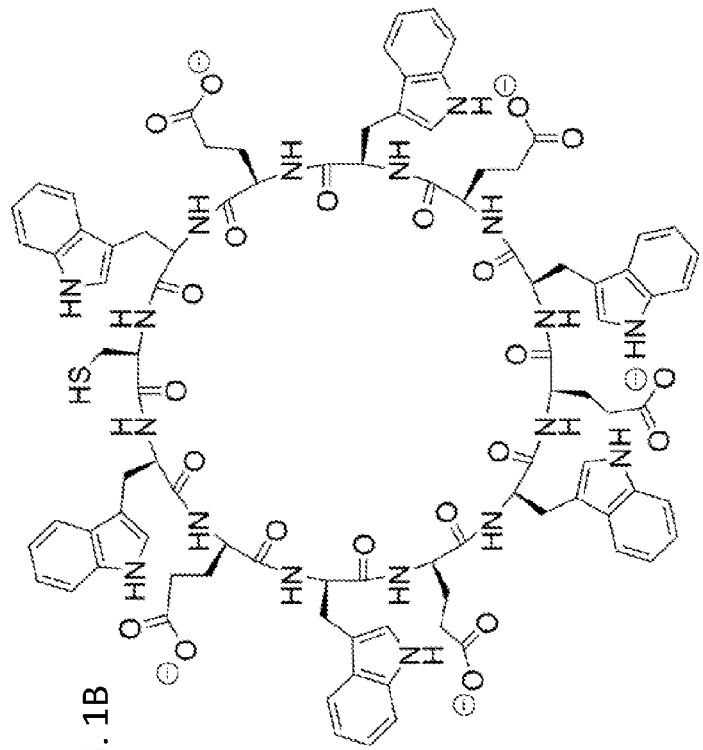
FIG. 1A-F is a set of chemical structures showing peptides containing tryptophan (Trp, W), glutamic acid (Glu, E), and cysteine (Cys, C) residues.
Figure 1A:
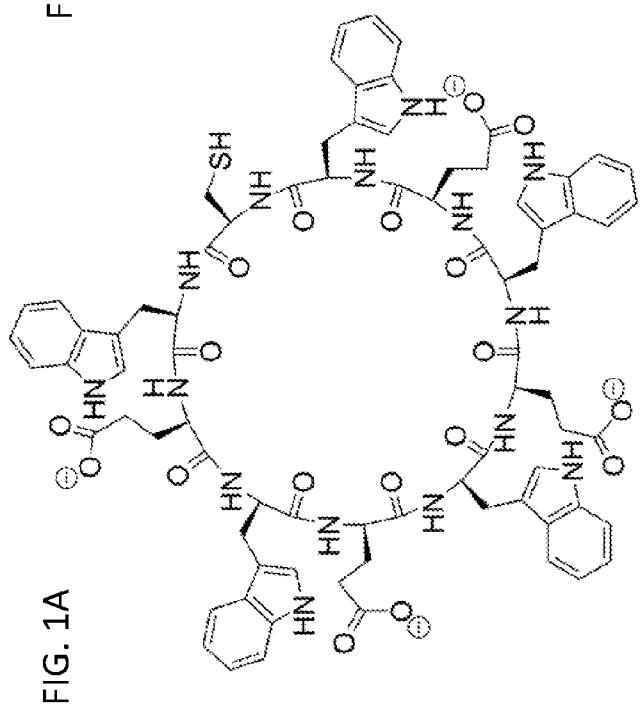
Figure 1D:
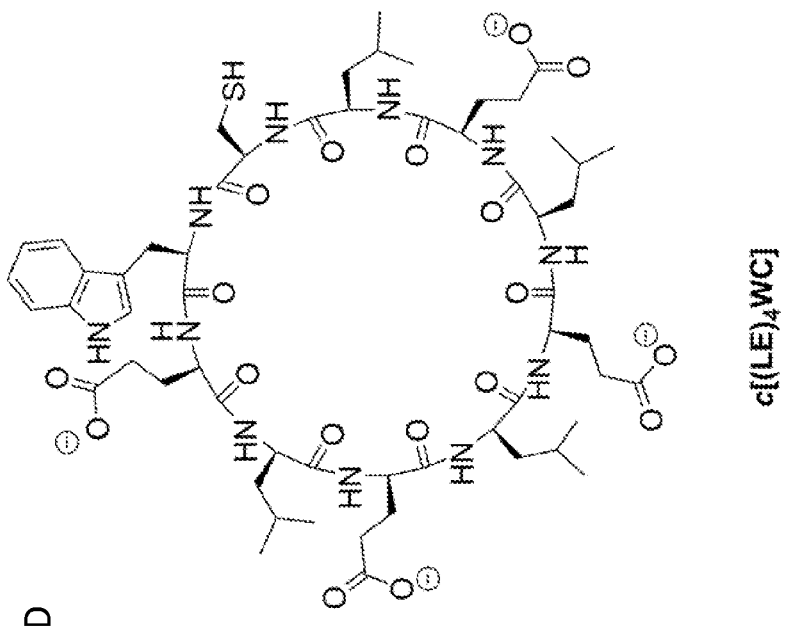
Figure 1C:
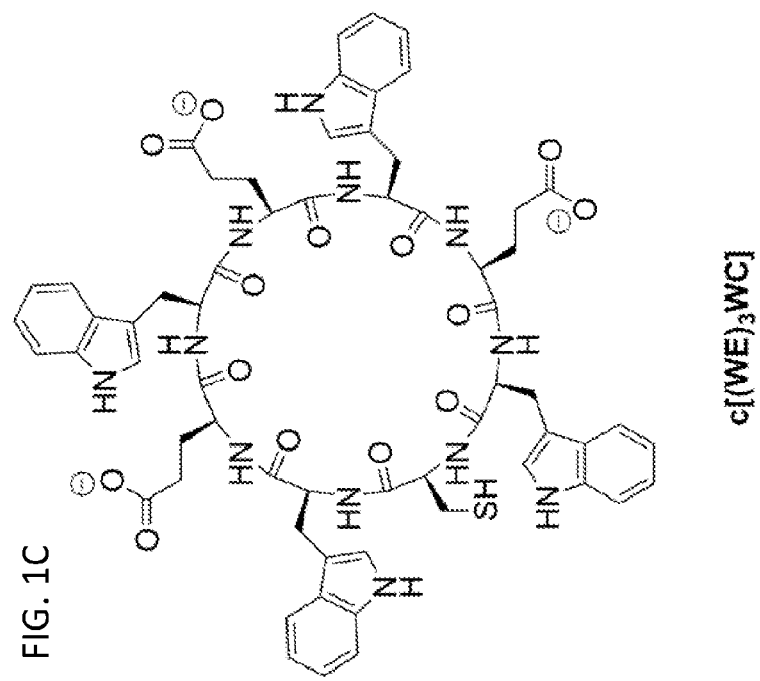
Figure 1F:
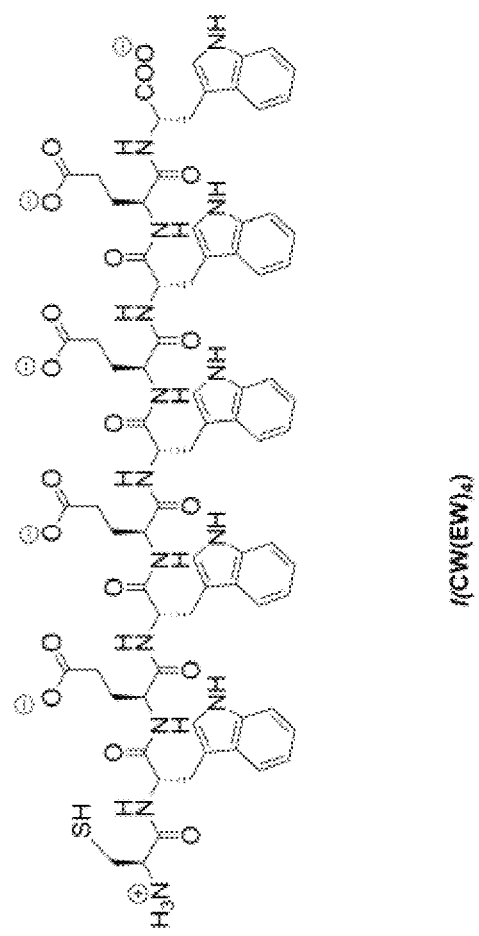
Figure 1E:
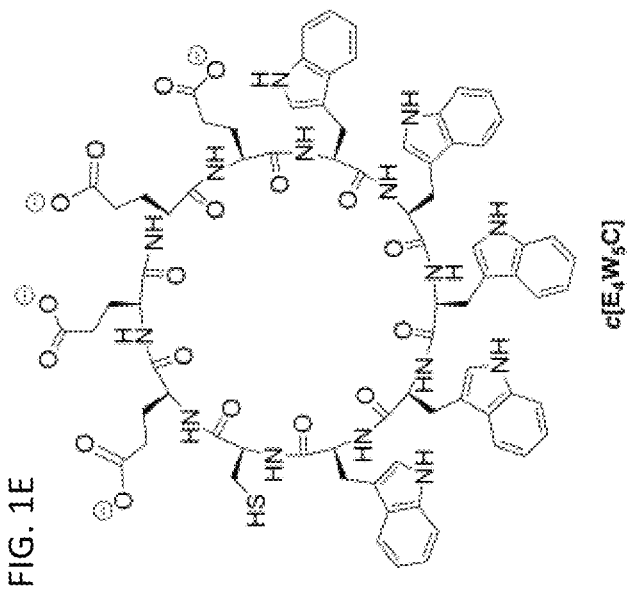

Aspects of the present subject matter relate to the surprising discovery that pH-triggered peptides specifically interact with the lipid bilayer of liposomal and cellular membranes at acidic pHs, and are capable of tethering to the membrane and translocating cargo molecules across these membranes. By pH triggered or pH-responsive is meant that the peptide inserts into the lipid bilayer of a membrane when exposed to a low pH. For example, the peptide inserts at a pH of 7.0 or lower. In various embodiments, such peptides preferably do not completely traverse the cell membrane to gain complete entry into the cytoplasm but remain lodged in the bilayer. In embodiments, the peptides comprise a cyclic geometry or structure. Optionally, a peptide comprises a cyclic structure and a tail structure. Insertion of linear pH-triggered membrane peptides (such as pHLIPs) into membranes (as well as translocation of cargo) has been reported to involve the formation of a helical structure at low pH. See, e.g., U.S. Patent Application No. 2015-0051153, "Environmentally Sensitive Compositions and Methods of Use in the Treatment and Diagnosis of Tumors," published Feb. 19, 2015, the entire content of which is incorporated herein by reference. In embodiments, neither a cyclic peptide nor its short linear counterpart sequence can undergo coil-helix transition and form a transmembrane helical structure across a membrane as long linear pHLIPs do, and suggestions or descriptions relating to the mechanism of long linear pHLIP insertion or translocation cannot be applied to cyclic peptides or their short linear counterparts. As used herein, a "short" peptide is a peptide comprising less than 15 amino acids. In some embodiments, a short peptide comprises less than 13 amino acids. In certain embodiments, a short peptide comprises less than 12 amino acids. A "long" peptide is a peptide comprising a stretch of 15 or more amino acids.

In various embodiments, the cyclic peptide does not form a coil structure in solution and the process of cyclic peptide partitioning into a membrane preferably does not involve any helical or any other secondary structure formation as with long linear pHLIPs. The ability of cyclic peptides to move cell-permeable or cell-impermeable cargo across membranes is surprising. Without wishing to be bound by any scientific theory, this ability may be based on a diffusion-limited process: the diffusion and partitioning of cyclic peptides into a membrane is enhanced at low pH due to the increase of the hydrophobicity of cyclic peptides as a result of the protonation of negatively charged residues.

With respect to drug delivery by cyclic peptides, studies have focused on positively charged peptides such as those containing arginine. These peptides do not have the acid-based targeting of either the pHLIPs or the cyclic peptides. A recent study reported the design and synthesis of homochiral L-cyclic peptides containing arginine (R) and tryptophan (W) residues, and their application for the nuclear delivery of anti-HIV drugs, phosphopeptides, anti-cancer drugs, and siRNA (Mandal et al. (2011) *Angew Chem Int Ed Engl* 50(41):9633-9637; Nasrolahi et al. (2013) *Mol Pharm* 10(5):2008-2020; Nasrolahi et al. (2013) *Mol Pharm* 10(12):4717-4727; Shirazi et al. (2014) *Molecules* 19(9): 13319-13331). These peptides offered several advantages including nuclear delivery of doxorubicin, endocytosis-independent uptake, low cytotoxicity, biocompatibility, hydrophobic drug entrapment through non-covalent interactions, and drug delivery through conjugation.

Figure 13A:
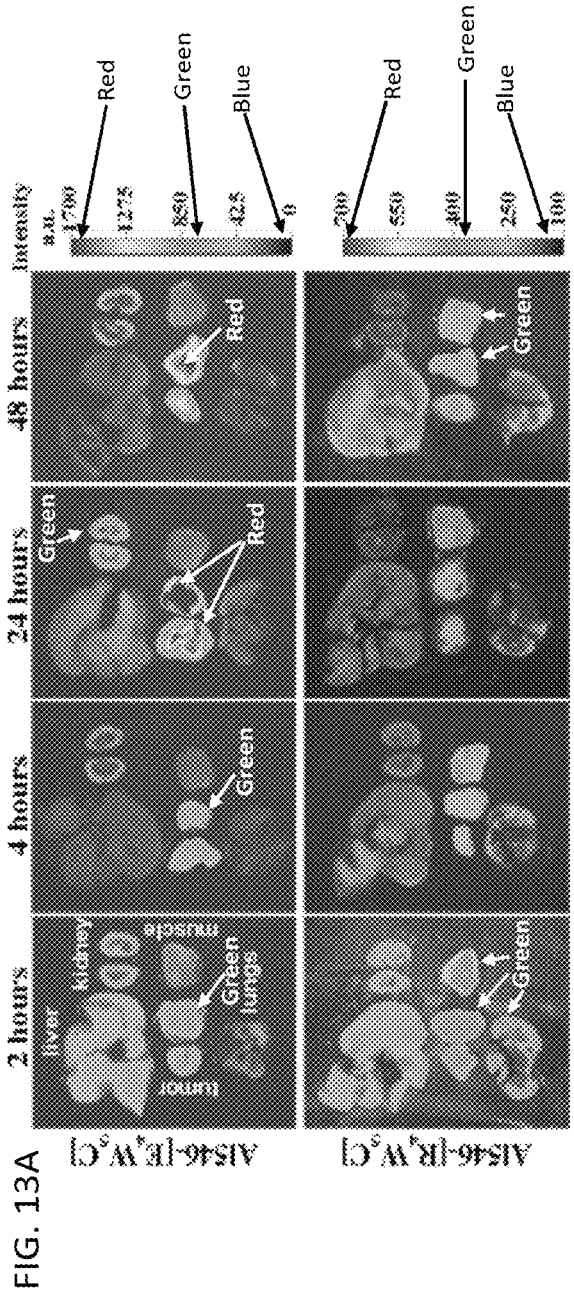
FIGS. 13A and B are images and a graph showing the targeting of peptides to tumors and various organs. (A) Ex vivo fluorescence imaging of tumor, muscle, lungs, liver and kidneys collected at various time points after IV administration of Alexa546 asymmetric c[E$_4$W$_5$C] (SEQ ID NO: 5) and c[R$_4$W$_5$C] (SEQ ID NO: 219) peptides (the kinetics of signal changes in tissue and organs is shown in FIG. 15); (B) Tumor/organ ratios calculated from the obtained data. Three mice per time point, per peptide were used in the study.

However, targeting positively charged cyclic peptides to acidic tissues, such as tumors and skin, has proven difficult in vivo, since positively charged peptides cannot be protonated at low pH, thus became charged and cannot cross a hydrophobic bilayer unless they disrupt it. As shown in Example 1, a positively charged analog of a cyclic peptide (having positively charged arginine residues in the place of the negatively charged glutamic acid residues of the cyclic peptide) was clearly inferior at targeting tumor tissues relative to the cyclic peptide (FIGS. 13A and B).

The present subject matter features diagnostic, cosmetic, and therapeutic agents comprising cyclic peptides that selectively deliver compositions to acidic tissue compared to nonacidic tissue, thereby significantly improving diagnosis, treatment and delivery of cosmetic and skin care products to skin. Aspects of the present subject matter relate to the development of a class of delivery vehicles based on pH-sensitive, water soluble peptides (cyclic peptides), that target acidic tissues such as skin. Cyclic peptides described herein also target cells located in an acidic microenvironment found in many diseased tissues, including tumors. Cyclic peptides partition into a lipid bilayer membrane at low pH (<7.0) but not at high pH. Cyclic peptides have a dual delivery capability: they can tether cargo molecules or nanoparticles to the surfaces of cells in acidic tissues and/or they can move a cell-impermeable cargo molecule across the membrane into the cytoplasm. A drop in pH leads to the protonation of negatively charged residues (e.g., Asp or Glu), which enhances peptide hydrophobicity, increasing the affinity of the peptide for the lipid bilayer and facilitating subsequent membrane partition.

Aspects of the present subject matter provide cyclic peptides with dual delivery capabilities: A cyclic peptide can (i) tether cargo molecules to the cell surface and/or (ii) inject and release cell-impermeable cargo molecules into the cytoplasm. External cargo of wide range of polarity and size is reliably transported. One non-limiting application is to deliver imaging probes to acidic tissue, where they will be stably tethered to the surfaces of cells. Cyclic peptides deliver and tether various nanoparticles to the surface of skin and cancer cells. In another non-limiting example, the delivery capability of cyclic peptides is based on conjugation of cargo molecules via a bond that is cleaved in the environment of the cytoplasm, such as a disulfide bond. Cargo size is preferably less than 100 kDa. For example, cargo size is in the range of 0.1-50 kDa, 1-25 kDa, and 1-10 kDa. In various embodiments, cargo with a molecular mass of 5 kDa is effectively translocated/delivered across a membrane by a cyclic peptide.

In various embodiments relating to the delivery (e.g., release of the cargo from the cyclic peptide into the cytoplasm) of a cargo compound to the cytoplasm, the cargo compound is linked to the cyclic peptide by a covalent bond that is cleavable in the cytoplasm. A non-limiting example of a bond that may be cleaved in the cytoplasm is a thiol linkage. In certain embodiments where tethering to a cell membrane without cytoplasmic delivery is desired (e.g., tethering to the inner and/or outer leaflet of cell membranes) a non-cleavable linkage" is used. As used herein, the "tethering" of cargo to a membrane means affecting the non-covalent localization of the cargo to the membrane bilayer (e.g., the inner and/or outer leaflet of the membrane).

Aspects of the present subject matter relate to tuning a cyclic peptide to be preferentially tethered to the inner or the outer leaflet of the membrane. In some embodiments, a cyclic peptide is preferentially tethered to the inner leaflet of a membrane if the cyclic peptide has no positively charged amino acids at a pH less than about 7.0. In certain embodiments, a cyclic peptide is preferentially tethered to the outer leaflet of a membrane if the cyclic peptide comprises at least 1 (e.g., 1, 2, or 3) positively charged residue at a pH less than about 7.0. In some embodiments, the positively charged residue is lysine or arginine. In various embodiments, a cyclic peptide is preferentially tethered to the outer leaflet of a membrane if the cyclic peptide is linked to a cargo compound with a pKa less than about 7, 6.75, 6.5, 6.25, 6.0, 5.75, 5.5, or 5.0. In certain embodiments, a cyclic peptide is preferentially tethered to the outer leaflet of a membrane if the cyclic peptide is linked to a cargo compound having a molecular weight of at least about 15, 20, 25, 30, 35, 40, 45, 50, or 15-50 kDa.

Variations in skin pH may occur due to products applied to the skin or how often a subject bathes; however, even with such variations, the surface of the skin is accepted to be acidic. The natural pH of the surface of skin is thought to be under 6.0, and possibly under 5.0. See, e.g., Lambers et al. (2006) Int J Cosmet Sci. 2006 October; 28(5):359-70, the entire content of which is incorporated herein by reference. Cyclic peptides are useful for targeting compositions, such as cosmetic and antimicrobial compounds, to the surface of skin. In various convenient embodiments, cyclic peptides (and compounds conjugated thereto) on the surface of skin may be removed using a neutral or high-pH solution (such as dermatologically acceptable solutions having a pH of at least about 7, 7.5, 7.75, or 8.0).

Cyclic peptides can act as monomers in the following non-limiting diagnostic and therapeutic applications: targeted therapy—selective delivery of therapeutic and imaging agents to acidic diseased tissue, thereby increasing the effective concentration of these agents and reducing their accumulation in healthy tissue; improved route of drug administration: agents with improved pharmacokinetic properties of a drug; locally activated therapy—activation of a targeted therapeutic agent by local microenvironment of acidic diseased tissue; fine specificity—cell-impermeable molecules translocated into cells only in diseased tissue while not affecting healthy cells; and multi-functionality—simultaneous targeted delivery of a therapeutic agent and an imaging probe to monitor drug distribution.

Compositions described herein are characterized by much higher efficacy and/or significantly reduced side effects compared to other cell-penetrating constructs/carriers. Such improvements are especially important for cancer treatment, since the majority of anti-cancer drugs are poisons that damage normal cells. Other diseased tissues are treated using the same compositions. The challenge of selective delivery to tumors or other tissues characterized by a pH lower that physiological pH has been answered by cyclic peptides and constructs described herein. Disease-specific delivery coupled with local activation allows i) accumulating and, therefore, increasing the effective concentration of therapeutic or diagnostic agents in a diseased acidic area and ii) reducing the side effects associated with treatment by reducing the targeting of normal cells. Local activation further improves the protection of normal tissue.

Solubility and Stability of Cyclic Peptides in Blood

Peptide interactions with proteins, especially plasma proteins, and membranes influence the pharmacokinetics of the peptide at neutral pH. Cyclic peptides demonstrate prolonged circulation in the blood, which is consistent with their ability to bind weakly to membrane surfaces at neutral and high pH, preventing the rapid clearance by the kidney expected for a small peptide. Cyclic peptide binding to membranes is driven by hydrophobic interactions and interactions of aromatic amino acids with phospholipid head groups. If the peptide sequence were made more hydrophobic, tighter binding to red blood cells and epithelial cells and more aggregation in solution, and slower clearance and reduced bioavailability would occur. Making the peptide less hydrophobic accelerates clearance and prevents the peptide from finding its targets. Therefore, fine tuning of the solubility is an important property to optimize cyclic peptide performance in vivo.

Another important property is the stability of peptides in the blood, since proteases in the serum can degrade linear peptides consisting of L-amino acids within minutes. Cyclic peptides are degraded at a lower rate than linear long peptides such as pHLIPs. Additionally, the non-natural amino acids (such as D-amino acids) may be used together with or instead of L-amino acids to further inhibit degradation. While polypeptides made from D-amino acids have increased stability, they are often unsuitable for specific receptor binding applications as a consequence of their altered chirality. Since the mechanism of cyclic peptide targeting and membrane partition involves relatively non-specific interactions with a fluid lipid bilayer, cyclic peptides composed of L- or D-amino acids demonstrate the same biophysical and pH targeting properties.

Peptide Sequences

In the tables below and throughout the descriptions herein, a lowercase "c" at the beginning of a sequence herein denotes a cyclic peptide (e.g., as in c[(WE)$_3$WC]) (SEQ ID NO: 1), and a lowercase "l" denotes a linear peptide (e.g., as in l(CW(EW)$_4$)) (SEQ ID NO: 188). In the case of cyclic structures that comprise a tail, the cyclic portion of the compound is within brackets, and the tail portion follows (is to the right of) the brackets. For example, in the compound c[E$_5$K]W$_5$C, c[E$_5$K] is the cyclic peptide portion, and W$_5$C is the peptide tail portion. As another example, in c[E$_5$K]W$_4$C, the cyclic peptide portion is c[E$_5$K] and the peptide tail portion is W$_4$C.

With respect to cyclic peptides, the amino acids within brackets may be present in the order listed in brackets from left to right, or in any order. For example, a cyclic peptide c[X$_2$Y$_2$] may have the corresponding linear sequence: XXYY, XYXY, YXXY, XYYX, or YXYX. In some cases, multiple examples of corresponding linear sequences for an exemplary cyclic peptide are listed in Table 3.

TABLE 2 provides a summary of peptide sequences that have been made and tested.

| Peptide | Sequence | Linear Sequence | SEQ ID NO |
|---------|----------|-----------------|-----------|
| 1 | c[(WE)$_3$WC] | WEWEWEWC | 1 |
| 2 | c[(WE)$_4$WC] | WEWEWEWEWC | 2 |
| 3 | c[(WE)$_5$WC] | WEWEWEWEWEWC | 3 |
| 4 | c[(LE)$_4$WC] | LELELELEWC | 4 |
| 5 | c[E$_4$W$_5$C] | EEEEWWWWWC | 5 |
| 6 | l(CW(EW)$_4$) | CWEWEWEWEW | 188 |
| 7 | c[R$_4$W$_5$C] | RRRRWWWWWC | 219 |

TABLE 3 provides additional non-limiting examples of peptide sequences.

| Cyclic Peptide | Circular Sequence | Linear Sequence | SEQ ID NO |
|----------------|-------------------|-----------------|-----------|
| 1 | c[E$_3$W$_5$C] | EEEWWWWWC | 6 |
| 2 | c[E$_3$W$_5$C] | EWEWWWWEC | 7 |

TABLE 3-continued provides additional non-limiting examples of peptide sequences.

| Cyclic Peptide | Circular Sequence | Linear Sequence | SEQ ID NO |
|---|---|---|---|
| 3 | c[$E_3W_5C$] | EWWEWWWEC | 8 |
| 4 | c[$E_3W_5C$] | EWWWEWWEC | 9 |
| 5 | c[$E_3W_5C$] | EWWWWEWEC | 10 |
| 6 | c[$E_3W_5C$] | EWWWWWEEC | 11 |
| 7 | c[$E_3W_5C$] | EWEEWWWWC | 12 |
| 8 | c[$E_3W_5C$] | EWWEEWWWC | 13 |
| 9 | c[$E_3W_5C$] | EWWWEEWWC | 14 |
| 10 | c[$E_3W_5C$] | EWWWWEEWC | 15 |
| 11 | c[$E_3W_5C$] | WEEEWWWWC | 16 |
| 12 | c[$E_3W_5C$] | WWEEEWWWC | 17 |
| 13 | c[$E_3W_5C$] | WWWEEEWWC | 18 |
| 14 | c[$E_3W_5C$] | WWWWEEEWC | 19 |
| 15 | c[$E_3W_5C$] | WEWEEWWWC | 20 |
| 16 | c[$E_3W_5C$] | WEWWEEWWC | 21 |
| 17 | c[$E_3W_5C$] | WEWWWEEWC | 22 |
| 18 | c[$E_3W_5C$] | WEWWWWEEC | 23 |
| 19 | c[$E_3W_5$] | EEEWWWWW | 24 |
| 20 | c[$E_3W_5$] | EWEWWWWE | 25 |
| 21 | c[$E_3W_5$] | EWWEWWWE | 26 |
| 22 | c[$E_3W_5$] | EWWWEWWE | 27 |
| 23 | c[$E_3W_5$] | EWWWWEWE | 28 |
| 24 | c[$E_3W_5$] | EWWWWWEE | 29 |
| 25 | c[$E_3W_5$] | EWEEWWWW | 30 |
| 26 | c[$E_3W_5$] | EWWEEWWW | 31 |
| 27 | c[$E_3W_5$] | EWWWEEWW | 32 |
| 28 | c[$E_3W_5$] | EWWWWEEW | 33 |
| 29 | c[$E_3W_5$] | WEEEWWWW | 34 |
| 30 | c[$E_3W_5$] | WWEEEWWW | 35 |
| 31 | c[$E_3W_5$] | WWWEEEWW | 36 |
| 32 | c[$E_3W_5$] | WWWWEEEW | 37 |
| 33 | c[$E_3W_5$] | WEWEEWWW | 38 |
| 34 | c[$E_3W_5$] | WEWWEEWW | 39 |
| 35 | c[$E_3W_5$] | WEWWWEEW | 40 |
| 36 | c[$E_3W_5$] | WEWWWWEE | 41 |
| 37 | c[$D_3W_5C$] | DDDWWWWC | 42 |
| 38 | c[$D_3W_5C$] | DWDWWWDC | 43 |
| 39 | c[$D_3W_5C$] | DWWDWWDC | 44 |
| 40 | c[$D_3W_5C$] | DWWWDWDC | 45 |

TABLE 3-continued provides additional non-limiting examples of peptide sequences.

| Cyclic Peptide | Circular Sequence | Linear Sequence | SEQ ID NO |
|---|---|---|---|
| 41 | c[$D_3W_5C$] | DWWWWDWDC | 46 |
| 42 | c[$D_3W_5C$] | DWWWWWDDC | 47 |
| 43 | c[$D_3W_5C$] | DWDDWWWWC | 48 |
| 44 | c[$D_3W_5C$] | DWWDDWWWC | 49 |
| 45 | c[$D_3W_5C$] | DWWWDDWWC | 50 |
| 46 | c[$D_3W_5C$] | DWWWWDDWC | 51 |
| 47 | c[$D_3W_5C$] | WDDDWWWWC | 52 |
| 48 | c[$D_3W_5C$] | WWDDDWWWC | 53 |
| 49 | c[$D_3W_5C$] | WWWDDDWWC | 54 |
| 50 | c[$D_3W_5C$] | WWWWDDDWC | 55 |
| 51 | c[$D_3W_5C$] | WDWDDWWWC | 56 |
| 52 | c[$D_3W_5C$] | WDWWDDWWC | 57 |
| 53 | c[$D_3W_5C$] | WDWWWDDWC | 58 |
| 54 | c[$D_3W_5C$] | WDWWWWDDC | 59 |
| 55 | c[$D_3W_5$] | DDDWWWWW | 60 |
| 56 | c[$D_3W_5$] | DWDWWWWD | 61 |
| 57 | c[$D_3W_5$] | DWWDWWWD | 62 |
| 58 | c[$D_3W_5$] | DWWWDWWD | 63 |
| 59 | c[$D_3W_5$] | DWWWWDWD | 64 |
| 60 | c[$D_3W_5$] | DWWWWWDD | 65 |
| 61 | c[$D_3W_5$] | DWDDWWWW | 66 |
| 62 | c[$D_3W_5$] | DWWDDWWW | 67 |
| 63 | c[$D_3W_5$] | DWWWDDWW | 68 |
| 64 | c[$D_3W_5$] | DWWWWDDW | 69 |
| 65 | c[$D_3W_5$] | WDDDWWWW | 70 |
| 66 | c[$D_3W_5$] | WWDDDWWW | 71 |
| 67 | c[$D_3W_5$] | WWWDDDWW | 72 |
| 68 | c[$D_3W_5$] | WWWWDDDW | 73 |
| 69 | c[$D_3W_5$] | WDWDDWWW | 74 |
| 70 | c[$D_3W_5$] | WDWWDDWW | 75 |
| 71 | c[$D_3W_5$] | WDWWWDDW | 76 |
| 72 | c[$D_3W_5$] | WDWWWWDD | 77 |
| 73 | c[$Gla_3W_5$] | GlaGlaGlaWWWWW | 78 |
| 74 | c[$Gla_3W_5$] | GlaWGlaWWWWGla | 79 |
| 75 | c[$Gla_3W_5$] | GlaWWGlaWWWGla | 80 |
| 76 | c[$Gla_3W_5$] | GlaWWWGlaWWGla | 81 |
| 77 | c[$Gla_3W_5$] | GlaWWWWGlaWGla | 82 |
| 78 | c[$Gla_3W_5$] | GlaWWWWWGlaGla | 83 |

TABLE 3-continued provides additional non-limiting examples of peptide sequences.

| Cyclic Peptide | Circular Sequence | Linear Sequence | SEQ ID NO |
| --- | --- | --- | --- |
| 79 | c[Gla$_3$W$_5$] | GlaWGlaGlaWWWW | 84 |
| 80 | c[Gla$_3$W$_5$] | GlaWWGlaGlaWWW | 85 |
| 81 | c[Gla$_3$W$_5$] | GlaWWWGlaGlaWW | 86 |
| 82 | c[Gla$_3$W$_5$] | GlaWWWWGlaGlaW | 87 |
| 83 | c[Gla$_3$W$_5$] | WGlaGlaGlaWWWW | 88 |
| 84 | c[Gla$_3$W$_5$] | WWGlaGlaGlaWWW | 89 |
| 85 | c[Gla$_3$W$_5$] | WWWGlaGlaGlaWW | 90 |
| 86 | c[Gla$_3$W$_5$] | WWWWGlaGlaGlaW | 91 |
| 87 | c[Gla$_3$W$_5$] | WGlaWGlaGlaWWW | 92 |
| 88 | c[Gla$_3$W$_5$] | WGlaWWGlaGlaWW | 93 |
| 89 | c[Gla$_3$W$_5$] | WGlaWWWGlaGlaW | 94 |
| 90 | c[Gla$_3$W$_5$] | WGlaWWWWGlaGla | 95 |
| 91 | c[E$_3$W$_4$C] | EEEWWWC | 96 |
| 92 | c[E$_3$W$_4$C] | EWEWWWEC | 97 |
| 93 | c[E$_3$W$_4$C] | EWWEWWEC | 98 |
| 94 | c[E$_3$W$_4$C] | EWWWEWEC | 99 |
| 95 | c[E$_3$W$_4$C] | EWWWWEEC | 100 |
| 96 | c[E$_3$W$_4$C] | EWEEWWWC | 101 |
| 97 | c[E$_3$W$_4$C] | EWWEEWWC | 102 |
| 98 | c[E$_3$W$_4$C] | EWWWEEWC | 103 |
| 99 | c[E$_3$W$_4$C] | EWWWWEEC | 104 |
| 100 | c[E$_3$W$_4$C] | WEEEWWWC | 105 |
| 101 | c[E$_3$W$_4$C] | WWEEEWWC | 106 |
| 102 | c[E$_3$W$_4$C] | WWWEEEWC | 107 |
| 103 | c[E$_3$W$_4$C] | WWWWEEEC | 108 |
| 104 | c[E$_3$W$_4$C] | WEWEEWWC | 109 |
| 105 | c[E$_3$W$_4$C] | WEWWEEWC | 110 |
| 106 | c[E$_3$W$_4$C] | WEWWWEEC | 111 |
| 107 | c[E$_3$W$_4$] | EEEWWWW | 112 |
| 108 | c[E$_3$W$_4$] | EWEWWWE | 113 |
| 119 | c[E$_3$W$_4$] | EWWEWWE | 114 |
| 110 | c[E$_3$W$_4$] | EWWWEWE | 115 |
| 111 | c[E$_3$W$_4$] | EWWWWEE | 116 |
| 112 | c[E$_3$W$_4$] | EWEEWWW | 117 |
| 113 | c[E$_3$W$_4$] | EWWEEWW | 118 |
| 114 | c[E$_3$W$_4$] | EWWWEEW | 119 |
| 115 | c[E$_3$W$_4$] | EWWWWEE | 120 |
| 116 | c[E$_3$W$_4$] | WEEEWWW | 121 |

TABLE 3-continued provides additional non-limiting examples of peptide sequences.

| Cyclic Peptide | Circular Sequence | Linear Sequence | SEQ ID NO |
|---|---|---|---|
| 117 | c[$E_3W_4$] | WWEEEWW | 122 |
| 118 | c[$E_3W_4$] | WWWEEEW | 123 |
| 119 | c[$E_3W_4$] | WWWWEEE | 124 |
| 120 | c[$E_3W_4$] | WEWEEWW | 125 |
| 121 | c[$E_3W_4$] | WEWWEEW | 126 |
| 122 | c[$E_3W_4$] | WEWWWEE | 127 |
| 123 | c[$D_3W_4C$] | DDDWWWC | 128 |
| 124 | c[$D_3W_4C$] | DWDWWDC | 129 |
| 125 | c[$D_3W_4C$] | DWWDWDC | 130 |
| 126 | c[$D_3W_4C$] | DWWDWDC | 131 |
| 127 | c[$D_3W_4C$] | DWWWWDDC | 132 |
| 128 | c[$D_3W_4C$] | DWDDWWWC | 133 |
| 129 | c[$D_3W_4C$] | DWWDDWWC | 134 |
| 130 | c[$D_3W_4C$] | DWWWDDWC | 135 |
| 131 | c[$D_3W_4C$] | DWWWWDDC | 136 |
| 132 | c[$D_3W_4C$] | WDDDWWWC | 137 |
| 133 | c[$D_3W_4C$] | WWDDDWWC | 138 |
| 134 | c[$D_3W_4C$] | WWWDDDWC | 139 |
| 135 | c[$D_3W_4C$] | WWWWDDDC | 140 |
| 136 | c[$D_3W_4C$] | WDWDDWWC | 141 |
| 137 | c[$D_3W_4C$] | WDWWDDWC | 142 |
| 138 | c[$D_3W_4C$] | WDWWWDDC | 143 |
| 139 | c[$D_3W_4$] | DDDWWWW | 144 |
| 140 | c[$D_3W_4$] | DWDWWWD | 145 |
| 141 | c[$D_3W_4$] | DWWDWWD | 146 |
| 142 | c[$D_3W_4$] | DWWWDWD | 147 |
| 143 | c[$D_3W_4$] | DWWWWDD | 148 |
| 144 | c[$D_3W_4$] | DWDDWWW | 149 |
| 145 | c[$D_3W_4$] | DWWDDWW | 150 |
| 146 | c[$D_3W_4$] | DWWWDDW | 151 |
| 147 | c[$D_3W_4$] | DWWWWDD | 152 |
| 148 | c[$D_3W_4$] | WDDDWWW | 153 |
| 149 | c[$D_3W_4$] | WWDDDWW | 154 |
| 150 | c[$D_3W_4$] | WWWDDDW | 155 |
| 151 | c[$D_3W_4$] | WWWWDDD | 156 |
| 152 | c[$D_3W_4$] | WDWDDWW | 157 |
| 153 | c[$D_3W_4$] | WDWWDDW | 158 |
| 154 | c[$D_3W_4$] | WDWWWDD | 159 |

TABLE 3-continued provides additional non-limiting examples of peptide sequences.

| Cyclic Peptide | Circular Sequence | Linear Sequence | SEQ ID NO |
|---|---|---|---|
| 155 | c[Gla$_3$W$_4$] | GlaGlaGlaWWWW | 160 |
| 156 | c[Gla$_3$W$_4$] | GlaWGlaWWWGla | 161 |
| 157 | c[Gla$_3$W$_4$] | GlaWWGlaWWWGla | 162 |
| 158 | c[Gla$_3$W$_4$] | GlaWWWGlaWGla | 163 |
| 159 | c[Gla$_3$W$_4$] | GlaWWWWGlaGla | 164 |
| 160 | c[Gla$_3$W$_4$] | GlaWGlaGlaWWW | 165 |
| 161 | c[Gla$_3$W$_4$] | GlaWWGlaGlaWW | 166 |
| 162 | c[Gla$_3$W$_4$] | GlaWWWGlaGlaW | 167 |
| 163 | c[Gla$_3$W$_4$] | GlaWWWWGlaGla | 168 |
| 164 | c[Gla$_3$W$_4$] | WGlaGlaGlaWWW | 169 |
| 165 | c[Gla$_3$W$_4$] | WWGlaGlaGlaWW | 170 |
| 166 | c[Gla$_3$W$_4$] | WWWGlaGlaGlaW | 171 |
| 167 | c[Gla$_3$W$_4$] | WWWWGlaGlaGla | 172 |
| 168 | c[Gla$_3$W$_4$] | WGlaWGlaGlaWW | 173 |
| 169 | c[Gla$_3$W$_4$] | WGlaWWGlaGlaW | 174 |
| 170 | c[Gla$_3$W$_4$] | WGlaWWWGlaGla | 175 |
| 171 | c[(WE)$_3$WC] | WEWEWEWC | 176 |
| 172 | c[(EW)$_3$WC] | EWEWEWWC | 177 |
| 173 | c[(WD)$_3$WC] | WDWDWDWC | 178 |
| 174 | c[(DW)$_3$WC] | DWDWDWWC | 179 |
| 175 | c[(WGla)$_3$WC] | WGlaWGlaWDWC | 180 |
| 176 | c[(GlaW)$_3$WC] | DWDWDWDC | 181 |
| 177 | c[(WE)$_4$] | WEWEWEWE | 182 |
| 178 | c[(EW)$_4$] | EWEWEWEW | 183 |
| 179 | c[(WD)$_4$] | WDWDWDWD | 184 |
| 180 | c[(DW)$_4$] | DWDWDWDW | 185 |
| 181 | c[(WGla)$_4$] | WGlaWGlaWGlaWGla | 186 |
| 182 | c[(GlaW)$_4$] | GlaWGlaWGlaWGlaW | 187 |
| 183 | c[CW(EW)$_4$] | CWEWEWEWEW | 188 |
| 184 | c[(WGla)$_2$WDWC] | WGlaWGlaWDWC | 189 |
| 185 | c[(EW)$_3$EC] | EWEWEWEC | 190 |
| 186 | c[(DW)$_3$DC] | DWDWDWDC | 191 |
| 187 | c[E$_5$K]W$_5$C | Cyclic: EEEEEK<br>Tail: WWWWWC | 192 (cyclic portion), 220 (Tail) |
| 188 | c[E$_4$K]W$_5$C | Cyclic: EEEEK<br>Tail: WWWWWC | 193 (cyclic portion), 220 (Tail) |
| 189 | c[E$_5$K]W$_4$C | Cyclic: EEEEEK<br>Tail: WWWWC | 194 (cyclic portion), 221 (Tail) |

TABLE 3-continued provides additional non-limiting examples of peptide sequences.

| Cyclic Peptide | Circular Sequence | Linear Sequence | SEQ ID NO |
|---|---|---|---|
| 190 | c[E$_4$K]W$_4$C | Cyclic: EEEEK<br>Tail: WWWWC | 195 (cyclic portion), 221 (Tail) |
| 191 | c[E$_5$K]W$_5$ | Cyclic: EEEEEK<br>Tail: WWWWW | 196 (cyclic portion), 222 (Tail) |
| 192 | c[E$_4$K]W$_5$ | Cyclic: EEEEK<br>Tail: WWWWW | 197 (cyclic portion), 222 (Tail) |
| 193 | c[E$_5$K]W$_4$ | Cyclic: EEEEEK<br>Tail: WWWW | 198 (cyclic portion), 223 (Tail) |
| 194 | c[E$_4$K]W$_4$ | Cyclic: EEEEK<br>Tail: WWWW | 199 (cyclic portion), 223 (Tail) |
| 195 | c[D$_5$K]W$_5$C | Cyclic: DDDDDK<br>Tail: WWWWWC | 200 (cyclic portion), 220 (Tail) |
| 196 | c[D$_4$K]W$_5$C | Cyclic: DDDDK<br>Tail: WWWWWC | 201 (cyclic portion), 220 (Tail) |
| 197 | c[D$_5$K]W$_4$C | Cyclic: DDDDDK<br>Tail: WWWWC | 202 (cyclic portion), 221 (Tail) |
| 198 | c[D$_4$K]W$_4$C | Cyclic: DDDDK<br>Tail: WWWWC | 203 (cyclic portion), 221 (Tail) |
| 199 | c[D$_5$K]W$_5$ | Cyclic: DDDDDK<br>Tail: WWWWW | 204 (cyclic portion), 222 (Tail) |
| 200 | c[D$_4$K]W$_5$ | Cyclic: DDDDK<br>Tail: WWWWW | 205 (cyclic portion), 222 (Tail) |
| 201 | c[D$_5$K]W$_4$ | Cyclic: DDDDDK<br>Tail: WWWW | 206 (cyclic portion), 223 (Tail) |
| 202 | c[D$_4$K]W$_4$ | Cyclic: DDDDK<br>Tail: WWWW | 207 (cyclic portion), 223 (Tail) |
| 203 | c[Gla$_5$K]W$_5$C | Cyclic: GlaGlaGlaGlaGlaK<br>Tail: WWWWWC | 208 (cyclic portion), 220 (Tail) |
| 204 | c[Gla$_4$K]W$_5$C | Cyclic: GlaGlaGlaGlaK<br>Tail: WWWWWC | 209 (cyclic portion), 220 (Tail) |
| 205 | c[Gla$_5$K]W$_4$C | Cyclic: GlaGlaGlaGlaGlaK<br>Tail: WWWWC | 210 (cyclic portion), 221 (Tail) |
| 206 | c[Gla$_4$K]W$_4$C | Cyclic: GlaGlaGlaGlaK<br>Tail: WWWWC | 211 (cyclic portion), 221 (Tail) |
| 207 | c[Gla$_5$K]W$_5$ | Cyclic: GlaGlaGlaGlaGlaK<br>Tail: WWWWW | 212 (cyclic portion), 222 (Tail) |
| 208 | c[Gla$_4$K]W$_5$ | Cyclic: GlaGlaGlaGlaK<br>Tail: WWWWW | 213 (cyclic portion), 222 (Tail) |

TABLE 3-continued provides additional non-limiting examples of peptide sequences.

| Cyclic Peptide | Circular Sequence | Linear Sequence | SEQ ID NO |
|---|---|---|---|
| 209 | c[Gla$_5$K]W$_4$ | Cyclic: GlaGlaGlaGlaGlaK<br>Tail: WWWW | 214 (cyclic portion), 223 (Tail) |
| 210 | c[Gla$_4$K]W$_4$ | Cyclic: GlaGlaGlaGlaK<br>Tail: WWWW | 215 (cyclic portion), 223 (Tail) |
| 211 | c[E$_5$W$_5$C] | EEEEEWWWWWC | 216 |
| 212 | c[E$_4$W$_4$C] | EEEEWWWWC | 217 |
| 213 | c[(WE)$_4$CW] | WEWEWEWECW | 218 |
| 214 | c[(WR)$_4$WC] | WRWRWRWRWC | 224 |

Non-Limiting Variants of Cyclic Peptides

Variants of the cyclic peptides exemplified or otherwise disclosed herein may be designed using substitution techniques that are well understood in the art. Neither the cyclic peptides exemplified herein nor the variants discussed below limit the full scope of the subject matter disclosed herein.

Aspects of the present subject matter relate to cyclic peptides that result from 1, 2, 3, 4, 5, 6, 7, 8, 9, 10 or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a residue in a cyclic peptide sequence (e.g., corresponding to a location relative to a SEQ ID NO disclosed herein) may be replaced with another amino acid residue from the same side chain family. In certain embodiments, conservative amino acid substitutions may be made using a natural amino acid or a non-natural amino acid.

Non-limiting examples of conservative amino acid substitutions are shown in Table 4:

TABLE 4

Exemplary Conservative Substitutions

| Original Residue | Exemplary Substitution |
|---|---|
| Ala (A) | val; leu; ile; gly |
| Arg (R) | lys |
| Asn (N) | gln; his |
| Asp (D) | glu; gla |
| Cys (C) | ser |
| Gln (Q) | asn; his |
| Glu (E) | asp; gla |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

TABLE 5

Coded and Exemplary Non-Coded Amino Acids

| no. | abbrev | name |
|---|---|---|
| 1 | Ala | Alanine |
| 2 | Arg | Arginine |
| 3 | Asn | Asparagine |
| 4 | Asp | Aspartic acid |
| 5 | Cys | Cysteine |
| 6 | Gln | Glutamine |
| 7 | Glu | Glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenylalanine |
| 15 | Pro | Proline |
| 16 | Ser | Serine |
| 17 | Thr | Threonine |
| 18 | Trp | Tryptophan |
| 19 | Tyr | Tyrosine |
| 20 | Val | Valine |
| 21 | Aad | alpha-aminoadipic acid |
| 22 | Acpa | Aminocaprylic acid |
| 23 | Aecys | (S)-2-aminoethyl-L-cysteine•HCl |
| 24 | Afa | aminophenylacetate |
| 25 | Aiba | -aminoiso-bytyric acid |
| 26 | Aile | Alloisoleucine |
| 27 | Alg | L-allylglycine |
| 28 | Aba | amlnobutyric acid |
| 29 | Aphe | p-aminophenylalanine |
| 30 | Bat | -alanine |
| 31 | Brphe | p-bromophenylalanine |

TABLE 5-continued

Coded and Exemplary Non-Coded Amino Acids

| no. | abbrev | name |
|---|---|---|
| 32 | Cha | cyclohexylalanine |
| 33 | Cit | Citrulline |
| 34 | Clala | -chloroalanine |
| 35 | Cie | Cycioleucine |
| 36 | Clphe | p-chiorophenylalanine |
| 37 | Cya | cysteic acid |
| 38 | Dab | 2,4-diamino-butyric acid |
| 39 | Dap | 2,3-diaminopropionic acid |
| 40 | Dhp | 3,4-dehydro-proline |
| 41 | Dhphe | 3,4-,dihydroxyphenylalanine |
| 42 | Fphe | p-fluorophenylalanine |
| 43 | Gaa | D-glucose-aminic acid |
| 44 | Gla | gamma-carboxyglutamic acid |
| 45 | Hag | Homo-arginine |
| 46 | Hlys | hydroxyl-lysine•HCl |
| 47 | Hnvl | DL-hydroxy norvaline |
| 48 | Hog | Homoglutamine |
| 49 | Hoph | homophenylalanine |
| 50 | Has | Homoserine |
| 51 | Hpr | hydroxyl- proline |
| 52 | Iphe | p-Iodopheny-lalanine |
| 53 | Ise | Isoserine |
| 54 | Mie | -methyl-leucine |
| 55 | Msmet | DL-methionine-s-methylsulfoniumchloride |
| 56 | 1Nala | 3-(1-naphthyl)alanine |
| 57 | 2Nala | 3-(2-naphthyl)alanine |
| 58 | Nle | norleucine (or 2-aminohexanoic acid) |
| 59 | Nmala | N-methyl-alanine |
| 60 | Nva | norvaline (or 2-aminopentanoic acid) |
| 61 | Obser | O-benzylserine |
| 62 | Obtyr | O-benzyl-tyrosine |
| 63 | Oetyr | O-ethyltyrosine |
| 64 | Omser | O-methylserine |
| 65 | Omthr | O-methy threonine |
| 66 | Omtyr | O-methyl-tyrosine |
| 67 | Orn | Ornithine |
| 68 | Pen | Penicillamine |
| 69 | Pga | pyroglutamic acid |
| 70 | Pip | pipecolic acid |
| 71 | Sar | Sarcosine |
| 72 | Tfa | 3,3,3-trifluoroalanine |
| 73 | Thphe | 6-hydroxydopa |
| 74 | Vig | L-vinylglycine |
| 75 | Aaspa | (-)-(2R)-2-amino-3-(2-aminoethylsulfonyl)propanoic acid dihydrochloride |
| 76 | Ahdna | (2S)-2-amino-9-hydroxy-4,7-dioxanonanolc acid |
| 77 | Ahoha | (2S)-2-amino-6-hydroxy-4-oxahexanoic acid |
| 78 | Ahsopa | (-)-(2R)-2-amino-3-(2-hydroxyethylsulfonyl)propanoic acid |
| 79 | 1MT | 1-methyl-tryptophan |

Substitutions with natural amino acids may alternatively or additionally be characterized using a BLOcks SUbstitution Matrix (a BLOSUM matrix). An example of a BLOSUM matrix is the BLOSUM62 matrix, which is described in Styczynski et al. (2008) "BLOSUM62 miscalculations improve search performance" Nat Biotech 26 (3): 274-275, the entire content of which is incorporated herein by reference. The BLOSUM62 matrix is shown in FIG. 17.

Substitutions scoring at least 4 on the BLOSUM62 matrix are referred to herein as "Class I substitutions"; substitutions scoring 3 on the BLOSUM62 matrix are referred to herein as "Class II substitutions"; substitutions scoring 2 or 1 on the BLOSUM62 matrix are referred to herein as "Class III substitutions"; substitutions scoring 0 or −1 on the BLOSUM62 matrix are referred to herein as "Class IV substitutions"; substitutions scoring −2, −3, or −4 on the BLOSUM62 matrix are referred to herein as "Class V substitutions."

Various embodiments of the subject application include cyclic peptides that having 1, 2, 3, 4, 5, 6, 7, 8, 9, 10 or more Class I, II, III, IV, or V substitutions compared to a cyclic peptide exemplified herein, or any 1, 2, 3, 4, 5, 6, 7, 8, 9, 10 or more of any combination of Class I, II, III, IV, and/or V substitutions compared to a cyclic peptide exemplified herein.

Aspects of the present subject matter also relate to cyclic peptides having 1, 2, 3, 4, 5, or more amino acid insertions or deletions compared to cyclic peptides exemplified herein.

D-Amino Acids

Of the standard a-amino acids, all but glycine can exist in either of two optical isomers, called L or D amino acids, which are mirror images of each other. While L-amino acids represent all of the amino acids found in proteins during translation in the ribosome, D-amino acids are found in some proteins produced by enzyme posttranslational modifications after translation and translocation to the endoplasmic reticulum. D amino acids are abundant components of the peptidoglycan cell walls of bacteria, and D-serine acts as a neurotransmitter in the brain. The L and D convention for amino acid configuration refers not to the optical activity of the amino acid itself, but rather to the optical activity of the isomer of glyceraldehyde from which that amino acid can be synthesized (D-glyceraldehyde is dextrorotary; L-glyceraldehyde is levorotary).

Cyclic peptides either fully or partially built of D-amino acids possess advantages over L-cyclic peptides. For example, D-cyclic peptides are biodegraded slower than their levorotary counterparts leading to enhanced activity and longer biological half lives (Sela and Zisman, 1997 FASEB J, 11: 449-456, incorporated herein by reference). Thus, the invention provides for the use of D-cyclic peptides in the methods described herein. For example, cyclic peptides comprise solely L-amino acids or solely D-amino acids, or a combination of both D-amino acids and L-amino acids.

Isotopes

Cyclic peptides optionally contain radioactive elements or stable isotopes, or a combination of both. Stable isotopes are chemical isotopes that may or may not be radioactive, but if radioactive, have half lives too long to be measured. Different isotopes of the same element (whether stable or unstable) have nearly the same chemical characteristics and therefore behave almost identically in biology (a notable exception is the isotopes of hydrogen). The mass differences, due to a difference in the number of neutrons, will result in partial separation of the light isotopes from the heavy isotopes during chemical reactions and during physical processes such as diffusion and vaporization. This process is called isotope fractionation. Examples of stable isotopes include oxygen, carbon, nitrogen, hydrogen and sulfur. Heavier stable isotopes include iron, copper, zinc, and molybdenum.

Gamma cameras are used in e.g. scintigraphy, SPECT and PET to detect regions of biologic activity that may be associated with disease. Relatively short lived isotope, such as $^{123}$I is administered to the patient.

Scintigraphy ("scint") is a form of diagnostic test wherein radioisotopes are taken internally, for example intravenously or orally. Then, gamma cameras capture and form two-dimensional images from the radiation emitted by the radiopharmaceuticals.

Single-photon emission computed tomography (SPECT) is a 3D tomographic technique that uses gamma camera data from many projections and can be reconstructed in different planes. A dual detector head gamma camera combined with a CT scanner, which provides localization of functional SPECT data, is termed a SPECT/CT camera, and has shown utility in advancing the field of molecular imaging. In SPECT imaging, the patient is injected with a radioisotope, most commonly Thallium $^{201}$TI, Technetium $^{99m}$TC, Iodine $^{123}$I, and Gallium $^{67}$Ga.

Positron emission tomography (PET) uses coincidence detection to image functional processes. Short-lived positron emitting isotope, such as $^{18}$F, is incorporated with an organic substance such as glucose, creating F18-fluorodeoxyglucose, which can be used as a marker of metabolic utilization. Images of activity distribution throughout the body can show rapidly growing tissue, like tumor, metastasis, or infection. PET images can be viewed in comparison to computed tomography scans to determine an anatomic correlate. Other radioisotopes used in nuclear medicine thallium-201, tellurium-123, cadmium-113, cobalt-60, and strontium-82.

Non-Amino Acid Backbones

Though cyclic peptides have a cyclical structure comprising amino acids linked by peptide bonds, cyclical polymers comprising monomers other than amino acids are possible. For example, amino acid side chains of cyclic peptides disclosed herein may be covalently bound to a cyclic homopolymer or cyclic heteropolymer backbone in which the monomers are linked by covalent bonds other than peptide bonds.

Cosmetic Compositions

Cosmetics are substances used to enhance the appearance or odor of the human body. Cosmetics include but are not limited to skin-care creams, lotions, powders, perfumes, lipsticks, eye and facial makeup, gels, deodorants, hand sanitizer, bath oils, bath salts, butters, temporary tattoos, body paints and stains, skin moisturizers, fingernail polishes, cleansing shampoos, permanent waves, and hair colors, as well as any substance intended for use as a component of a cosmetic product. A subset of cosmetics is called "make-up," which refers primarily to colored products intended to alter the user's appearance. The U.S. Federal Food, Drug, and Cosmetic Act defines cosmetics by their intended use, as "articles intended to be rubbed, poured, sprinkled, or sprayed on, introduced into, or otherwise applied to the human body . . . for cleansing, beautifying, promoting attractiveness, or altering the appearance." The European Commission defines a cosmetic product as any substance or mixture intended to be placed in contact with the external parts of the human body (epidermis, hair system, nails, lips and external genital organs) or with the teeth and the mucous membranes of the oral cavity with a view exclusively or mainly to cleaning them, perfuming them, changing their appearance, protecting them, keeping them in good condition or correcting body odors. Each of these definitions is exemplary and should not be interpreted as limiting the scope of the subject matter disclosed herein. However, in certain embodiments, a cosmetic is defined as by the U.S. Federal Food, Drug, and Cosmetic Act and/or the European Commission.

In certain embodiments, a cosmetic composition of the present invention includes a colorant. As used herein, "colorant" includes substances which are exclusively or mainly intended to color a cosmetic product, or the body as a whole or certain parts thereof, by absorption or reflection of visible light. Precursors of oxidative hair colorants are also colorants. Non-limiting examples of colorants include pigments and dyes. Colorants may include, e.g., organic or inorganic substances. Examples of useful inorganic pigments include iron oxides (yellow, red, brown or black), ferric ammonium ferrocyanide (blue), manganese violet, ultramarine blue, chrome oxide(green), talc, lecithin modified talc, zeolite, kaolin, lecithin modified kaolin, titanium dioxide(white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Polymeric colorants include nylon powder, polyethylene, and polyesters. The polyesters can include linear, thermoplastic, crystalline or amorphous materials produced using one or more diols and one or more dicarboxylic acids copolymerized with colorants. An exemplary list of cosmetically acceptable colorants can be found in the International Cosmetic Ingredient Dictionary and Handbook, 7th Edition, CTFA, 1997, pp. 1628-1630, the contents of which are incorporated herein by reference. In some embodiments, a colorant constitutes from about 0.1% to about 30% by weight of a cosmetic composition.

Accordingly, the cosmetic compositions described herein include various skin care products. These include creams and lotions to moisturize the face and body which are typically formulated for different skin types, and treatment products to repair or hide skin imperfections (acne, wrinkles, dark circles under eyes, etc.). For each skin type, the correct types of products must be used in order to maintain healthy and attractive skin. Regular use of a suitable moisturizer benefits the skin, as it hydrates and prevents the dehydration of skin. Thus, the compositions described herein protect the skin against the drying influences of the environment, including the harsh effects of the sun, cold and heat. Oil free moisturizers are utilized for oily skins. Types of moisturizers include oil-in water emulsions and water-in -oil emulsions. For normal and combination skin, a water based moisturizer containing minimal oil is suitable. Sensitive and dry types of skin require moisturizers containing a high content of oil.

When used in a skin treatment product, cyclic peptides may comprise as cargo or be added together with skin care treatment actives, such as those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, antiaging agents, antiwrinkle agents, antiasthmatic agents and bronchodilators, sunscreen agents, antihistamine agents, skin lightening agents, depigmenting agents, wound-healing agents, vitamins, corticosteroids, self-tanning agents, or hormones. The amount of active agent to be used in any given formulation is readily determined in accordance with its usual dosage.

In some embodiments, a cyclic peptide comprises cargo that the cyclic peptide does not translocate across lipid bilayers, such as those of skin cell membranes. In such embodiments, the cyclic peptide promotes or increases the attachment of the cargo to the surface of the skin without delivering the cargo into cells. In various convenient embodiments, such cyclic peptides and the cargo thereof may be washed way using a solution having a nonacidic pH.

In various embodiments, cosmetic compositions described herein include natural or organic ingredients. All natural products contain mineral and plant ingredients, while organic products are made with organic agricultural products.

Aspects of the present invention relate to a temporary tattoo comprising a cargo-linked cyclic peptide. In some embodiments, the cyclic peptide preferentially targets the cargo compound to the inner and/or the outer leaflet of membranes. Various embodiments relate to temporary tattoos that remain on the skin for days (e.g., at least about 1, 2, 3, 4, 5, 6, 7 days), weeks (e.g., at least about 1, 2, 3, or 4 weeks) or months (e.g., at least about 1, 2, 3, 4, 5, 6, 7, 8, 9, 10, 11, or 12 months). Non-limiting examples of cargo compounds that may be linked for cyclic peptides in temporary tattoos include dyes and pigments (a pigment compound used in permanent tattoos). For example, the cargo may be a red, green, black, white, yellow, orange, pink, grey, purple, or other color. Non-limiting examples of pigments include iron oxides (yellow, red, brown or black), ferric ammonium ferrocyanide (blue), manganese violet, ultramarine blue, chrome oxide(green), talc, lecithin modified talc, zeolite, kaolin, lecithin modified kaolin, titanium dioxide (white) and mixtures thereof. Other useful pigments are pearlants such as mica, bismuth oxychloride and treated micas, such as titanated micas and lecithin modified micas. Additional non-limiting examples of coloring agents that may be linked to a cyclic peptide include heavy metals such as mercury (red); lead (yellow, green, white); cadmium (red, orange, yellow); nickel (black); zinc (yellow, white); chromium (green); cobalt (blue); aluminium (green, violet); titanium (white); copper (blue, green); iron (brown, red, black); and barium (white); metal oxides such as ferrocyanide and ferricyanide (yellow, red, green, blue); and organic chemicals such as azo-chemicals (orange, brown, yellow, green, violet) and naptha-derived chemicals (red). Additional elements used as pigments include but are not limited to antimony, arsenic, beryllium, calcium, lithium, selenium, and sulphur.

Various implementations of the present subject matter relate to methods and compositions using cyclic peptides as sunless tanning agents. In a non-limiting example, the cyclic peptide is linked to a carotenoid (e.g., a lycopene, beta-carotene or canthaxanthin), dihydroxyacetone (DHA), tyrosine, afamelanotide, Melanotan II (also known as (3S,6S,9R,12S,15S,23S)-15-[(N-Acetyl-L-norleucyllamino]-9-benzyl-6-(3-carbamimidamidopropyl)-12-(1H-imidazol-4-ylmethyl)-3-(1H-indol-3-ylmethyl)-2,5,8,11,14,17-hexaoxo-1,4,7,10,13,18-hexaazacyclotricosane-23-carboxamide), a retinoid, a melanocyte-stimulating hormone, forskolin, isobutylmethylxanthine, a diacylglycerol analogue, or cholera toxin. In some embodiments, the cargo is dihydroxyacetone (DHA). Various embodiments relate to methods for making the surface of skin appear darker for days (e.g., at least about 1, 2, 3, 4, 5, 6, 7 days), weeks (e.g., at least about 1, 2, 3, or 4 weeks) or months (e.g., at least about 1, 2, 3, 4, 5, 6, 7, 8, 9, 10, 11, or 12 months) after at least one (e.g., a single application) of a cyclic peptide of the present subject matter to the skin.

In certain embodiments, cyclic compounds that preferentially target cargo to an inner leaflet of a membrane are used to increase the length of time that the cyclic peptide is on the skin and/or to inhibit removal of the cyclic peptide from the surface of the skin, e.g., by rubbing, washing, or swimming.

Skin pH

Skin pH may vary, but the surface of skin is generally acidic. The natural pH of the surface of skin is thought to be under 6.0. See, e.g., Lambers et al. (2006) Int J Cosmet Sci. 2006 October; 28(5):359-70, the entire content of which is incorporated herein by reference. In various embodiments, a normal skin pH is considered to be a pH of about 4.5, 5.0, 5.5, 6.0, or 4.5-6.0. The cyclic peptides may be used to deliver cargo to acidic skin, e.g., to introduce a compound such as a cosmetic or pharmaceutical compound into a dermal cell of a subject. For example, the compound may be useful in balancing skin pH (e.g., to make the skin surface more or less acidic) or to treat a symptom or disease associated with abnormal pH (e.g., a pH less than about 4.5 or greater than about 6.0).

Skin pH is known to relate to various dermatological conditions. See, e.g., Ali and Yosipovitch (2013) Acta Derm Venereol, 93(3):261-7. When functioning properly, skin permeability barrier homeostasis imparts the skin with the capability of withstanding external insults and retaining hydration. Several dermatoses characterized by disruption of the permeability barrier have altered pH. Non-limiting examples include atopic dermatitis (e.g., eczema), diaper dermatitis, acne, and uremic pruritus. Dry and oily skin, as well as symptoms associated with such skin, may also result from or contribute to abnormal pH.

Dry skin may have an elevated pH compared to normal skin (e.g., having a pH of above about 6.0, 6.5 or 7.0). Oily skin is categorized as a reduced pH compared to normal skin (e.g., having a pH below about 4.5). The development of blemishes such as pimples and acne may result from or be exacerbated by low skin pH. Subjects with irritated/inflamed chronic conditions such as eczema and rosacea may have skin pH that is abnormally high or low.

Skin Treatment and Care

The cyclic peptides are used to deliver any cargo, e.g., peptides, nucleic acids, or small molecules into cells of the dermis and/or epidermis. Aspects of the present subject matter relate to treating normal skin (characterized by an acidic pH, i.e., lower than a pH of 7) or skin with lower than normal pH. In some embodiments, a symptom of a condition associated with low pH is treated, or the pH is increased without targeting a specific symptom or underlying condition. For example, methods, cyclic peptides, and compositions disclosed herein are useful for treating dermatitis, oily skin, oily skin patches, chronic and irritated skin, eczema, rosacea, acne, and pimples. For application of compositions containing cyclic peptides to dermal cells/tissues, e.g., application to skin, the compositions are typically in the form of a cream, lotion, serum, or emulsion.

In certain embodiments, methods, cyclic peptides, and compositions of the invention are used to treat dry skin. For example, a cyclic peptide may be conjugated to a compound that lowers pH such as an alpha hydroxy acid (AHA) (e.g., lactic acid or glycolic acid). In some embodiments, a subject in need of treatment for dry skin has a skin pH of at least about 6.5, 6.75, 7.0, or 7.5. Various implementations of the present subject matter relate to compositions for preventing or treating dry skin by lowering skin pH. For example, methods, cyclic peptides, and compositions disclosed herein are useful for treating chronic and irritated skin, eczema, and rosacea.

In certain embodiments, a cyclic peptide comprising an agent for delivery to skin is used irrespective of a condition's or subject's pH or typical pH. Thus, methods and cyclic peptides disclosed herein for use on skin are not limited uses involving a particular pH value.

Alpha hydroxy acids (AHAs) are a class of chemical compounds that consist of a carboxylic acid substituted with a hydroxyl group on the adjacent carbon. Non-limiting examples include glycolic acid, lactic acid, malic acid, citric acid, and tartaric acid. In various embodiments, a cyclic peptide comprises a cargo that is an AHA. Aspects of the present invention relate to the use of an AHA-conjugated cyclic peptide for balancing pH to a normal level, especially for the treatment of conditions associated with high pH. In various embodiments, a cyclic peptide conjugated to an AHA is used to exfoliate the skin, reduce visible signs of aging (such as wrinkles), and/or to moisturize the skin. In certain embodiments, a cyclic peptide is used instead of AHA.

In some embodiments, the cyclic peptide is conjugated to a beta hydroxyl acid (BHA; e.g., tropic acid), a polyhydroxy acid (PHA), a polyhydroxy bionic acid (PHBA), an aldobionic acid (BA), or a salicylic acid (SA). BHAs, PHAs, PHBAs, BAs, and SAs are described in Kornauser et al., (2010) Clinical, Cosmetic and Investigational Dermatology 3:135-142, the entire content of which is incorporated herein by reference. In some embodiments, a cyclic peptide linked to a SA is used as a keratolytic agent and/or to treat or reduce calluses, keratoses, acne, and/or photoaging. In various embodiments, a cyclic peptide linked to a PHA or a PHBA is used as a humectant and/or a moisturizer.

Certain implementations of the present subject matter provides sunscreen a composition comprising one or more cyclic peptides linked to one or more AHAs, SAs, and/or PHAs and/or one or more cyclic peptides linked to one or more of p-aminobenzoic acid, padimate O, phenylbenzimidazole sulfonic acid, 2-ethoxyethyl p-methoxycinnamate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium dioxide, 4-methylbenzylidene camphor, methylene bis-benzotriazolyl tetramethylbutylphenol, bis-ethylhexyloxyphenol methoxyphenol triazine, tris-biphenyl triazine, disodium phenyl dibenzimidazole tetrasulfonate, drometrizole trisiloxane, Sodium dihydroxy dimethoxy disulfobenzophenone, ethylhexyl triazone, diethylamino hydroxybenzoyl hexyl benzoate, diethylhexyl butamido triazone, dimethico-diethylbenzalmalonate, and/or isopentyl-4-methoxycinnamate. In various embodiments, a sunscreen comprising a cyclic peptide linked to a cargo compound is applied to the skin surface before exposure to direct sunlight is anticipated or while exposure to sunlight is occurring. The sunscreen may be in the form of, e.g., a lotion, cream, gel, spray, or other topical composition. In various embodiments, the cargo-linked cyclic peptide or cargo-linked cyclic peptide-containing sunscreen is water resistant, i.e., remains on the surface of skin even after the skin is exposed to or submerged in water (such as the water of a shower, bathtub, pool, pond, lake, stream, river, sea, or ocean). For example, a subject's skin may receive measurable protection from UV radiation from the cargo-linked cyclic peptide even after the subject's skin has been submerged in water for at least about 1, 2, 3, 4, 5, 10, or 30 minutes or about 1, 2, 3, or more hours after the sunscreen has been applied. In some embodiments, a cargo-linked cyclic peptide is added to a shampoo, conditioner, hair gel, mousse, or other hair product to protect the hair from UV radiation damage. Hair products such as a shampoo, conditioner, hair gel, and mousse containing a cyclic peptide are provided by the present subject matter. In certain embodiments, a lotion, cream, gel, spray, or other topical composition comprising a cyclic peptide is applied to the skin after sun exposure to reduce inflammation or damage caused by the sun exposure. Various aspects of the present invention relate to compositions and methods comprising a cyclic peptide for preventing a sunburn or preventing or delaying the onset of skin cancer, such as basal-cell cancer (BCC), squamous-cell cancer (SCC) and melanoma.

Aspects of the present subject matter relate to the treatment of acne. Cyclic peptide cargo compounds useful for treating acne include retinoids (e.g., retinoic acid, adapalene, isotretinoin, retinol, tazarotene, Retin A (tretinoin), vitamin A and vitamin A derivatives); antibiotics (e.g., clindamycin, erythromycin, metronidazole, sulfacetamide, and tetracyclines such as doxycycline and minocycline); spironolactone; isotretinoin; benzoyl peroxide; azelaic acid; salicylic acid; and nicotinamide.

Various implementations of the present subject matter relate to the treatment of eczema. Cyclic peptide cargo compounds useful for treating eczema include antihistamines (e.g., diphenhydramine); corticosteroids (e.g., hydrocortisone and clobetasol propionate); immunosuppresants (e.g., cyclosporin, azathioprine, and methotrexate); and immunomodulators (e.g., pimecrolimus and tacrolimus).

Aspects of the present invention relate to the treatment of scarred skin. In some embodiments, the cyclic peptide cargo minimizes formation of scar. Examples of such cargo include anti-fibrotic compounds such as (−)-epigallocatechin-3-gallate (EGCG) and interleukin-10 (IL-10). In various embodiments, the cyclic peptide cargo minimizes the appearance of, shrinks, softens, or reprograms fibrotic cells in an existing dermal scar. Cyclic peptide cargo compounds useful for treating existing scars include steroids (such as corticosteroids); Vitamin E; and Vitamin C.

Certain embodiments of the present subject matter relate to the treatment of psoriasis. Cyclic peptide cargo compounds useful for treating psoriasis include corticosteroids (e.g., hydrocortisone, desoximetasone, and clobetasol propionate); fluocinonide; Vitamin D and derivatives thereof (such as paricalcitol and calcipotriol); retinoids (e.g., retinoic acid, adapalene, isotretinoin, retinol, tazarotene, Retin A (tretinoin), vitamin A and vitamin A derivatives); methotrexate; ciclosporin; hydroxycarbamide; and fumarates (such as dimethyl fumarate).

Aspects of the present subject matter relate to reducing visible signs of skin aging, maintaining skin health, and promoting or maintaining the youthful appearance of skin. Cyclic peptides with cargo compounds that help balance the pH of skin at a normal level (e.g., a pH of about 4.5-6.0) are useful in such applications. As discussed above, the pH of skin may be balanced using an AHA cargo. Other agents useful for, e.g., reducing signs of aging (including fine lines, wrinkles, and dark spots) include moisturizing agents (e.g., hyaluronic acid and squalene); antioxidants (e.g., lipoic acid, propyl gallate, trolox, taxifolin, Vitamin C (especially in the form of L-ascorbic acid) and Vitamin E); anti-aging compounds (e.g., caffeine, lithium, metformin, buformin, phenformin, methionine sulfoximine, rapamycin, resveratrol, spermidine, and sodium nitroprusside); retinoids (e.g., retinoic acid, adapalene, isotretinoin, retinol, tazarotene, Retin A (tretinoin), vitamin A and vitamin A derivatives); coenzyme Q10; collagen; glycosaminoglycans; pentapeptides that increase collagen or glycosaminoglycan production (e.g., peptide formulas of the general sequence palmitoyl-lysyl-threonyl-lysyl-serine, palmitoyl tetrapeptide, palmitoyl tripeptide, palmitoyl oligopeptide, palmitoyl pentapeptide, which are described in U.S. Pat. Nos. 6,492,326; 6,620,419; and 8,025,907); hexapeptides that increase collagen production (e.g., acetyl glutamyl-glutamyl-methyonyl-glutamyl-arginyl-arginylamide, which is also known as acetyl hexapeptide-3 and is described in U.S. Patent Application No. 2008/0152606); and growth factors such as insulin-like growth factor 1 (IGF-1); transforming growth factor beta (TGF-Beta); granulocyte-macrophage colony-stimulating factor (GM-CSF); and platelet-derived growth factor (PDGF); epidermal growth factor (EGF); fibroblast growth factors (such as FGF1); and copper-pigment complexes (described in U.S. Patent Application No. 2007/0148222).

Additional compounds that may be applied to the skin include those useful in treating hair loss or promoting hair growth. Aspects of the present invention relate to cyclic peptides with a cargo compound that treats, reverses, reduces, or prevents hair loss. Non-limiting examples of compounds that prevent or reduce hair loss include vasodilators, 5-alpha-reductase inhibitors, finasteride, dutasteride, fluridil, spironolactone latanoprost, bimatoprost, minoxidil, tretinoin, ketoconazole, alfatradiol, topilutamide, and melatonin. A variety of hair loss conditions may be treated using methods and compositions of the present subject matter. For example, the hair loss may be androgenic alopecia, alopecia androgenetica, alopecia seborrheica, alopecia areata, alopecia totalis, alopecia universalis, trichotillomania, or hypotrichosis.

Cyclic peptides may also be used to deliver and/or target a chemotherapeutic agent to skin cancer at the surface of skin. For example, the skin cancer may be a melanoma tumor at the skin surface.

Chemotherapeutic Agents

Various chemotherapeutic agents may serve as cyclic peptide cargo compounds. Non-limiting examples include alkylating agents (such as nitrogen mustards, notrisoureas, alkyl sulfonates, triazines, ethylenimines, and platinum-based compounds); antimetabolites (such as 5-fluorouracil (5-FU), 6-mercaptopurine (6-MP), capecitabine (Xeloda®), cytarabine (Ara-C®), floxuridine, fludarabine, gemcitabine (Gemzar®), hydroxyurea, methotrexate, and pemetrexed (Alimta®)); topoisomerase inhibitors (e.g., topotecan, irinotecan, etoposide, and teniposide); taxanes (such as paclitaxel and docetaxel); platinum-based chemotherapeutics (such as cisplatin and carboplatin); anthracyclines (such as daunorubicin, doxorubicin (Adriamycin®), epirubicin, and idarubicin); epothilones (e.g., ixabepilone); vinca alkaloids (e.g., vinblastine (Velban®), vincristine (Oncovin®), and vinorelbine (Navelbine®)); estramustine; actinomycin-D; bleomycin; mitomycin-C; mitoxantrone; imatinib; lenalidomide; pemetrexed; bortezomib; leuprorelin; and abiraterone.

Antimicrobial Cargo Compounds

Various antimicrobial agents may serve as cyclic peptide cargo compounds. For example, the antimicrobial agent may be an antibacterial agent, an antifungal agent, or an antiprotozoal agent. In some embodiments, an antibacterial agent is also effective at killing fungi and/or protozoans, or slowing the growth thereof. In some embodiments, a composition comprising a cyclic peptide linked to an antimicrobial cargo is applied to the skin or a mucous membrane to prevent or control a microbial infection. In various embodiments, the infection is a bacterial or a fungal infection. In certain embodiments, the infection is a protozoan infection, such as leishmaniasis.

Non-limiting examples of microbial infections include diaper rashes, vaginal yeast infections, opportunistic skin infections, tineal fungal infections, superficial skin infections, acne, athlete's foot, thrush (candidiasis), and the like. In various embodiments, a cargo compound inhibits the growth of one or more microbe species selected from the group consisting of *Staphylococcus* species, *Streptococcus* species, *Pseudomonas* species, *Escherichia coli*, *Gardnerella vaginalis*, *Propionibacterium acnes*, *Blastomyces* species, *Pneumocystis carinii*, *Aeromonas hydrophilia*, *Trichosporon* species, *Aspergillus* species, *Proteus* species, *Acremonium* species, *Cryptococcus neoformans*, *Microsporum* species, *Aerobacter* species, *Clostridium* species, *Klebsiella* species, *Candida* species and *Trichophyton* species.

Non-limiting examples of antibacterial agents include penicillins (e.g., methicillin, nafcillin, oxacillin, cloxacillin, ampicillin, amoxicillin, pivampicillin, hetacillin, bacampicillin, metampicillin, talampicillin, epicillin, dicloxacillin, carbenicillin, ticarcillin, mezlocillin, piperacillin, penicillin G, and penicillin V); cephalosporins (e.g., cefaclor, cefonicid, cefprozil, cefuroxime, cefuzonam, cefmetazole, cefotetan, cefoxitin, cefacetrile, cefadroxil, cephalexin, cefaloglycin, cefalonium, cefaloridine, cefalotin, cefapirin, cefatrizine, cefazaflur, cefazedone, cefazolin, cefradine , cefroxadine, ceftezole, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefclidine, cefepime, cefluprenam, cefoselis, cefozopran, cefpirome, cefquinome ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin); carbapenems (e.g., meropenem, ertapenem, doripenem, biapenem, panipenem, betamipron); rifamycins (e.g., rifamycin B, rifamycin SV, rifampicin, rifabutin, rifapentine, and rifaximin); lipiarmycins (e.g., lipiarmycin B, fidaxomicin); quinolones (e.g., cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, nemonoxacin, delafloxacin, and prulifloxacin); sulfonamides (e.g., sulfacetamide, sulfadiazine, sulfadimidine, sulfafurazole, sulfisomidine, sulfadoxine, sulfamethoxazole, sulfamoxole, sulfanitran, sulfadimethoxine, sulfamethoxypyridazine, sulfametoxydiazine, sulfadoxine, and sulfametopyrazine); macrolides (e.g., azithromycin, clarithromycin, erythromycin, fidaxomicin, telithromycin, carbomycin A, josamycin, kitasamycin, midecamycin, midecamycin acetate, oleandomycin, solithromycin, spiramycin, troleandomycin, tylosin, tylocine, and roxithromycin); lincosamides (e.g., lincomycin and clindamycin); tetracyclines (e.g., tetracycline); aminoglycosides (e.g., streptomycin, kanamycin, amikacin, dibekacin, sisomicin, netilmicin, tobramycin, gentamicin, and neomycin); cyclic lipopeptides (such as daptomycin); glycylcyclines (such as tigecycline); oxazolidinones (such as linezolid); and lipiarmycins (such as fidaxomicin); arsphenamine; prontosil; trimethoprim (TMP); sulfamethoxazole (SMX); co-trimoxaxole (a combination of TMP and SMX); meclocycline; neomycin B, C, or E; poymyxin B; bacitracin; tazobactam; a combination of ceftolozane and tazobactam; ceftazidime; avibactam; a combination of ceftazidime and avibactam; ceftaroline; andavibactam; a combination of ceftaroline and andavibactam; imipenem; plazomicin; eravacycline; and brilacidin. In some embodiments, two or more cyclic peptides, each comprising a different antibiotic, are combined to deliver a combination of antibiotics to a site.

Non-limiting examples of antifungal agents include polyene antifungals (e.g., amphotericin B, candicidin, filipin, hamycin, natamycin, nystatin, and rimocidin); imidazoles (bifonazole, butoconazole, clotrimazole, econazole, fenticonazole, isoconazole, ketoconazole, luliconazole, miconazole, omoconazole, oxiconazole, sertaconazole, sulconazole, and tioconazole); triazoles (albaconazole, efinaconazole, epoxiconazole, fluconazole, isavuconazole, itraconazole, posaconazole, propiconazole, ravuconazole, terconazole, voriconazole); thiazoles (e.g., abafungin); allylamines (e.g., amorolfin, butenafine, naftifine, and terbinafine); echinocandins (e.g., anidulafungin, caspofungin, and micafungin); ciclopirox; 5-fluorocytosine; griseofulvin; haloprogin; tolnaftate, undecylenic acid, Crystal violet, and balsam of Peru.

Non-limiting examples of antiprotozoal agents include metronidazole, co-trimoxaxole, eflornithine, furazolidone, melarsoprol, metronidazole, ornidazole, paromomycin sulfate, pentamidine, pyrimethamine, tinidazole, and nifursemizone.

An antimicrobial composition can be formulated to be suitable for application in a variety of ways, for example in a cream for skin (e.g., ringworm or athlete's foot), in a wash for the mouth (e.g., oral thrush), in a douche for vaginal application (e.g., vaginitis), in a powder for chaffing (e.g., dermatitis), in a liquid for toe nails (e.g., tinea pedis), in a bath salt or bath powder for treating genital, foot or other tissue infections in a bath, and the like.

Cyclic Peptides without Cargo Compounds

Surprisingly, various cyclic peptides without a cargo compounds (i.e., cargoless cyclic peptides) are useful as active ingredients in cosmetic and dermatological applications.

The present subject matter provides methods and compositions comprising a cyclic peptide that is not conjugated to a cargo molecule. In various embodiments, the cyclic peptide does not comprise a cysteine, a homocysteine, a selenocysteine, or a homoselenocysteine. In some embodiments, the cyclic peptide does not have a non-amino acid functional group to which a cargo compound may be attached. In certain embodiments, the cyclic peptide does not comprise a free sulfhydryl (SH) or a free selenohydryl (SeH) group. In various embodiments, the cyclic peptide consists of naturally occurring and/or non-naturally occurring amino acids.

The present subject matter provides cyclic peptides with skin moisturization and/or skin re-surfacing properties similar or superior to hydroxy acids, such as alpha hydroxyl acids (AHAs), beta hydroxyl acids (BHAs), polyhydroxy acids (PHAs), aldobionic acids (BAs), polyhydroxy bionic acids (PHBAs), and salicylic acids (SAs). Hydroxy acids comprise carboxyl groups.

In various embodiments, a cargoless cyclic peptide comprises at least about 1, 2, 3, 4, 5, 6, 7, 8, 9, 10 or more carboxyl groups. For example, cyclic peptides of the present subject matter having only 1 carboxyl group but no cargo may be useful for a variety of cosmetic and dermatological uses. In certain embodiments, a cyclic peptide comprises 1, 2, 3, 4, 5, 6, 7, 8, 9, 10 or more naturally occurring or non-naturally occurring amino acids having one or more carboxyl groups. Naturally occurring amino acids comprising a carboxyl group include L-aspartic acid and L-glutamic acid residues. Non-natural amino acids comprising a carboxyl group include D-aspartic acid and D-glutamic acid. In various embodiments, a cyclic peptide comprises about 1, 2, 3, 4, 5, or more naturally or non-naturally occurring amino acids that each have more than one carboxyl group. For example, the cyclic peptide may comprise at least one amino acid residue that has 2, 3, 4, or more carboxyl groups. An example of a naturally occurring amino acid with two carboxyl groups is gamma-carboxyglutamic acid (GLA). Though GLA (also referred to as "Gla") is not a coded amino acid, it occurs naturally by post-translational modification. Non-limiting examples of cyclic peptides include cyclic peptides with 1, 2, 3, 4, 5, or more GLA residues.

AHAs are thought to reduce the concentration of $Ca^{2+}$ ions in the epidermis and remove $Ca^{2+}$ ions from cell adhesion molecules and complexes. This process causes a loss of $Ca^{2+}$ ions from the cadherins of desmosome and adherens junctions, disrupts cellular adhesions, and promotes exfoliation. See, e.g., Kornhauser et al., (2010) Clinical, Cosmetic and Investigational Dermatology, 3:135-142; and Wang (1999) Med Hypotheses, 53(5): 380-82, the entire content of each of which is incorporated herein by reference. Without wishing to be bound by any scientific theory, cyclic peptides of the present subject matter comprising at least one carboxyl group (regardless of whether the cyclic peptide is linked to a cargo molecule) may chelate $Ca^{2+}$ ions similarly to or to a greater degree than AHAs (e.g., at least 10%, 20%, 50%, 2-fold, 5-fold or more of the activity of an AHA). Thus, the present subject matter provides cargoless cyclic peptides useful for skin exfoliation.

Aspects of the present invention also relate to the use of cargoless cyclic peptides as active ingredients to treat, improve the appearance of, or otherwise reduce acne, ichthyosis, karatoses, warts, psoriasis, plaque psoriasis, photoaged skin, melasma, solar lentigines, postinflammatory hyperpigmentation, rough skin, discolored skin, calluses, keratosis, solar keratosis, wrinkles, and visible signs of aging. In some embodiments, a cyclic peptide is used as a moisturizer or a humectant or is present in a composition as a moisturizer or a humectant. The present subject matter also provides chemical peels comprising cyclic peptides and methods of using cyclic peptides as chemical peels, e.g., to remove a remove a surface layer of skin.

In various implementations of the present subject matter, a cyclic peptide is used to modify a skin cell, such as a fibroblast, a keratinocyte, a melanocyte, and/or a Langerhans cell. For example, the present disclosure provides methods and compositions for (i) increasing collagen and/or hyaluronic acid synthesis by a skin cell; (ii) increasing apoptosis of a skin cell; (iii) increasing cytokine (e.g., interleukin (IL)-1α) or vascular endothelial growth factor (VEGF) expression by a skin cell; (iv) reducing melanin expression by a skin cell; and (v) accelerating desquamation of skin cells. In various embodiments of these methods and compositions, a composition comprising a cyclic peptide is applied to the skin surface. In some embodiments, the cyclic peptide increases collagen synthesis by a fibroblast. In certain embodiments, the cyclic peptide increases the release of at least one cytokine by a keratinocyte. In various embodiments, the cyclic peptide increases apoptosis of a keratinocyte. In some embodiments, the cyclic peptide increases VEGF expression by a keratinocyte. In various embodiments, the cyclic peptide reduces melanin expression by a melanocyte.

The present subject matter also provides methods and compositions comprising a cyclic peptide for reducing the presence of free radicals on the skin surface. In various embodiments, the free radical is a reactive oxygen species. Non-limiting examples of free radicals include superoxide ($O_2^-$), hydrogen peroxide ($H_2O_2$), and peroxynitrite ($OONO^-$)

In some embodiments, a cyclic peptide is used as a chelating agent on the surface of skin. For example, the cyclic peptide may chelate a $Ca^{2+}$ ion.

Aspects of the present subject matter provide a cargoless cyclic peptide for protection against the detrimental effects of ultraviolet (UV) radiation. For example, the cyclic peptide may be present in a composition that prevents UV damage to skin and/or that reduces the effects of UV damage to skin. In some embodiments, the cyclic peptide absorbs, blocks, or reflects UV radiation. For example, the cyclic peptide may absorb, block, or reflect UVA radiation (UV radiation having a wavelength of 320-400 nanometers) and/or UVB radiation (UV radiation having a wavelength of 290 to 320 nm). In certain embodiments, the cyclic peptide reduces an erythemal response to UV radiation.

The present subject matter provides sunscreen compositions comprising one or more cyclic peptides. In various embodiments, a sunscreen comprising a cyclic peptide is applied to the skin surface before exposure to direct sunlight is anticipated or while exposure to sunlight is occurring. The sunscreen may be in the form of, e.g., a lotion, cream, gel, spray, or other topical composition. The concentration of cyclic peptide in the sunscreen may be adjusted to confer a desired level of protection from UV radiation. In various embodiments, the cyclic peptide or cyclic peptide-containing sunscreen is water resistant, i.e., remains on the surface of skin even after the skin is exposed to or submerged in water (such as the water of a shower, bathtub, pool, pond, lake, stream, river, sea, or ocean). For example, a subject's skin may receive measurable protection from UV radiation from the cyclic peptide even after the subject's skin has been submerged in water for at least about 1, 2, 3, 4, 5, 10, or 30 minutes or about 1, 2, 3, or more hours after the sunscreen has been applied. In some embodiments, a cyclic peptide is added to a shampoo, conditioner, hair gel, mousse, or other hair product to protect the hair from UV radiation damage. Hair products such as a shampoo, conditioner, hair gel, and mousse containing a cyclic peptide are provided by the present subject matter. In certain embodiments, a lotion, cream, gel, spray, or other topical composition comprising a cyclic peptide is applied to the skin after sun exposure to reduce inflammation or damage caused by the sun exposure. Various aspects of the present invention relate to compositions and methods comprising a cyclic peptide for preventing a sunburn or preventing or delaying the onset of skin cancer, such as BCC, SCC, and melanoma.

Aspects of the present subject matter also provide for the topical use of cyclic peptides to prevent or control a microbial infection. For example, a composition comprising a cyclic peptide is applied to the skin to prevent or control a microbial infection. In some embodiments, the infection may be a bacterial or a fungal (mycotic) infection. In some embodiments, the infection is a protozoan infection (e.g., leishmaniasis). Non-limiting examples of microbial infections include diaper rashes, vaginal yeast infections, opportunistic skin infections, tineal fungal infections, superficial skin infections, acne, athlete's foot, and the like. In various embodiments, a cyclic peptide inhibits the growth of one or more microbe species selected from the group consisting of *Staphylococcus* species, *Streptococcus* species, *Pseudomonas* species, *Escherichia coli*, *Gardnerella vaginalis*, *Propionibacterium acnes*, *Blastomyces* species, *Pneumocystis carinii*, *Aeromonas hydrophilia*, *Trichosporon* species, *Aspergillus* species, *Proteus* species, *Acremonium* species, *Cryptococcus neoformans*, *Microsporum* species, *Aerobacter* species, *Clostridium* species, *Klebsiella* species, *Candida* species and *Trichophyton* species.

Exemplary Formulations

In various embodiments, cyclic peptides may be in a carrier such as an emulsion, paste, cream, lotion, gel, oil, ointment, suspension, aerosol spray, powder, aerosol powder, or semi-solid formulation. In some embodiments, the carrier is other than water. In some embodiments, the composition comprises petroleum jelly. A cyclic peptide may comprise about 0.1% to about 80% by weight of the final composition, preferably 1% to 10% by weight, in a formulation suitable for topical administration. The compositions may also include, but are not limited to the inclusion of: known antioxidants (e.g., vitamin E); buffering agents; lubricants (e.g., synthetic or natural beeswax); sunscreens (e.g., para-aminobenzoic acid); and other cosmetic agents (e.g., coloring agents, fragrances, oils, essential oils, moisturizers or drying agents). These agents may be present in compositions without being linked to a cyclic peptide in the form of cargo. Thickening agents (e.g., polyvinylpyrrolidone, polyethylene glycol or carboxymethyicellulose) may also be added to the compositions.

Fragrances and essential oils are particularly suited for the compositions used in personal hygiene products and methods, and can include sea salts, herbs or herb extracts, fragrance oils from a large variety of plants or animals, and fragrances from a large variety of plants or animals, as are all well known. Exemplary fragrances useful in a composition of this invention include African violet, frankincense & myrrh, lavender, vanilla, gardenia, honeysuckle, sandalwood, musk, jasmine, lotus, orange blossom, patchouli, heather, magnolia, amber, rose, and the like fragrances. Exemplary oils, including essential or fragrant oils, include almond, aloe, amber, apple, apricot, bayberry, benzoin, cactus blossom, carnation, carrageenan, cedarwood, cinnamon, cloves, coconut, cedar, copal, Emu, eucalyptus, frangipani, frankincense and myrrh, gardenia, grapefruit, heather, herbs, honeysuckle, jasmine, jojoba, kelp, lavender, lemon, lilac, lotus, magnolia, mulberry, musk, myrrh, narcissus, orange blossom, patchouli, peach, pinon pine, plumeria, rose, rosemary, safflower, sage, sandalwood, spirulina, strawberry, vanilla, violet, wisteria, and oils.

In addition, the fragrances and essential oils can be provided in various bath salt and bath soap compositions. Salts and soaps are also well-known within the art and can include sea salts, desert salts, mineral salts, sodium sesquicarbonate, magnesium sulfate, and the like commonly used bath salts.

Fragrances, oils, and salts are well known in the art, can be obtained from a variety of natural and commercial sources, and are not considered to limiting to the present invention. Exemplary commercial sources include: Innovative Body Science (San Marcos, Calif.); Intercontinental Fragrances, Inc., (Houston, Tex.); Scentastics, Inc., (Brattleboro, Vt.); and Michael Giordano International, Inc., (North Miami, Fla.).

Chemicals used in the present compositions can be obtained from a variety of commercial sources, including Spectrum Quality Products, Inc. (Gardena, Calif.); Seltzer Chemicals, Inc., (Carlsbad, Calif.); and Jarchem Industries, Inc., (Newark, N.J.).

Antimicrobial compositions can be formulated to be suitable for application in a variety of ways, for example in a cream for skin (e.g., ringworm or athlete's foot), in a wash for the mouth (e.g., oral thrush), in a douche for vaginal application (e.g., vaginitis), in a powder for chaffing (e.g., dermatitis), in a liquid for toe nails (e.g., tinea pedis), in a bath salt or bath powder for treating genital, foot or other tissue infections in a bath, and the like. In various embodiments of the invention, there is provided a method of inhibiting growth of or a pathogenic microbe, including applying a cyclic peptide or a composition comprising a cyclic peptide to a solid surface, contacting the solid surface with the applied cyclic peptide thereon to skin or a mucous membrane of a mammal, and allowing the solid surface to contact the skin or mucous membrane for sufficient time to allow initiation of probiotic activity of the isolated bacteria to inhibit growth the pathogenic microbe adjacent to or on the skin or mucous membrane. In one embodiment, the applying step includes applying the composition to a diaper, pliable material for wiping skin or a mucous membrane, dermal patch, adhesive tape, absorbent pad, tampon or article of clothing. In another embodiment, the applying step includes impregnating the composition into a fibrous or non-fibrous solid matrix.

Cosmetic and Dermatological Systems

The present subject matter also provides cosmetic and dermatological systems useful for any of the purposes disclosed herein and methods of using the same. Such systems may comprise a first topical composition comprising a cyclic peptide and a second topical composition for removing the cyclic peptide from the surface of skin. The system may also include one or more implements for applying either topical composition to the skin, such as a cloth or sponge. In various embodiments, a composition comprising cyclic peptides may be removed with a composition having a pH of less than about 5.0, 4.5, 4.0, 3.5 or 3.5-5.0. In certain embodiments, a composition that increases the pH of the skin surface (e.g., a composition that raises the skin pH to about 7.0, 7.25, 7.5, 7.75, or 7.0-8.0) is used to wash cyclic peptides from the skin surface. In some embodiments, the composition is a personal cleaning product such as a wash, soap, or detergent. In some embodiments, the composition is a bath salt or bath bubble composition.

The term "topical" is broadly utilized herein to include both epidermal and/or skin surfaces, as well as mucosal surfaces of the body.

The present subject matter also discloses a system for each method described herein comprising a container comprising a label and a cyclic peptide-containing composition as described herein, wherein said label comprises instructions for use of the composition for the intended method.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The compositions and elements of the compositions (e.g., peptides, moieties, and other components of the compositions) described herein may be purified. For example, purified naturally-occurring, synthetically produced, or recombinant compounds, e.g., polypeptides, nucleic acids, small molecules, or other agents, are separated from compounds with which they exist in nature. Purified compounds are at least 60% by weight (dry weight) the compound of interest. Preferably, the preparation is at least 75%, more preferably at least 90%, and most preferably at least 99% or 100%, by weight the compound of interest. Purity is measured by any appropriate standard method, for example, by column chromatography, polyacrylamide gel electrophoresis, or HPLC analysis.

Various embodiments of the invention relate to cyclic peptides comprising "cargo" or a "moiety." Depending on context, the cargo/moiety or may be referred to by a name or characteristic of an unconjugated form of the cargo/moiety regardless of whether the cargo/moiety is conjugated to a cyclic peptide. For example, a small molecule known as "Small Molecule X" when in an unconjugated form may also be referred to herein as "Small Molecule X" when in a form that is bound to a cyclic peptide. Similarly, a "toxin" that is toxic only when free and unconjugated may still be referred to as a "toxin" when it is in a form that is bound to a cyclic peptide. In some embodiments, a cargo molecule is functional when free from a cyclic peptide (e.g., after release from a cyclic peptide, e.g., within a cell). In some embodiments, a cargo molecule is functional while still covalently linked to a cyclic peptide.

Cyclical pH-Responsive Membrane Peptides (Cyclic Peptides)

In embodiments, the invention features a compound that is a cyclical pH-triggered membrane peptide (cyclic peptide). In embodiments, a cyclic peptide comprises four or more (e.g., 4, 5, 6, 7, 8, 9, 10, 11, 12, 13, 14, 15, 16, 17, 18, 19, or 20) amino acids. In embodiments, a cyclic peptide comprises two or more amino acids that are non-polar amino acids (e.g., as described herein). In embodiments, a cyclic peptide comprises one or more amino acids that is a protonatable amino acid (e.g., as described herein).

In embodiments, a cyclic peptide has a higher affinity to a membrane lipid bilayer at a pH about 5.0 compared to a pH about 8.0.

In embodiments, a cyclic peptide comprises a functional group to which a cargo compound may be attached. In embodiments, the functional group is between two amino acids within a cyclic peptide. In embodiments, an amino acid of a cyclic peptidecomprises the functional group.

In embodiments, a cyclic peptide has a structure according to formula (A), $$c[(AA)_n] \qquad (A),$$

or a pharmaceutically acceptable salt thereof, wherein "c" denotes the cyclic nature of the peptide;

each AA independently represents an amino acid as described herein; and n is an integer of 4 to 20 (e.g., 4, 5, 6, 7, 8, 9, 10, 11, 12, 13, 14, 15, 16, 17, 18, 19, or 20).

In embodiments, the compound of formula (A) has a structure that is:

| | |
|---|---|
| $c[AA_1\text{-}AA_2\text{-}AA_3\text{-}AA_4]$; | Formula (A4) |
| $c[AA_1\text{-}AA_2\text{-}AA_3\text{-}AA_4\text{-}AA_5]$; | Formula (A5) |
| $c[AA_1\text{-}AA_2\text{-}AA_3\text{-}AA_4\text{-}AA_5\text{-}AA_6]$; | Formula (A6) |
| $c[AA_1\text{-}AA_2\text{-}AA_3\text{-}AA_4\text{-}AA_5\text{-}AA_6\text{-}AA_7]$; | Formula (A7) |
| $c[AA_1\text{-}AA_2\text{-}AA_3\text{-}AA_4\text{-}AA_5\text{-}AA_6\text{-}AA_7\text{-}AA_8]$; | Formula (A8) |
| $c[AA_1\text{-}AA_2\text{-}AA_3\text{-}AA_4\text{-}AA_5\text{-}AA_6\text{-}AA_7\text{-}AA_8\text{-}AA_9]$; | Formula (A9) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}]$; | Formula (A10) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}]$; | Formula (A11) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}]$; | Formula (A12) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}]$; | Formula (A13) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}]$; | Formula (A14) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}\text{-}AA_{15}]$; | Formula (A15) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}\text{-}AA_{15}\text{-}AA_{16}]$; | Formula (A16) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}\text{-}AA_{15}\text{-}AA_{16}\text{-}AA_{17}]$; | Formula (A17) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}\text{-}AA_{15}\text{-}AA_{16}\text{-}AA_{17}\text{-}AA_{18}]$; | Formula (A18) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}\text{-}AA_{15}\text{-}AA_{16}\text{-}AA_{17}\text{-}AA_{18}\text{-}AA_{19}]$; or | Formula (A19) |
| $c[AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}\text{-}AA_{13}\text{-}AA_{14}\text{-}AA_{15}\text{-}AA_{16}\text{-}AA_{17}\text{-}AA_{18}\text{-}AA_{19}\text{-}AA_{20}]$, | Formula (A20) | or a pharmaceutically acceptable salt thereof, wherein each of $AA_1$, $AA_2$, $AA_3$, $AA_4$, $AA_5$, $AA_6$, $AA_7$, $AA_8$, $AA_9$, $AA_{10}$, $AA_{11}$, $AA_{12}$, $AA_{13}$, $AA_{14}$, $AA_{15}$, $AA_{16}$, $AA_{17}$, $AA_{18}$, $AA_{19}$, and $AA_{20}$ is independently an amino acid.

In embodiments, a cyclic peptide as described herein (e.g., a compound of Formula (A) such as any one of Formulas (A4)-(A20)) has (a) at least 2 of the amino acids of a cyclic peptide are non-polar amino acids, and/or (b) at least 1 of the amino acids of a cyclic peptide is a protonatable amino acid.

In embodiments, a cyclic peptide has (c) a higher affinity to a membrane lipid bilayer at pH 5.0 compared to at pH 8.0.

Click Reactions

Compounds described herein (e.g., cyclic peptide) can include a covalent bond between the compound and a cargo compound. In embodiments, a covalent bond has been formed by a bio-orthogonal reaction such as cycloaddition reactions ("click" reactions). Exemplary bio-orthogonal reactions suitable for the preparation for such compounds are described in, e.g., Zheng et al., "Development of Bioorthogonal Reactions and Their Applications in Bioconjugation," *Molecules*, 2015, 20, 3190-3205. The diversity and commercial availability of peptide precursors are attractive for constructing the multifunctional entities described herein. Described herein are exemplary, non-limiting click reactions suitable for, e.g., the preparation of cyclic peptide compounds that include a covalent bond between the peptide and a cargo compound.

Huisgen Cycloadditions

A category of click reactions includes Huisgen 1,3-dipolar additions of acetylenes to azides. See, e.g., Scheme 1.

Scheme 1 cyclic peptide—$L^1$—≡≡≡—$R^1$ +

Compound A $N_3$—$L^2$—CARGO ⟶

Compound B (I-A)
cyclic peptide—$L^1$ triazole with CARGO—$L^2$ on N1, $R^1$ on C4 and/or (I-B)
cyclic peptide—$L^1$ triazole with CARGO—$L^2$ on N2, $R^1$ on C4

CARGO—$L^1$—≡≡≡—$R^1$ +

Compound A'

$N_3$—$L^2$—cyclic peptide ⟶

Compound B'

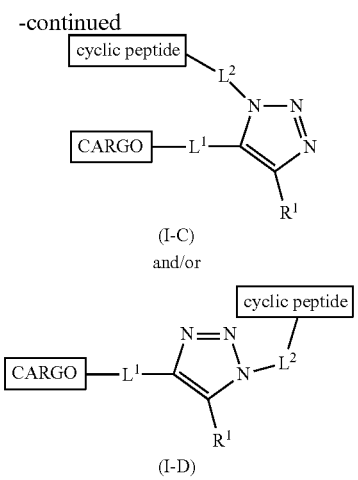

(I-C)

and/or (I-D)

In embodiments, cyclic peptide corresponds to any peptide described herein. In embodiments, CARGO corresponds to any cargo compound described herein.

In embodiments, $L^1$ is independently a bond, —$NR^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ combines with $R^1$ to form a substituted or unsubstituted 8-membered cycloalkynylene ring, or $L^1$ comprises one or more amino acids as described herein.

In embodiments, $R^1$ is hydrogen, substituted or unsubstituted alkyl, or $R^1$ combines with $L^1$ to form a substituted or unsubstituted 8-membered cycloalkynylene ring, or $L^1$ comprises one or more amino acids as described herein.

In embodiments, $L^1$ combines with $R^1$ to form a substituted or unsubstituted 8-membered cycloalkynylene ring. In embodiments, the 8-membered cycloalkynylene ring is unsubstituted. In embodiments, the 8-membered cycloalkynylene ring comprises two fluoro substitutents (e.g., a to the alkynyl).

In embodiments, $L^2$ is independently a bond, —$NR^B$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

In embodiments, each $R^A$ and $R^B$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the Huisgen cycloaddition is that described in Scheme 2 and Scheme 3.

Scheme 2

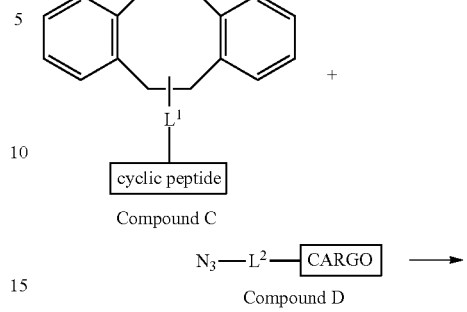

Compound C

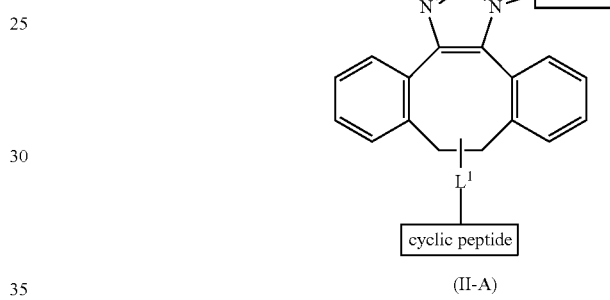

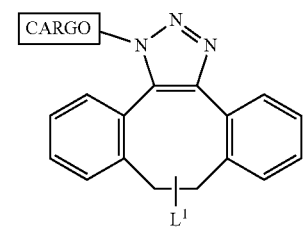

(II-A)

and/or (II-B)

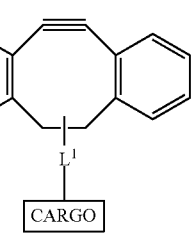

Compound C'

N₃—$L^2$—cyclic peptide

Compound D'

-continued

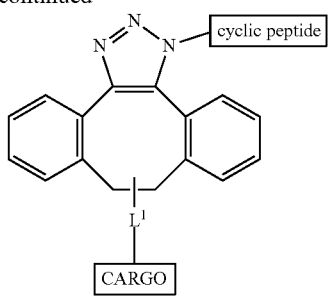

(II-C)

and/or

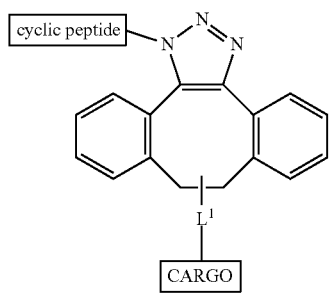

(II-D)

In embodiments, cyclic peptide corresponds to any peptide described herein. In embodiments, CARGO corresponds to any cargo compound described herein.

In embodiments, $L^1$ is independently a bond, —$NR^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, —$NR^B$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

Scheme 3

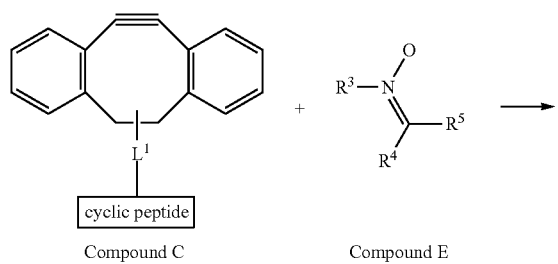

Compound C  Compound E

-continued

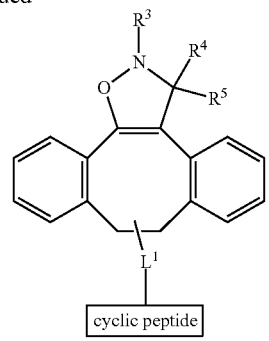

(III-A)

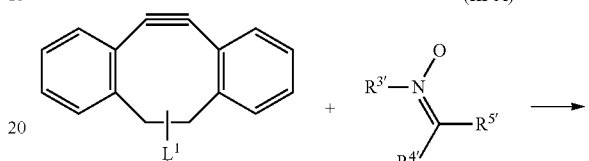

Compound C'  Compound E'

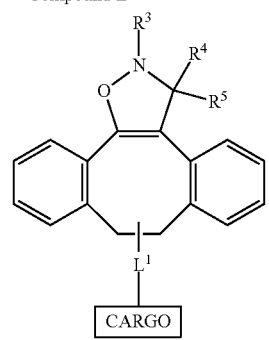

(III-B)

In embodiments, cyclic peptide corresponds to any peptide described herein. In embodiments, CARGO corresponds to any cargo compound described herein.

In embodiments, $L^1$ is independently a bond, —$NR^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, one of $R^3$, $R^4$, and $R^5$ is a cargo compound, and the other two variables are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, one of $R^{3'}$, $R^{4'}$, and $R^{5'}$ is a cyclic peptide compound, the other two variables are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Cycloadditions with Alkenes

In embodiments, certain activated alkenes (e.g., a strained alkene such as cis- or trans-cyclooctene or oxanorbornadiene), which may be represented as compound F or compound F', can undergo cycloaddition reactions with, e.g., an azide (Scheme 4), a tetrazine (Scheme 5), or a tetrazole (Scheme 6).

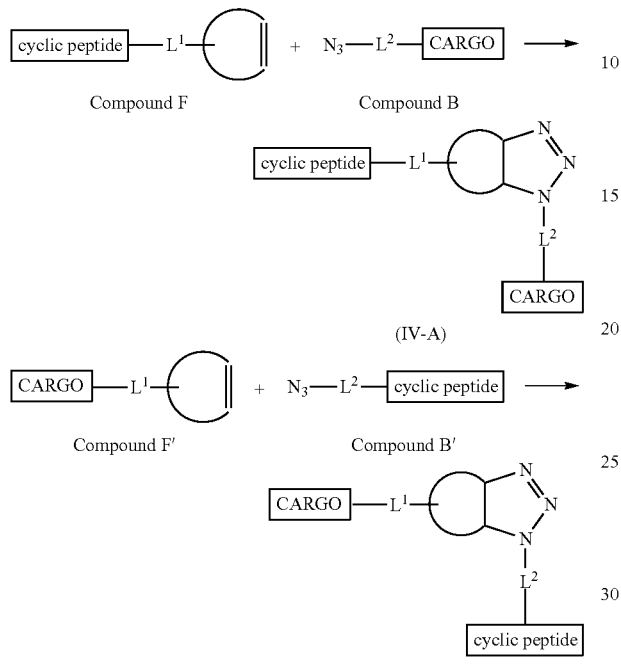

(IV-A)

(IV-B)

In embodiments, cyclic peptide corresponds to any peptide described herein. In embodiments, CARGO corresponds to any cargo compound described herein.

In embodiments, $L^1$ is independently a bond, —$NR^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, —$NR^B$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

Scheme 5

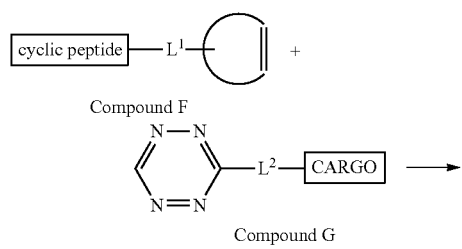

Compound F

Compound G

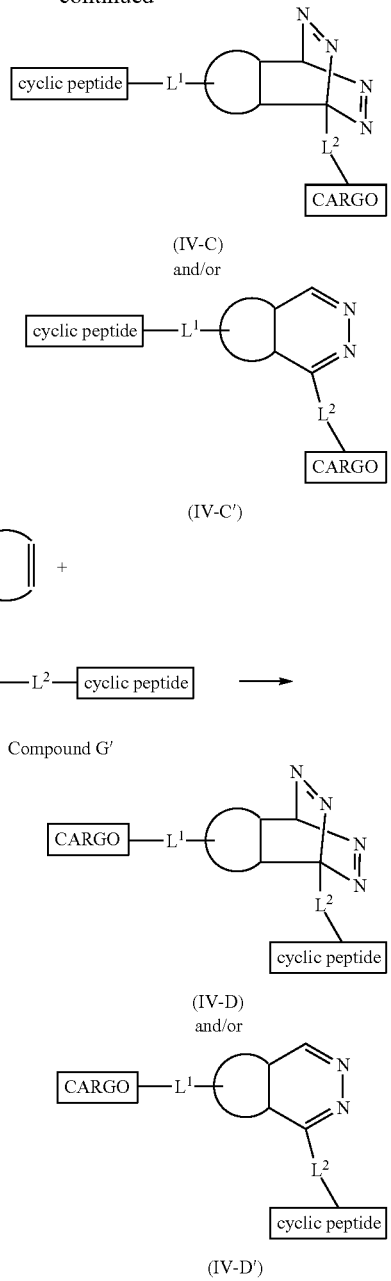

(IV-C)
and/or (IV-C')

Compound F'

Compound G'

(IV-D)
and/or (IV-D')

In embodiments, cyclic peptide corresponds to any peptide described herein. In embodiments, CARGO corresponds to any cargo compound described herein.

In embodiments, $L^1$ is independently a bond, —$NR^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, —$NR^B$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or L² comprises one or more amino acids as described herein.

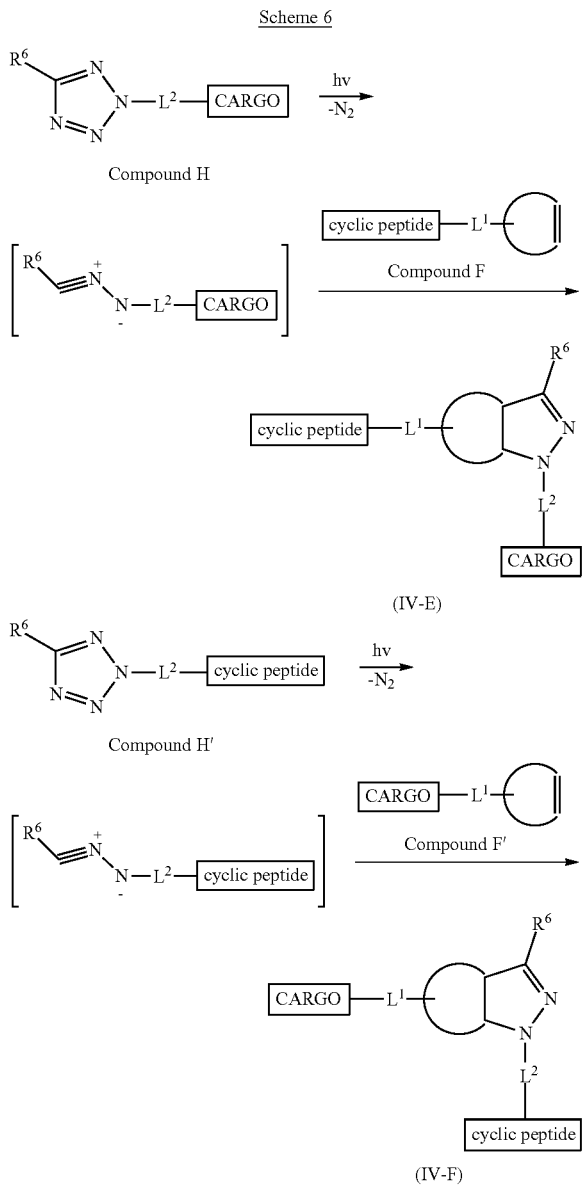

Scheme 6

(IV-E)

(IV-F)

In embodiments, cyclic peptide corresponds to any peptide described herein. In embodiments, CARGO corresponds to any cargo compound described herein.

In embodiments, L¹ is independently a bond, —NR$^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or L¹ comprises one or more amino acids as described herein.

In embodiments, L² is independently a bond, —NR$^B$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or L² comprises one or more amino acids as described herein.

In embodiments, R⁶ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the invention features any of the compounds described herein (e.g., any of Compounds A, A', B, B'; C, C', D, D', E, E', F, F', G, G'H, or H'; a compound according to any one of formulas (I-A), (I-B), (I-C), (I-D), (II-A), (II-B), (II-C), (II-D), (III-A), (III-B), (IV-A), (IV-B), (IV-C), (IV-C'), (IV-D), (IV-D'), (IV-E), or (IV-F); a compound according to Formula (A) such as any one of Formulas (A4)-(A20); or a compound according to any of SEQ ID NOS: 1-4); or a pharmaceutically acceptable salt thereof.

In embodiments, the invention features a composition (e.g., a pharmaceutical composition) comprising any of the compounds described herein (e.g., any of Compounds A, A', B, B'; C, C', D, D', E, E', F, F', G, G'H, or H'; a compound according to any one of formulas (I-A), (I-B), (I-C), (I-D), (II-A), (II-B), (II-C), (II-D), (III-A), (III-B), (IV-A), (IV-B), (IV-C), (IV-C'), (IV-D), (IV-D'), (IV-E), or (IV-F); a compound according to Formula (A) such as any one of Formulas (A4)-(A20); or a compound according to any of SEQ ID NOS: 1-4); or a pharmaceutically acceptable salt thereof.

The term "alkyl," by itself or as part of another substituent, means, unless otherwise stated, a non-cyclic straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom (e.g. selected from the group consisting of O, N, P, S, Se and Si, and wherein the nitrogen, selenium, and sulfur atoms may optionally be oxidized, and the nitrogen heteroatom may optionally be quaternized). The heteroatom(s) O, N, P, S, Se, and Si may be placed at any interior position of the heteroalkyl group or at the position at which the alkyl group is attached to the remainder of the molecule. Examples include, but are not limited to: —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH=CH—O—CH₃, —Si(CH₃)₃, —CH₂—CH=N—OCH₃, —CH=CH—N(CH₃)—CH₃, —O—CH₃, —O—CH₂—CH₃, and —CN. Up to two heteroatoms may be consecutive, such as, for example, —CH₂—NH—OCH₃.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NRR", —OR', —SeR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. selected from N, O, and S, wherein the nitrogen and sulfur atoms are optionally oxidized, and the nitrogen atom(s) are optionally quaternized). Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN, and —NO₂ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN, —NO₂, —R', —N₃, —CH(Ph)₂, fluoro(C₁-C₄)alkoxy, and fluoro(C₁-C₄)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

As used herein, the terms "heteroatom" or "ring heteroatom" are meant to include oxygen (O), nitrogen (N), sulfur (S), phosphorus (P), and silicon (Si).

Linear Peptides

The present disclosure provides linear counterparts of the cyclic peptide disclosed herein. Thus, this disclosure describes short linear peptides having a stretch of consecutive amino acids in a sequence that is the same as the sequence of consecutive amino acids in any cyclic peptide disclosed herein. Linear peptides other than counterparts of the cyclic peptides are also provided.

Linear peptides disclosed herein are short (i.e., have less than 19 amino acids) and either do not form helixes at low pH (e.g., at a pH less than 7.0) or form helixes that are substantially too short to extend through an entire lipid bilayer, e.g., a cell membrane lipid bilayer. In some embodiments, a short linear peptide comprises a stretch of less than 15 amino acids. For example, a short linear peptide may comprise a stretch of 13, 12, 11, 10, 9, 8, 7, 6, 5, or 4 amino acids. In various embodiments, a short linear peptide comprises at least 4 amino acids, e.g., 4-12, 4-11, 4-10, or 4-9 amino acids. In certain embodiments, a short linear peptide comprises 4 to 13 amino acids, e.g., 8 to 13 amino acids, 8 to 12 amino acids, 8 to 11 amino acids, or 8 to 10 amino acids. In some embodiments, a short linear peptide comprises at least 4 but less than 8, 9, 10, 11, 12, 13, 14, or 15 amino acids. In various embodiments, a short linear peptide comprises less than 13 or 12 amino acids, or 13 or 12 or less amino acids. In certain embodiments, a short linear peptide comprises less than 10 amino acids or 10 or less amino acids. The linear peptides may also include one or more aromatic residues that facilitate association with membranes.

Short linear peptides of the present invention are able to target lipid bilayer of membrane and translocate cargo from the outer leaflet of a membrane to the inner leaflet (and, e.g., the cytoplasm) in the absence of a conformational change into a helix. Energy is released when a peptide forms a helix in a membrane, and this energy release has been thought to help non-pore-forming peptides translocate cargo across lipid bilayers. See, e.g., U.S. Patent Application Publication No. 2015/0051153, published Feb. 19, 2015, the entire content of which is incorporated herein by reference.

In various implementations, a linear peptide may substantially translocate from the outer leaflet of a membrane to an inner leaflet of a membrane at a pH of about 7.0, 6.5, 6.0 or less. In some examples, a translocated linear peptide remains substantially at the inner leaflet of the membrane, even if the pH is increased after translocation. In some embodiments, a proportion of linear peptides move to the inner leaflet of a membrane such that substantially no part of the peptides remains in the extracellular space and/or in or on the outer leaflet.

An example of a linear peptide that has been made and tested is l(CW(EW)₄), which has the following sequence: CWEWEWEWEW (SEQ ID NO: 188).

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

EXAMPLE 1 pH-Sensitive Cyclic Peptides for Intracellular Delivery of Cargo Molecules and Targeting Acidic Tissue A series of cyclic peptides containing a number of tryptophan (W) and glutamic acid (E) residues were synthesized and evaluated as pH-sensitive tumor targeting agents. Biophysical studies revealed the molecular mechanism of peptides action and localization within the lipid bilayer at high and low pHs. The symmetric, c[(WE)$_4$WC] (SEQ ID NO: 2), and asymmetric, c[E$_4$W$_5$C] (SEQ ID NO: 5), cyclic peptides translocated amanitin, a polar cargo molecule of similar size, across the lipid bilayer and induced cell death in a pH- and concentration-dependent manner Fluorescently-labeled peptides were evaluated for targeting of acidic 4T1 mammary tumors in mice. The highest tumor to muscle ratio (5.6) was established for asymmetric cyclic peptide, c[E$_4$W$_5$C] (SEQ ID NO: 5), at 24 h after intravenous administration. The pH-insensitive peptide c[R$_4$W$_5$C] (SEQ ID NO: 219) did not exhibit tumor targeting. The data show that cyclic peptides containing tryptophan and glutamic acid are useful as a new class of pH-sensitive cellular delivery and tumor targeting tools.

pH is especially lower in the vicinity of the membrane of cancer cells due to the work of proton pumps, lactate export and CAIX/CAXII. Also, the pK for the protonation of Asp and Glu residues is higher (pK~6-7) near the surface of the hydrophobic membrane compared to bulk aqueous solution, where the pK~3-4 (Petkova et al. (1999) *Biochemistry* 38(5):1562-1572; 6. Harris T K & Turner G J (2002) *IUBMB Life* 53(2):85-98; Johansson A C & Lindahl E (2006) *Biophys J* 91(12):4450-4463; Karabadzhak et al. (2012) *Biophys J* 102(8):1846-1855). The most effective pH-sensitive tumor targeting agents should sense pH at the surface of cancer cells, where it is expected to be the lowest. There are a number of approaches under development for delivery of imaging and therapeutic agents to diseased tissue in a pH-dependent manner. They are based on the use of pH-sensitive polymers, liposomes, nanoparticles and small molecules (Karanth H & Murthy R S (2007) *J Pharm Pharmacol* 59(4):469-48; Chu et al., (1990) *Pharm Res* 7(8):824-834; Subbarao et al. (1987) *Biochemistry* 26(11): 2964-2972; Poon et al. (2011) *ACS Nano* 5(6):4284-4292; Okada et al. (2014) *Adv Mater* 26(19):2989-2992; Liu K C & Yeo Y (2013) *Mol Pharm* 10(5):1695-1704; Nwe et al. (2013) *J Med Chem* 56(20):7862-7869). Among peptides, family of pHLIPs, linear peptides of 25-35 residues, which insert into cellular membrane and form transmembrane helices are used for targeting of acidic tumors of various origins and other acidic diseased tissues (Andreev et al. (2014) *Front Physiol* 5:97; Weerakkody et al. (2013) *Proc Natl Acad Sci USA* 110(15):5834-5839). Application of cyclic peptides in biological sciences has become a subject of major interest because of their enhanced enzymatic stability versus linear peptides (Katsara et al. (2006) *Curr Med Chem* 13(19):2221-2232).

pH-sensitive negatively charged cyclic peptides were designed and their interactions with the lipid bilayer of liposomal and cellular membranes were studied in vitro and in vivo.

Methods

Materials

The peptide synthesis materials including Fmoc-L-amino acid building blocks, preloaded amino acids on 2-chlorotrityl resin as the solid support, and 2-(1H-benzotriazol-1-yl)-1,1,3,3-tetramethyluronium hexafluorophosphate (HBTU) used for coupling reagents were purchased from Chem-Impex Int'l Inc., Wood Dale, Ill. Piperidine and N-methylmorpholine were purchased from Sigma-Aldrich Chemical Co. (Milwaukee, Wis.). The other chemicals such as N,N-diisopropylethylamine (DIPEA), cleavage cocktail reagents trifluoroacetic acid (TFA), 1-hydroxy-7-azabenzotriazole (HOAt), N,N'-diisopropylcarbodiimide (DIC), acetic acid (AcOH), 2,2,2-trifluoroethanol (TFE), anisole, thioanisole, ethanedithiol (EDT), and anhydrous solvents such as NN-dimethylformamide (DMF), dichloromethane (DCM), hexane, acetic acid (AcOH), and 2,2,2-trifluoroethanol (TFE) were purchased from Fisher Scientific, Pittsburg, Pa.

Methodology of Peptide Synthesis

A linear protected peptide was first assembled. Direct cleavage of peptide-attached resin in the presence of AcOH/TFE/DCM (1:2:7 v/v/v) generated the linear peptide. Cyclization in dilute condition using DIC/HOAt in DMF/DCM solution for 12 h, followed by the deprotection of the side chain by using cleavage cocktail (TFA:thioanisole:anisole:EDT (90:5:2:3 v/v/v/v) afforded the cyclic peptide. The peptides were synthesized by employing the N-(9-fluorenyl) methoxycarbonyl (Fmoc)-solid phase chemistry using PS3 automated peptide synthesizer (Rainin Instrument Co., Inc.) at room temperature. The peptide sequence was assembled on preloaded amino acid on 2-chlorotriyl resin using coupling, activating, and deprotecting reagents using HBTU, N-methylmorpholine (0.4 M), and piperidine in DMF (20% v/v), respectively. The amino acids in the peptide sequence were coupled using coupling reagents and activating reagent in DMF for 1 h followed by washing with DMF 3 times. The deprotection was carried using piperidine (20%, v/v) in DMF for 2 times, 10 minute for each time, followed by washing with DMF (3 times). The appropriate sequence of linear protected peptide was assembled using the synthesizer. N- to C-terminal cyclization of peptide were achieved by cleavage of protected peptidyl resin by stirring the peptidyl resin in freshly prepared cleavage cocktail of AcOH/TFE/DCM (1:2:7, v/v/v) for 1 h at room temperature followed by washing the resin with TFE:DCM (2:8 v/v, 2 times). The collected filtrate was evaporated using a rotary evaporator followed by azeotropic removal of acetic acid by addition of hexane and dichloromethane to afford high viscous liquid or solid-protected linear peptide. The crude linear protected peptide was dissolved in excess of solvents DMF:DCM (4:1 v/v) followed by the addition of HOAt/DIC (1:1.1 equiv) for cyclization for 12-48 h confirmed by MALDI TOF-TOF mass spectrometry. The solvent was evaporated under high reduced pressure in a rotatory evaporator at 40-45° C. to remove DMF. The final cleavage of side chain protection from the peptide were carried out after confirming the peptide cyclization by MALDI mass spectrometer data by shaking the cyclized peptide mixture in cleavage cocktail reagent R (TFA/thioanisole/anisole/EDT (90:5:2:3 v/v/v/v, 10-15 mL) for 2-4 h followed by precipitation of peptide using cold ether, centrifugation at 2500 rpm and washing with excess of cold ether at 25° C. for 5 min. The crude peptide was purified with semi preparative reversed phase high performance liquid chromatography (RP-HPLC) by using Hitachi L-2455 on a C18 Phenomenex Prodigy reversed-phase column (10 μm, 250 cm×21.2 cm). The pure peptide was eluted at 15.0 mL/min using a gradient of binary solvent system using water and acetonitrile with 0.1% TFA for 0-100% over 60 min. The pure collected peptide fractions were pooled and lyophilized to provide solid powder in purity of ≥98%. All peptides were characterized by using high resolution time of flight AXIMA-performance MALDI TOF-TOF mass spectrometer (Shimadzu). The above mentioned protocol was applied for the synthesis of all cyclic peptides. As representative examples, the synthesis of cyclic, c[(WE)$_4$WC] (SEQ ID NO: 2), and linear, l(CW(EW)$_4$) (SEQ ID NO: 188), peptides is described here and provided in Scheme 51, respectively.

Synthesis of Cyclic Peptides

The linear peptide sequence was synthesized on PS3 automated synthesizer as described above in the scale of 0.3 mmol. H-Trp(Boc)-2-chlorotrityl resin (384.6 mg, 0.3 mmol, 0.78 mmol/g) was swelled in DMF, followed by coupling and deprotection cycles to assemble respective amino acids on the peptidyl resin using respective amino acids, such as Fmoc-Glu(OtBu)-OH (382.9 mg, 0.9 mmol), Fmoc-Trp(Boc)-OH (473.9 mg, 0.9 mmol), Fmoc-Cys(Trt)-OH (527.1 mg, 0.9 mmol), and HBTU (341 mg, 0.9 mmol) as the coupling reagent (Scheme S1). Fmoc group of N-terminal in the peptidyl resin was removed using deprotection cycle, and the resin was transferred to 100 ml round bottom flask. The linear protected peptide was cleaved by shaking peptidyl resin in cleavage cocktail AcOH/TFE/DCM (1:2:7 v/v/v, 50 ml) for 1 h followed by washing the resin using TFE:DCM (2:8 v/v, 10 mL, 2 times). The combined filtrate was evaporated to dryness with the subsequently addition of hexane (50 mL×3) and DCM (10 mL×3) to remove acetic acid, which provided solid white crude protected peptide ready for cyclization. The cyclization was carried out by dissolving the solid peptide in anhydrous DMF/DCM (250 mL, 4:1 v/v) under nitrogen using DIC (155.0 μL, 0.99 mmol) and HOAt (122.5 mg, 0.9 mmol) with stirring at room temperature for 24 h. The cyclized product was confirmed by taking small aliquot of the reaction mixture and cleavage with reagent R and using MALDI. After cyclization was confirmed, the solvents were evaporated under high reduced pressure, and the side chain protections were removed by addition of cleavage cocktail of reagent R, TFA/thioanisole/anisole/EDT (15 mL, 90:5:2:3 v/v/v/v), and shaking at room temperature for 3 h. The peptide was precipitated, centrifuged, and washed with cold diethyl ether to yield the crude white solid peptide. The peptide was dissolved in H$_2$O/CH$_3$CN with 0.1% TFA and purified using RP HPLC. Then, the pure fractions were collected, concentrated and lyophilized to afford pure solid white powder of c[(WE)$_4$WC] (SEQ ID NO: 2) peptide. MALDI-TOF (m/z) [C$_{78}$H$_{83}$N$_{15}$O$_{18}$S]: calcd, 1549.5761; found, 1572.2693 [M+Na]+; c[(WE)$_5$WC] (SEQ ID NO: 3): MALDI-TOF (m/z) [C$_{94}$H$_{100}$N$_{18}$O$_{22}$S]: calcd, 1864.6980; found, 1865.3943 [M+H]+; c[(WE)$_3$WC] (SEQ ID NO: 1): MALDI-TOF (m/z) [C$_{62}$H$_{66}$N$_{12}$O$_{14}$S]: calcd, 1234.4542; found, 1234.7385 [M]+; c[(LE)$_4$WC] (SEQ ID NO: 4): MALDI-TOF (m/z) [C$_{58}$H$_{87}$N$_{11}$O$_{18}$S]: calcd, 1257.5951; found, 1258.2421 [M+H]+; c[E$_4$W$_5$C] (SEQ ID NO: 5): MALDI-TOF (m/z) [C$_{78}$H$_{83}$N$_{15}$O$_{18}$S]: calcd, 1549.5761; found, 1549.1430 [M]+. A similar procedure was used for the synthesis of c[R$_4$W$_5$C] (SEQ ID NO: 219) except using Fmoc-Arg(Pbf)-OH instead of Fmoc-Glu(OtBu)-OH. c[R$_4$W$_5$C] (SEQ ID NO: 219): MALDI-TOF (m/z) [C$_{82}$H$_{103}$N$_{27}$O$_{10}$S]: calcd, 1657.8102; found, 1658.5018 [M+H]+.

Synthesis of l(CW(EW)$_4$) (SEQ ID NO: 188)

The linear peptide was assembled as described above using H-Trp(Boc)-2-chlorotrityl resin (384.6 mg, 0.3 mmol 0.78 mmol/g) in reaction vessel (Scheme S1). The peptide sequence was assembled using the appropriate amino acid building blocks Fmoc-Glu(OtBu)-OH (382.9 mg, 0.9 mmol), Fmoc-Trp(Boc)-OH (473.9 mg, 0.9 mmol), Fmoc-Cys(Trt)-OH (527.1 mg, 0.9 mmol), and HBTU (0.9 mmol, 341 mg) as the coupling reagent. The final N-terminal Fmoc group was deprotected. The peptide was cleaved from the resin and side chain was deprotected by reaction of the peptidyl resin with freshly prepared cleavage cocktail reagent R, TFA/thioanisole/anisole/EDT (15 mL, 90:5:2:3 v/v/v/v), for 3 h at room temperature. The linear protected peptide was precipitated, centrifuged, and purified by using RP-HPLC as mentioned above to yield l(CW(EW)$_4$) (SEQ ID NO: 188). MALDI-TOF (m/z) [C$_{78}$H$_{85}$N$_{15}$O$_{19}$S]: calcd, 1567.5867; found, 1606.1204 [M+K]+. Concentration of peptides was calculated spectrophotometrically by measuring absorbance at 280 nm. The extinction coefficients, $\varepsilon_{280}$, M$^{-1}$ cm$^{-1}$, for the peptides are the following: c[(WE)$_4$WC] (SEQ ID NO: 2)=28,000; c[(WE)$_5$WC] (SEQ ID NO: 3)=33,600; c[(WE)$_3$WC] (SEQ ID NO: 1)=2,400; c[(LE)$_4$WC] (SEQ ID NO: 4)=5,600; c[E$_4$W$_5$C] (SEQ ID NO: 5)=28,000; l(CW(EW)$_4$) (SEQ ID NO: 188)=28,000.

Labeling of Peptides with Fluorescent Dyes

Peptides were conjugated with Alexa546- and Fluorescein-5-maleimide (Life Technologies) in DMF at a ratio of 1.2:1 and incubated at room temperature for about 6 hours and then at 4° C. until the conjugation reaction was completed. 50 mM of sodium phosphate/150 mM NaCl buffer pH7.0 (saturated with argon) was added to the reaction mixture (1/10 of the total volume). The reaction progress was monitored by the reverse phase HPLC. The products were purified by the reverse phase HPLC, lyophilized and characterized by SELDI-TOF mass spectrometry. The concentration of the constructs was determined by absorbance at 556 and 494 nm using molar extinction coefficients of 93,000 M$^{-1}$·cm$^{-1}$ for Alexa546 and 68,000 M$^{-1}$·cm$^{-1}$ for Fluorescein-5 (FITC).

Synthesis of Peptide-Amanitin Constructs

Symmetric c[(WE)$_4$WC] (SEQ ID NO: 2) and asymmetric c[E$_4$W$_5$C] (SEQ ID NO: 5) peptides were conjugated to alpha-amanitin (Sigma-Aldrich) via cleavable S—S bond. Additionally, asymmetric c[E$_4$W$_5$C] (SEQ ID NO: 5) peptide was labeled with amanitin via non-cleavable bond. The conjugation Scheme consists of 2 steps: i) amanitin was conjugated with NHS group of the cleavable crosslinker, SPDP, N-succinimidyl 3-(2-pyridyl-dithio)-propionate or the non-cleavable crosslinker, GMBS, N-γ-maleimidobutyryl-oxysuccinimide ester (both crosslinkers were from (Thermo Scientific) in 50 mM sodium phosphate/150 mM NaCl buffer pH 8.5-9.0 at a ratio 1:20 at room temperature for 4 h to get SPDP-amanitin or GMBS-amanitin. The products were purified by the reverse phase HPLC on Zorbax SB-C18 column (9.4×250 mm, 5-Micron). SPDP-amanitin was eluted using a gradient: 0-25%, 40 min (water and acetonitrile with 0.05% TFA) and lyophilized. c[(WE)$_4$WC] (SEQ ID NO: 2) and c[E$_4$W$_5$C] (SEQ ID NO: 5) peptides were incubated with SPDP-amanitin or GMBS-amanitin in 100 mM sodium phosphate/150 mM NaCl buffer pH 7.8 (saturated with argon) at a ratio 1:1 at room temperature for 1 h to obtain amanitin-SPDP-peptides or amanitin-GMBS-peptide, respectively. The products were purified by the reverse phase HPLC on Zorbax SB-C18 column (9.4×250 mm, 5-Micron) using gradient 10-55%, 40 min (water and acetonitrile with 0.05% TFA). The products were lyophilized and characterized by SELDI-TOF mass-spectrometry. The calculated and obtained masses for the peptides are the following: c[$E_4W_5C$]-SPDP-amanitin: SELDI-TOF (m/z) [$C_{120}H_{139}N_{25}O_{33}S_3$]: calcd, 2555.7304; found 2555.5263 [M+H]$^+$; c[$E_4W_5C$]-GMBS-amanitin: SELDI-TOF (m/z) [$C_{125}H_{144}N_{26}O_{35}S_2$]: calcd, 2632.9279; found 2634.5723 [M+H]$^+$, and 2657.8214 [M+Na]$^+$; c[(WE)$_4$WC]-SPDP-amanitin: SELDI-TOF (m/z) [$C_{120}H_{139}N_{25}O_{33}S_3$]: calcd, 2553.9129; found 2554.5000 [M+1]$^+$.

Liposome Preparation

Liposomes such as Large Unilamellar Vesicles (LUVs) were prepared by extrusion. POPC, 1-palmitoyl-2-oleoyl-sn-glycero-3-phosphocholine (Avanti Polar Lipids), or a mixture of POPC with 0.5% of 18:1 NBD-PE, 1,2-dioleoyl-sn-glycero-3-phosphoethanolamine-N-7-nitro-2-1,3-benzoxadiazol-4-yl ammonium salt (Avanti Polar Lipids) were dissolved in chloroform, desolvated on a rotary evaporator, and dried under high vacuum for several hours. The phospholipid film was then rehydrated in 10 mM phosphate buffer pH 8.0, vortexed until the lipid bilayer was completely dissolved, and repeatedly (15-21 times) extruded through the membranes with 50 nm pore sizes to obtain LUVs.

Steady-State Fluorescence and CD

Freshly prepared peptides and POPC vesicles were mixed to have 5 µM of a peptide and 1.25 mM of lipids in the final solution. Steady-state fluorescence measurements were carried out on a PC1 spectrofluorometer (ISS, Inc.) under temperature control at 25° C. Tryptophan fluorescence was excited at 280 nm (there is no Phe or Tyr in the peptides) and recorded with the excitation and emission slits set at 1 nm. The polarizers in the excitation and emission paths were set at the "magic" angle (54.7o from the vertical orientation) and vertically (0°), respectively. Steady state CD measurements were carried out in MOS 450 spectropolarimeter (Bio-Logic, Inc.) with the same concentrations of peptide and lipids as it were used in fluorescence measurements.

pH-Dependence pH-dependent partitioning of the peptides into a lipid bilayer of membrane was investigated by the shift of the position of the fluorescence spectral maximum for the peptides in the presence POPC liposomes induced by a drop of pH from 8 to 2.5 by addition of HCl. The peptides were incubated overnight with 50-nm POPC liposomes (final concentration of the peptides and POPC in solution was 5 µM and 1 mM, respectively), and pH decrease was achieved by the addition of aliquots of 4, 2, 1 and 0.1 M HCl. pH was measured by micro-electrode probe (Thermo Electron Corporation, Orion Ross Micro pH electrode). Fluorescence spectra were recorded at each pH value. The spectra were analyzed by the decomposition algorithms using on-line PFAST toolkit (Protein Fluorescence and Structural Toolkit: pfast.phys.uri.edu/) to establish the position of the emission maximum. Finally, the positions of the fluorescence spectral maxima ($\lambda_{max}$) were plotted versus pH, and the Henderson-Hasselbalch equation was used to fit the data (using Origin 8.5 software):

$$\lambda_{max} = \lambda_{1max} + \frac{(\lambda_{1max} - \lambda_{2max})}{1 + 10^{(pH-pKa)}}$$

where $\lambda_{1max}$ and $\lambda_{2max}$ are the beginning and end of the transition, and pKa—is the midpoint of the transition.

Titration

Samples containing 5 µM of peptides at pH 8 and pH 3, and varying concentrations of lipids of the 50 nm POPC liposomes were prepared. The fluorescence spectra of peptides in all samples were measured at 280 nm excitation and 25° C. A series of POPC blanks with the same concentrations of lipids were measured with the same instrument settings and were subtracted from the corresponding fluorescence spectra of peptides in the presence of POPC. The areas under the emission spectra were calculated and the values were normalized to the first point (the emission of the peptide in the absence of POPC). The titration data were fitted by the peptide-membrane partition model to calculate the mole-fraction partition coefficient, K $$F = F_0 + \Delta F \frac{K \cdot C_{lip}}{W + K \cdot C_{lip}}$$

where $F_0$ and $\Delta F$ are the fluorescence intensity at the beginning and fluorescence increase as a result of the titration (in our case $F_0$ is 1), $C_{lipids}$ is the concentration of lipids; W is the molar concentration of water (55.3 M). Nonlinear least squares curve fitting procedures using Levenberg-Marquardt algorithm were implemented in Origin 8.5.0 SR1. The Gibbs free energy ($\Delta G$) was calculated according to the equation:

$$\Delta G = -RT \cdot \ln(K)$$

where R is the gas constant and T is the temperature in Kelvin.

Dual Quenching

POPC liposomes without and with 10% of the lipids replaced by 10-doxylnonadecane (10-DN) (Avanti Polar Lipids) were prepared in 10 mM citrate-phosphate buffer pH 8.0. Peptides and POPC liposomes were mixed to generate final concentrations of 7 µM peptide and 2.1 mM POPC without and with 10-DN. In some of the samples, the pH was lowered to pH 4 by addition of aliquot of 2 M citric acid, and other samples were kept at pH 8. To the samples of POPC liposomes containing no 10-DN, acrylamide (Sigma-Aldrich) was added to have a final concentration of 235 mM in solution. Concentration of peptides in all samples was kept constant. To observe quenching of tryptophan fluorescence by 10-DN or acrylamide, the tryptophan fluorescence was recorded as described above. The appropriate POPC blanks were measured and subtracted from the measured spectra before analysis. The percentage of quenching was calculated.

NBD-FRET

First, symmetrically NBD-labeled POPC liposomes containing 0.5% of NBD-PE were prepared. Next, 1.2 ml of 6 mM of symmetrically NBD-labeled POPC liposomes were incubated with 150 µl of 1 M freshly prepared membrane-impermeable dithionite in buffer at pH 8.0 to chemically deactivate of NDB only at outer leaflet of bilayer and obtain asymmetrically NBD-labeled POPC liposomes. The decrease of NBD fluorescence occurring in the result of quenching of NBD by dithionite was monitored at excitation of 463 nm and emission at 530 nm. The dithionite quenching leads to the reduction of about 60-65% of NBD fluorescence signal corresponding to the NBD on the outer leaflet of the bilayer. Next, POPC solution was passed through a G-10 sephadex (Sigma-Aldrich) column to remove the excess of dithionite. Asymmetrically labeled POPC liposomes were incubated with peptides at concentrations indicated above, and FRET from tryptophan residues to NBD at inner leaflet of bilayer was monitored at 280 nm excitation wavelength, and emission was recorded from 310 to 580 nm.

Cell Lines

Human cervix adenocarcinoma (HeLa) cells were acquired from the American Type Culture Collection. Cells were cultured in Dulbecco's Modified Eagle's Medium (DMEM) supplemented with 10% fetal bovine serum (FBS), 10 μg/mL of ciprofloxacin in a humidified atmosphere of 5% $CO_2$ and 95% air at 37° C.

Cytotoxic Assay

HeLa cells were loaded in the wells of 96-well plates (5,000 cells per well) and incubated overnight. Growth medium was replaced with the medium without FBS pH 6.2 or pH 7.4 containing increasing amounts of constructs (5, 10, 20, and 40 μM). The same volume of DMEM medium supplemented with 20% FBS, pH 7.4 was added after 2 h of treatment. After 48 h of incubation a colorimetric reagent (CellTiter 96 $AQ_{ueous}$ One Solution Assay, Promega) was added for 1 h followed by measuring absorbance at 490 nm to assess cell viability. All samples were prepared in triplicate.

Proliferation Assay

HeLa cells were loaded in the wells of 96-well plates (5,000 cells per well) and incubated overnight. Growth medium was replaced with the medium without FBS pH 6.0 or pH 7.4 containing increasing amounts of peptide-amanitin construct (0.5, 1, 2, and 4 μM). The construct was removed after 3 h. After 48 h of incubation in standard growth medium, a colorimetric reagent (CellTiter 96 $AQ_{ueous}$ One Solution Assay, Promega) was added for 1 h followed by measuring absorbance at 490 nm to assess cell viability. All samples were prepared in triplicate.

Fluorescent Microscopy

HeLa cells (8,000 cells per dish) were seeded in the center of a 35-mm dish with a 10-mm glass-bottom window coated with collagen (MatTek Corp). Next day cells were incubated with 5 μM of FITC-labeled c[E$_4$W$_5$C] (SEQ ID NO: 5) peptide for 30 min in DMEM medium without FBS at pH 7.4 or 6.2. Cells were washed 5 times at pH 7.4 and 0.4% Trypan Blue was added for 5 min (1/10 of the total volume). Fluorescent images were acquired with a Retiga CCD camera (Qimaging) mounted to an inverted Olympus IX71 microscope (Olympus America, Inc.).

Cellular Uptake

HeLa cells (150,000 cells per sample of total volume of 500 μL) were incubated with 5 μM of Alexa546-labeled pH-senstive, c[E$_4$W$_5$C] (SEQ ID NO: 5), and pH-insensitive, c[R$_4$W$_5$C] (SEQ ID NO: 219), peptide conjugates in Leibovitz's (L15) medium at pH 6.2 and 7.4 in the presence or absence of 4% of fetal bovine serum (FBS) for 6 hours, followed by extensive washing with L15 medium. The cellular uptake of the constructs was measured by fluorescent signal from cells counted using cellometer (Cellometer Vision CBA, Nexcelom). 4% of FBS was used to mimic the amount of albumin in whole blood, which contains 45% of red blood cells, white blood cells and platelets suspended in plasma (about 55% of volume). Plasma is composed of about 92% of water, 1% of vitamins, sugars, salts, minerals, hormones and 7% of vital proteins including albumin, gamma globulins and other clotting factor. Thus, the amount of albumin in whole blood is expected to be less than 3.6%.

Ex Vivo Fluorescence Imaging

4T1 breast tumors were established by subcutaneous injection of 4T1 cells ($8 \times 10^5$ cells/0.1 mL/flank) in the right flank of adult female BALB/c mice (about 19-22 g weight) obtained from Harlan Laboratories. When tumors reached about 6 mm in diameter single tail vein injections of 100 μl of 40 μM Alexa546-peptides were performed. Control mice bearing tumor used to establish an auto fluorescence signal did not receive fluorescent peptides. At 4 h post-injection euthanization and necropsy was performed followed by ex vivo imaging of tumor, kidneys, liver, lungs and muscle. Mean fluorescence intensity of tumor and organs was calculated using Kodak software.

Statistical Analysis

Statistically significant differences were determined by two-tailed unpaired Student's t-test (p-level<0.05 was taken as significant).

Delivery of Compound into Cells and Tissues Using pH-Sensitive Cyclic Peptides

Figure 2:
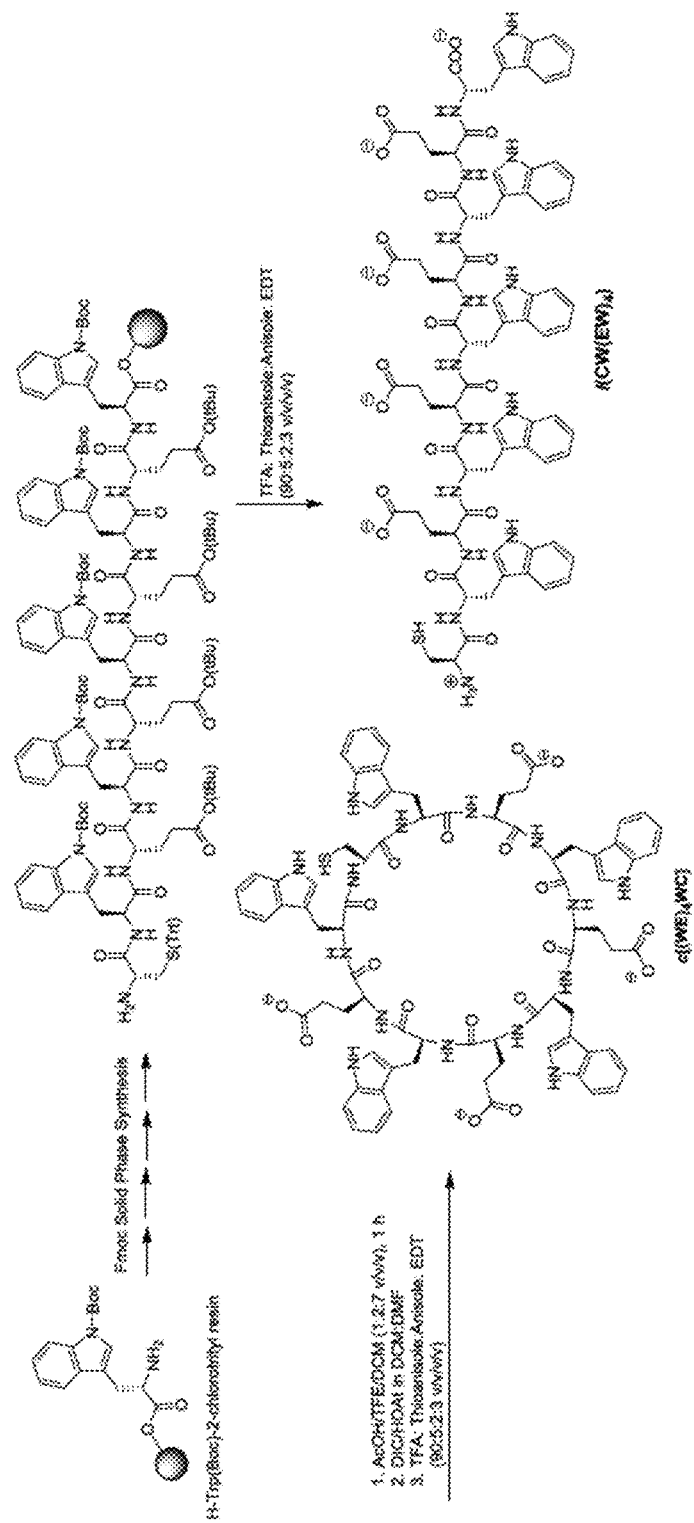
FIG. 2 is a schematic presentation showing linear l(CW (EW)$_4$) (SEQ ID NO: 188) and cyclic c[(WE)$_4$WC] (SEQ ID NO: 2) peptides synthesis.

Among the investigated peptides were one linear and five cyclic peptides (FIG. 1 and Table 6). All peptides tested contain: i) single cysteine (Cys, C) residue for conjugation purposes, ii) at least one tryptophan (Trp, W) for ability to record fluorescence signal, iii) 3-5 protonatable glutamic acid (Glu, E) residues to trigger pH-dependent interaction with membrane. The first three peptides, c[(WE)$_4$WC] (SEQ ID NO: 2), c[(WE)$_5$WC] (SEQ ID NO: 3), and c[(WE)$_3$WC] (SEQ ID NO: 1) have 3, 4, and 5 repeating units of WE, respectively, where W and E are alternating in the cyclic peptide. Another peptide, c[(LE)$_4$WC] (SEQ ID NO: 4), has leucine (Leu, L) instead of Trp to investigate the role of aromatic Trp residues for peptides interaction with the membrane. Fifth peptide, c[E$_4$W$_5$C] (SEQ ID NO: 5), is an asymmetric; it has five Trp residues located on one side of the cycle, while four Glu residues are located on the other side of the cycle. Finally, we synthesized also one linear l(CW(EW)$_4$) (SEQ ID NO: 188)10-residue peptide for the comparison with the cyclic peptides. The peptides were synthesized by employing Fmoc/tBu-based solid phase chemistry. As representative examples, the synthesis of l(CW(EW)$_4$) (SEQ ID NO: 188) and c[(WE)$_4$WC] (SEQ ID NO: 2) peptides are depicted in scheme (FIG. 2). All peptides were purified (95-99%) by reverse phase HPLC.

TABLE 6

Properties of the synthesized peptides.

| Peptide | Calculated M.W. | Found M.W. | Retention time in HPLC | % purity |
|---|---|---|---|---|
| c[(WE)$_4$WC] | 1549.5761 | 1572.2693 [M + Na]$^+$ | 35.2-36.7 | 99 |
| c[(WE)$_5$WC] | 1864.6980 | 1865.3943 [M + H]$^+$ | 35.8-37.2 | 99 |
| c[(WE)$_3$WC] | 1234.4542 | 1234.7385 [M]$^+$ | 35.0-36.0 | 99 |
| c[(LE)$_4$WC] | 1257.5951 | 1258.2421 [M + H]$^+$ | 35.2-36.3 | 95 |
| c[E$_4$W$_5$C] | 1549.5761 | 1549.1430 [M]$^+$ | 36.6-37.7 | 99 |
| l(CW(EW)$_4$) | 1567.5867 | 1606.1204 [M + K]$^+$ | 32.3-33.2 | 99 |
| c[R$_4$W$_5$C] | 1657.8102 | 1658.5018 [M + H]$^+$ | 32.0-32.1 | 99 |

Figure 3:
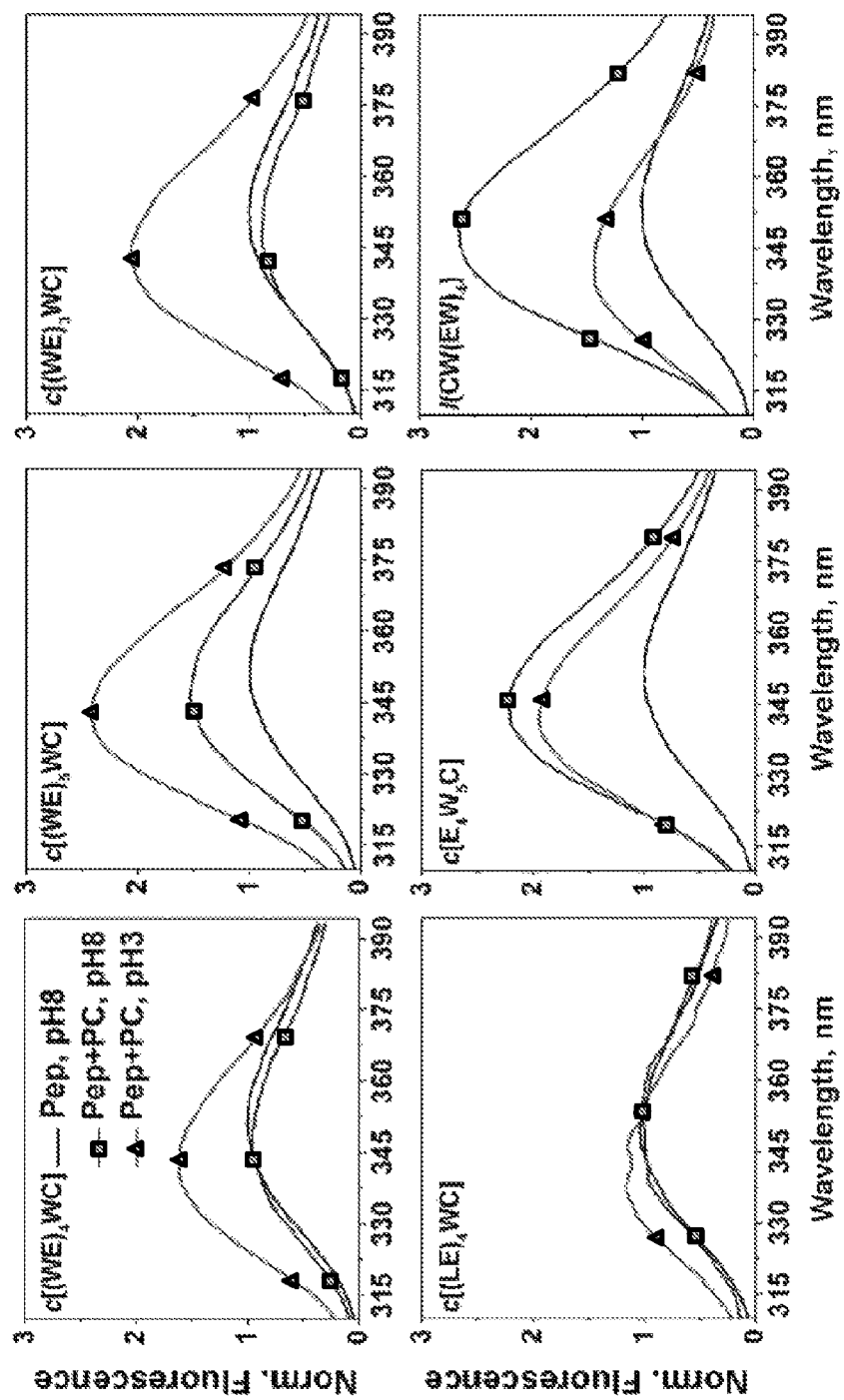
FIG. 3 is a set of graphs showing fluorescence of peptides in phosphate buffer at pH 8 (black lines) and in the presence of 1-palmitoyl-2-oleoyl-sn-glycero-3-phosphocholine (POPC) liposomes at pH 8 (blue lines with squares) and pH 3 (red lines with triangles). The excitation wavelength was 280 nm. The spectral parameters are given in Table 7.
Figure 4:
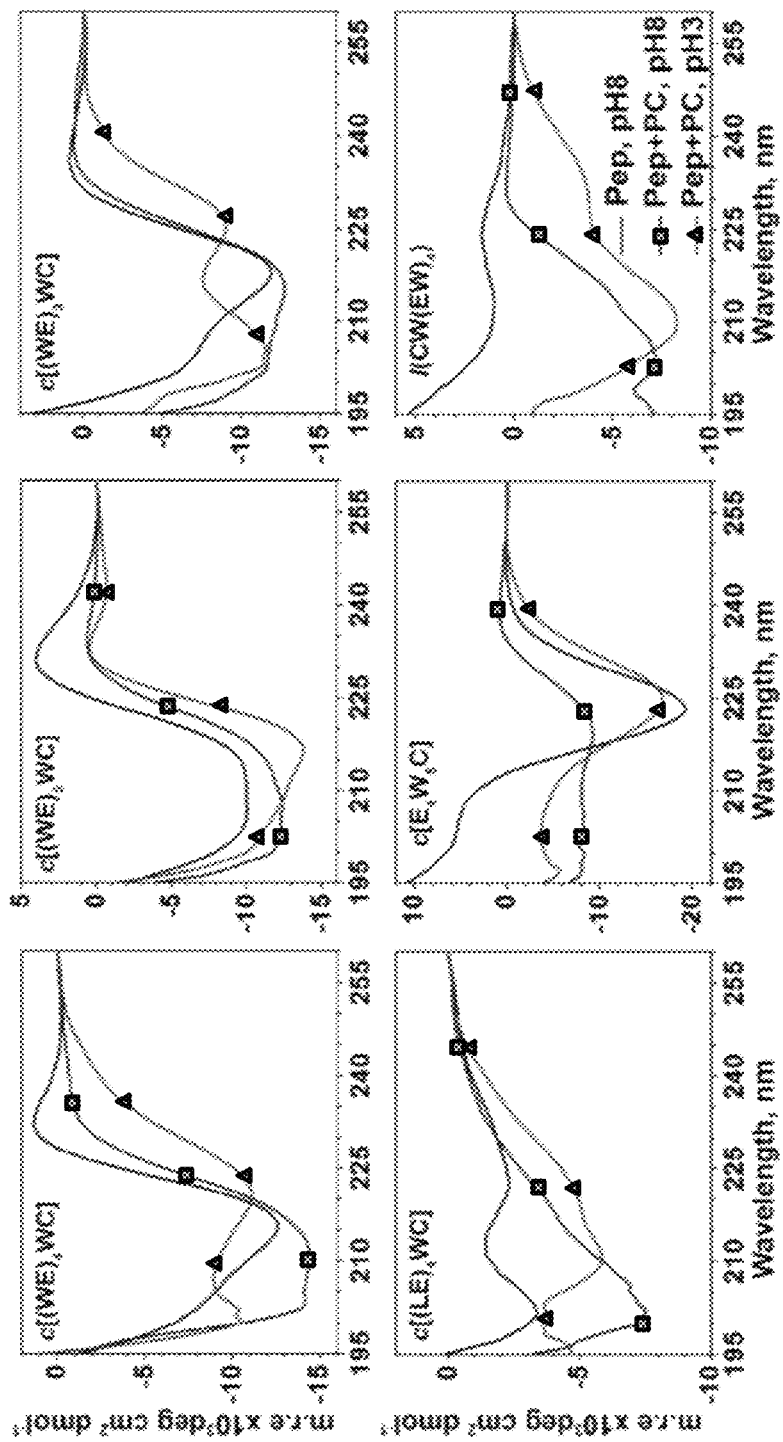
FIG. 4 is a set of graphs showing the circular dichroism of peptides in phosphate buffer at pH 8 (black line) and in presence of POPC liposomes at pH 8 (blue line with squares) and pH 3 (red line with triangles).

Fluorescence and CD spectroscopies were employed to monitor pH-dependent peptides interaction with the lipid bilayer of liposomes (FIGS. 3 and 4, Table 7). All peptides demonstrated pH-dependent partition into the membrane. Asymmetric cyclic peptide with Trp residues located on one side of the cycle, c[E$_4$W$_5$C] (SEQ ID NO: 5), partitions into the membrane facing Trp residues inside a bilayer and exposing Glu to the extracellular space. The drop of pH leads to the protonation of carboxyl groups of Glu residues, which increases peptides hydrophobicity and promotes a further partition of peptides in the bilayer. As a result, positions of maximum of fluorescence spectra shift to 6-9 nm to short wavelengths (FIG. 3 and Table 7). c[(WE)$_4$WC]

(SEQ ID NO: 2), c[(WE)$_5$WC] (SEQ ID NO: 3) and c[(WE)$_3$WC] (SEQ ID NO: 1) peptides show similar CD signals at pH 8, which are altered by interaction with lipid bilayer and drop of pH. The CD signal of c[E$_4$W$_5$C] (SEQ ID NO: 5) peptide was different but was also pH-dependent. The characteristic CD signal of excitation was not observed with a minimum at 232-235 nm. Such an exciton might be formed as a result of the stacking of aromatic amino acids due to peptide aggregation/stacking (Roy et al. (2005) *Biopolymers* 80(6):787-799). Thus, it was concluded that at the concentrations of the peptides used in this study, the formation of tubular structures is unlikely.

TABLE 7

The spectral parameters of the peptides in phosphate buffer at pH 8, in the presence of POPC liposomes at pH 8 and pH 3 are presented. The parameters were obtained from analysis of the fluorescence spectra shown in FIG. 3: the maximum position of the fluorescence spectrum $\lambda_{max}$, in nm; S—the normalized area under the spectra (normalization was done on the area under the spectrum for peptides at pH 8 in absence of POPC liposomes, black lines on FIG. 3).

| Peptide | $\lambda_{max}$, nm | | | S | |
|---|---|---|---|---|---|
| | Pep, pH8 | Pep-PC, pH8 | Pep-PC, pH3 | Pep-PC, pH8 | Pep-PC, pH3 |
| c[(WE)$_4$WC] | 350.5 ± 0.2 | 347.5 ± 1.2 | 341.1 ± 0.9 | 1.1 ± 0.1 | 1.6 ± 0.2 |
| c[(WE)$_5$WC] | 350.3 ± 0.2 | 346.7 ± 1.2 | 341.2 ± 0.4 | 1.5 ± 0.3 | 2.1 ± 0.3 |
| c[(WE)$_3$WC] | 351.0 ± 0.2 | 349.1 ± 0.7 | 341.7 ± 0.2 | 0.9 ± 0.1 | 1.7 ± 0.3 |
| c[(LE)$_4$WC] | 348.7 ± 0.3 | 348.2 ± 0.6 | 339.6 ± 1.2 | 1.1 ± 0.0 | 1.1 ± 0.1 |
| c[E$_4$W$_5$C] | 350.6 ± 0.2 | 342.8 ± 0.4 | 340.2 ± 0.4 | 2.4 ± 0.3 | 2.4 ± 0.5 |
| l(CW(EW)$_4$) | 353.0 ± 0.7 | 346.6 ± 0.7 | 339.8 ± 0.6 | 2.3 ± 0.4 | 1.6 ± 0.4 |

Figure 5:
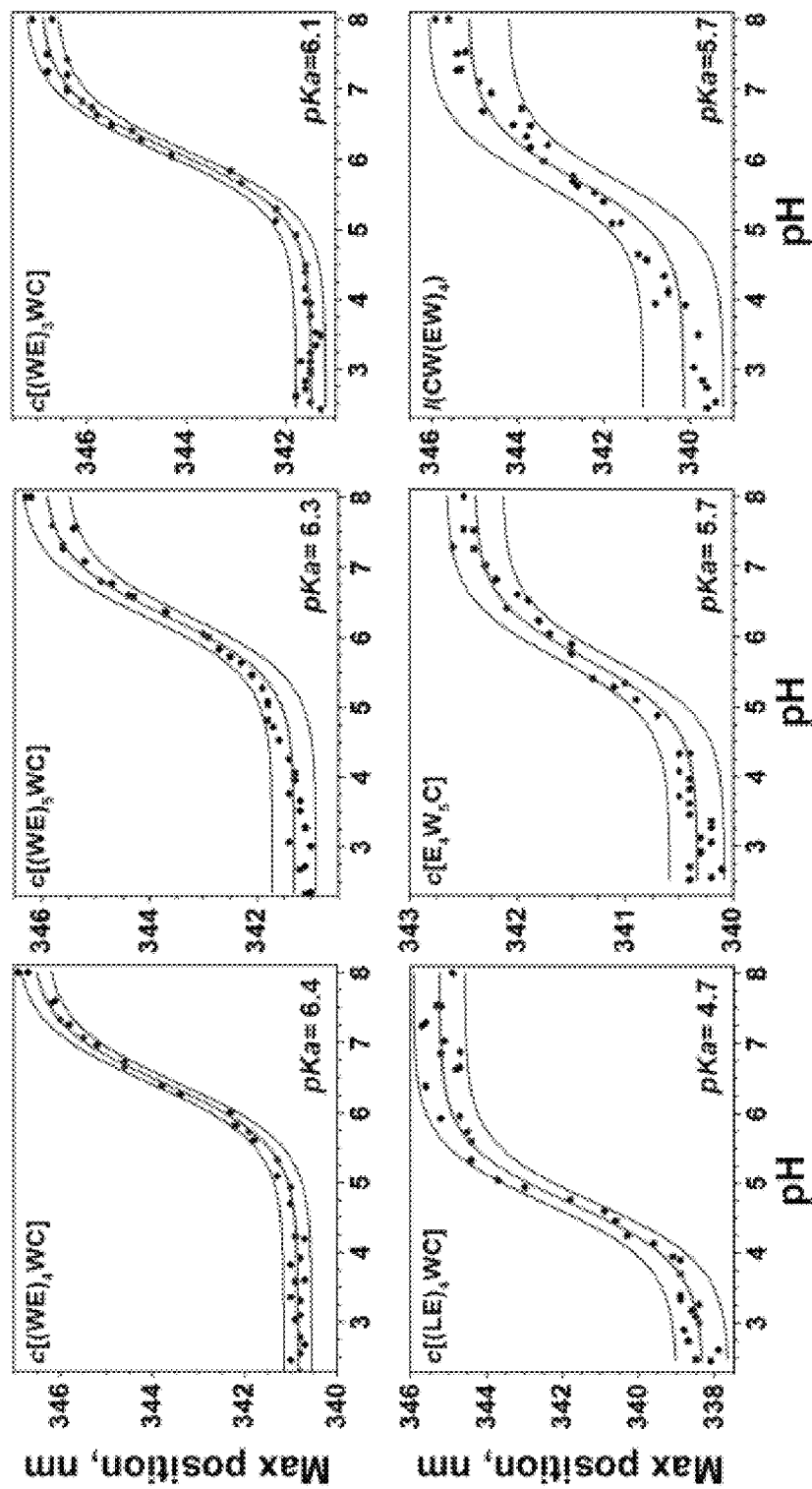
FIG. 5 is a set of graphs showing changes of tryptophan fluorescence, which are used to follow the partition of the peptides into POPC liposomes as a function of pH. Fitting curve (middle line) and 95% confidence interval (outer lines) are shown.

By monitoring the shift of the position of the maximum of fluorescence spectra for the peptides as a result of the pH drop, an apparent pK of peptides partition into the bilayer was established. The pK for most cyclic and linear peptides varies in the range of 5.7-6.4, while the smallest pK value observed for the cyclic Leu-containing peptide, c[(LE)$_4$WC] (SEQ ID NO: 4) (FIG. 5).

Figure 6:
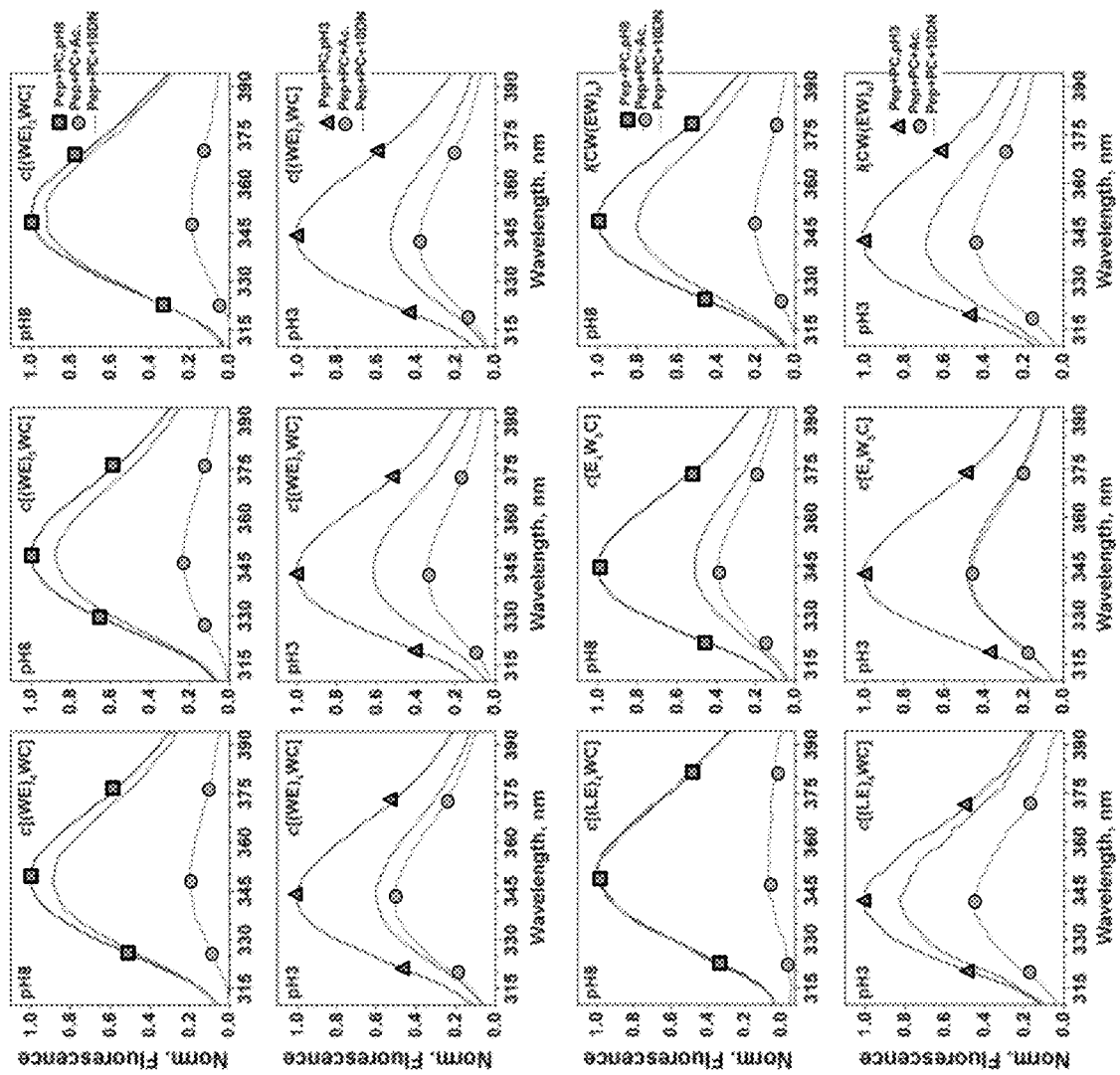
FIG. 6 is a set of graphs showing quenching of fluorescence of peptides in the presence of POPC liposomes at pH 8 (blue lines with squares) or at pH 3 (red lines with triangles) by acrylamide (green lines with circles), and 10-DN (magenta lines). The percentage of quenching is given in Table 8.
Figure 7:
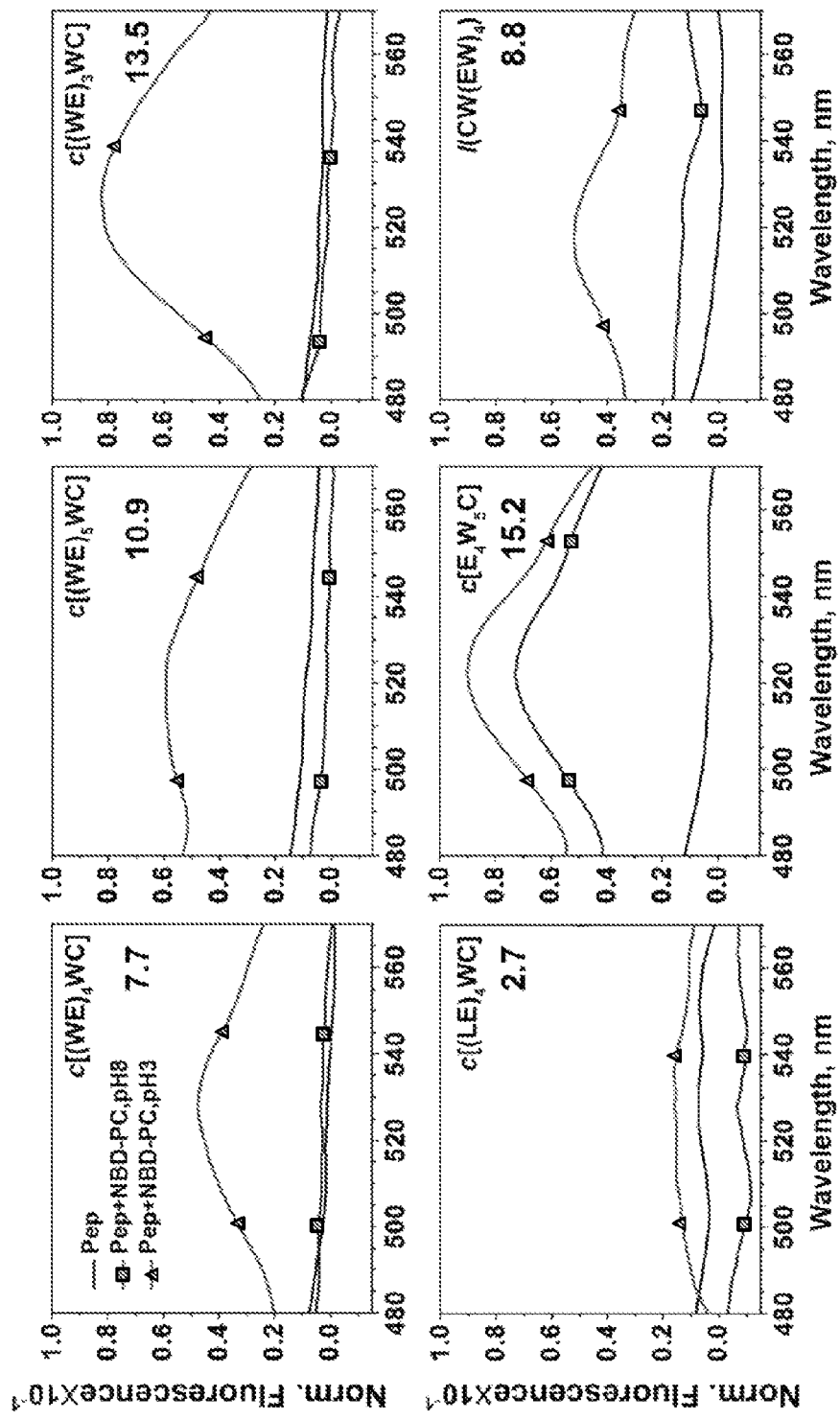
FIG. 7 is a set of graphs showing fluorescence spectra of peptides in phosphate buffer at pH 8 (black lines) and in presence of asymmetrically labeled POPC liposomes containing nitrobenzoxadiazole (NBD) at inner leaflet at pH 8 (blue lines with squares) and at pH 3 (red lines with triangles). Förster resonance energy transfer (FRET) is monitored from tryptophan residues to NBD, which occurs when both fluorophores are in a proximity to each other (within 5-15 Å). Thus, when tryptophan is located at outer leaflet of the bilayer, no significant energy transfer to NBD at inner leaflet occurs (the distance is about 50-60 Å). Thus, energy transfer would be detected only if tryptophan residues were located in the middle of the membrane or in the inner leaflet. The FRET signal is maximal when the tryptophan is located in close proximity to the headgroups of the inner leaflet. The numbers indicate an increase of FRET at pH 3 compared to the peptide fluorescence in phosphate buffer at pH 8.

To establish localization of the peptides within a lipid bilayer of the membrane, a dual quenching assay (Caputo G A & London E (2003) *Biochemistry* 42(11):3265-3274) was used (FIG. 6 and Table 8). Effective quenching of fluorescence by acrylamide would occur only for tryptophan residues exposed to polar parts of outer or inner leaflets of the bilayer. At the same time, tryptophan residues located in the middle of a membrane would be effectively quenched by 10-DN. The result of the dual quenching assay allows the determination of whether tryptophan residues are located in the middle of a membrane or close to the polar headgroups of the bilayer. However, it does not allow distinguishing between locations at the outer or inner leaflets of the bilayer. Therefore, FRET assays were also performed (McIntyre J C & Sleight R G (1991) *Biochemistry* 30(51):11819-11827; Clausell et al. (2006) J Phys Chem B 110(9):4465-4471) (FIG. 7). First, POPC liposomes symmetrically-labeled with NBD dye were prepared. Then, membrane-impermeable dithionite was used to modify chemically and quench the fluorescence of NBD at the outer leaflet of the bilayer followed by removal of dithionite by gel filtration. As a result, asymmetrically-labeled liposomes with NBD only at the inner leaflet were obtained. The c[E$_4$W$_5$C] (SEQ ID NO: 5) demonstrated the highest quenching by 10-DN and the highest energy transfer at pH 8 indicating the internal position of Trp residues within the bilayer of a membrane. All other peptides are located at the outer leaflet of the bilayer at pH 8. Among c[(WE)$_4$WC] (SEQ ID NO: 2), c[(WE)$_5$WC] (SEQ ID NO: 3), and c[(WE)$_3$WC] (SEQ ID NO: 1) peptides, the peptide with smallest cycle, c[(WE)$_3$WC] (SEQ ID NO: 1), showed the deeper partition into membrane and closer location to the inner leaflet, since FRET signal was the highest for it. Linear peptide, l(CW(EW)$_4$) (SEQ ID NO: 188), also demonstrated partition into bilayer in the result of the pH drop.

TABLE 8

The percentage of peptides fluorescence quenching by addition of acrylamide (AC) or 10-DN at pH 8 and pH 3 in the presence of POPC liposomes are shown. The values were obtained from analysis of the fluorescence spectra shown in FIG. 6.

| | Pep-PC + AC pH8 | Pep-PC + 10-DN pH8 | Pep-PC + AC pH3 | Pep-PC + 10-DN pH3 |
|---|---|---|---|---|
| c[(WE)$_4$WC] | 87 | 11 | 50 | 40 |
| c[(WF)$_5$WC] | 7$ | 1.3 | 68 | 40 |
| c[(WE)$_3$WC] | 83 | 6 | 63 | 47 |
| c[(LE)$_4$WC] | 96 | 0 | 59 | 17 |
| c[E$_4$W$_5$C] | 61 | 49 | 54 | 52 |
| l(CW(EW)$_4$) | 81 | 20 | 56 | 31 |

Figure 8:
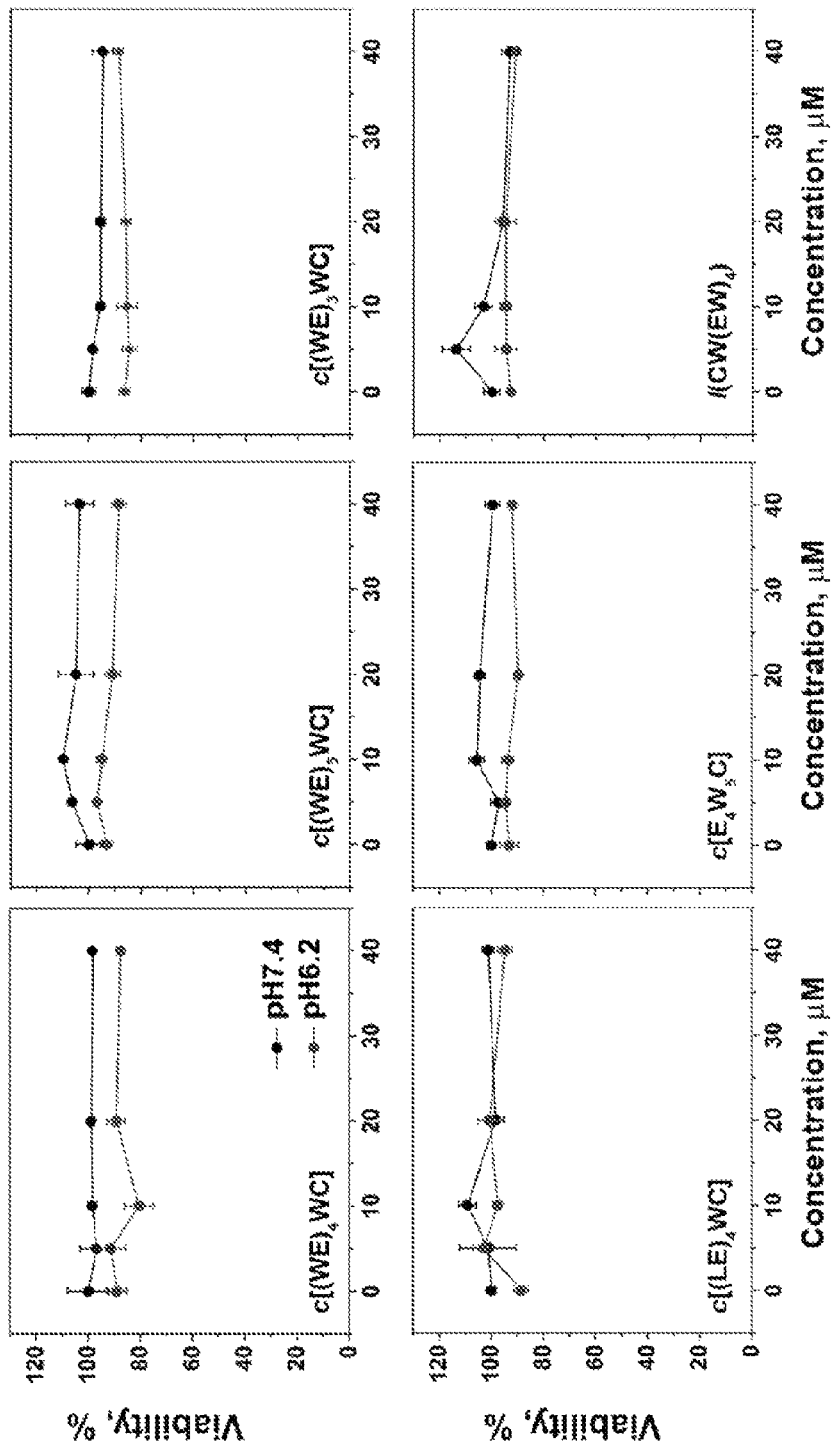
FIG. 8 is a set of graphs showing viability (%) as of HeLa cells at increasing contentcations of peptides. HeLa cells were treated with increasing concentrations of peptides without FBS at pH 6.2 (red lines and circles) or pH 7.4 (black lines and circles). The same volume of Dulbecco's Modified Eagle Medium (DMEM) medium supplemented with 20% FBS, pH 7.4 was added after 2 h of treatment. After 48 hours of incubation MTS assay was performed to access cell viability.
Figure 9:
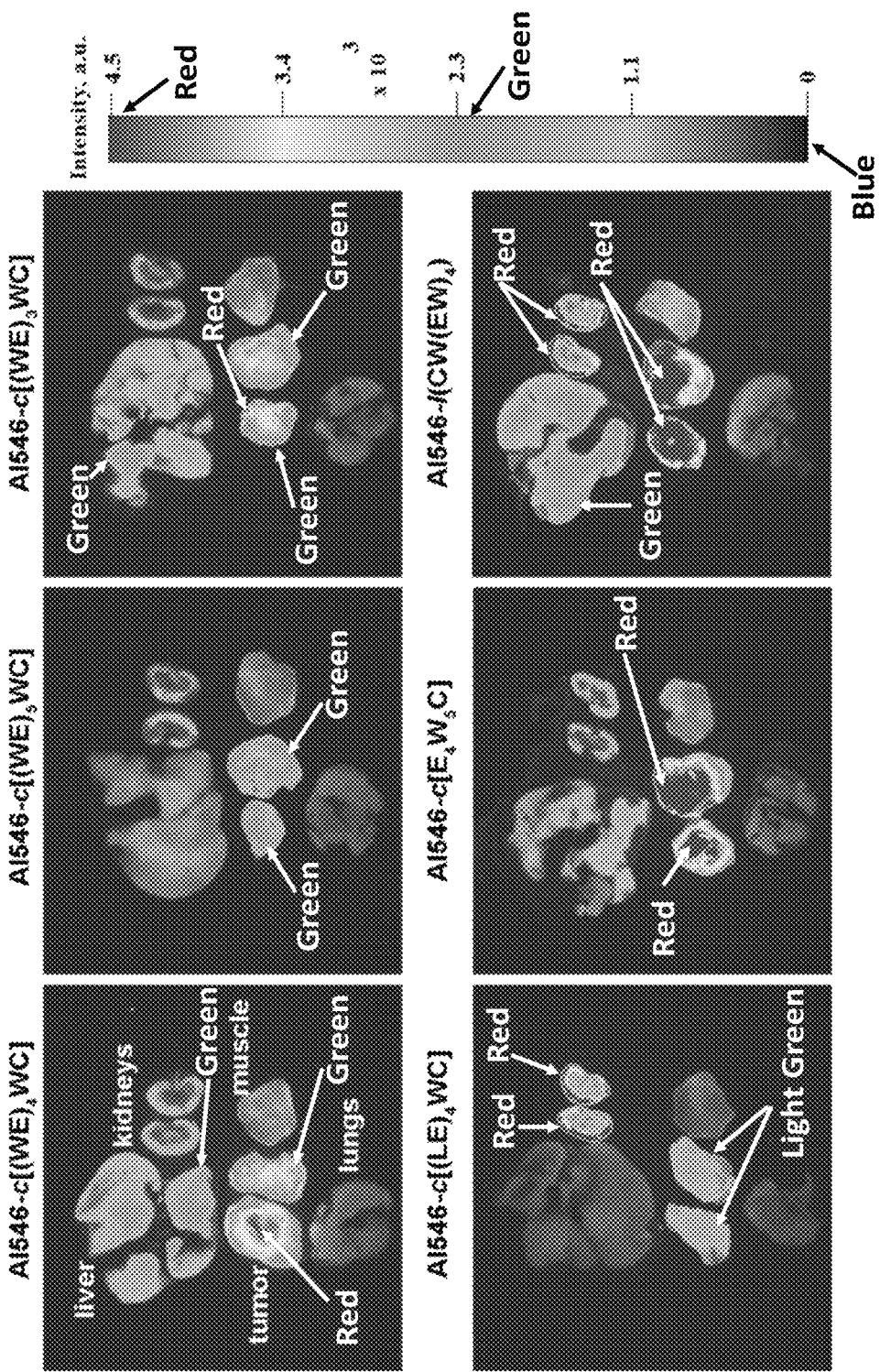
FIG. 9 is a set of images showing ex vivo fluorescence imaging of tumor, muscle, lungs, liver and kidneys collected at 4 h after intravenous (IV) administration of Alexa546-peptides. Three mice per peptide were used in the study.

Since all peptides demonstrated pH-dependent interaction with the lipid bilayer of the membrane and no cytotoxicity was observed (FIG. 8), animal studies were performed to identify the lead peptide demonstrating best tumor targeting. The murine 4T1 xenograft model, which closely mimics stage IV of human breast cancer (Tao et al. (2008) *BMC Cancer* 8:228; Yang et al. (2004) *Cell* 117(7):927-939; Eckhardt et al. (2005) *Mol Cancer Res* 3(1):1-13) was used in this study. Small 4T1 tumor (tumor volume<150 mm$^3$) generates a significant level of lactate and serve as a good model of an aggressive, acidic tumor (Serganova et al. (2011) Clin Cancer Res 17(19):6250-6261). All peptides were covalently conjugated with Alexa546-malemide. The fluorescent constructs were given as a single IV injection, and at 4 h after administration, animals were euthanized followed by necropsy. The mean fluorescence of tumor, muscle, kidney, liver and lungs was recorded and analyzed (FIG. 9). The least targeting was observed for Leu-containing peptide, c(LE)$_4$CW. Among cyclic peptides, tumor targeting was established for symmetric, e.g., c[(WE)$_4$WC] (SEQ ID NO: 2), and asymmetric, e.g., c[E$_4$W$_5$C] (SEQ ID NO: 5), peptides.

Figure 10:
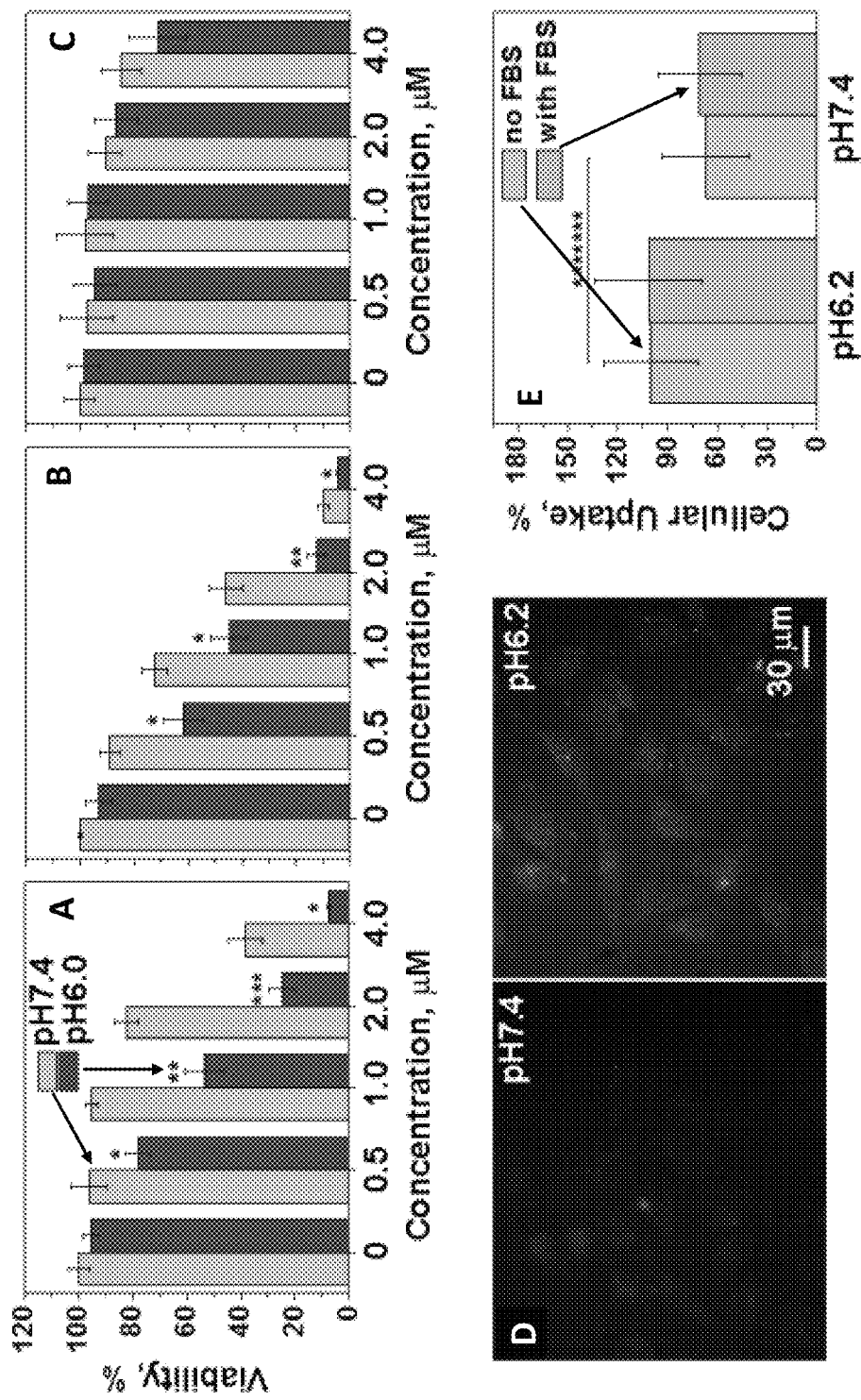
FIG. 10A-E are graphs and images showing viability and cellular uptake after treatment with various peptides. (A-C) Concentration- and pH-dependent inhibition of HeLa cells proliferation was monitored at 48 h after incubation of cells within (A) cleavable c[(WE)$_4$WC]—S—S-amanitin, (B) cleavable c[E$_4$W$_5$C]—S—S-amanitin and (C) non-cleavable c[E$_4$W$_5$C]-amanitin constructs for 3 h at normal (pH 7.4) and low (pH 6.0) pHs followed by constructs removal and keeping cells in DMEM with 10% FBS at pH 7.4. (D) HeLa cells were treated with FITC-labeled c[E$_4$W$_5$C] (SEQ ID NO: 5) peptide conjugate (5 μM) for 30 min at pH 7.4 or 6.2, followed by washing at pH 7.4 in both cases, addition of Trypan Blue for 5 min and live cell imaging. (E) Cellular uptake of Alexa546-labeled c[E$_4$W$_5$C] (SEQ ID NO: 5) peptide conjugates (5 μM) treated with HeLa cells for 6 h in L-15 media at pH6.2 in absence and presence of 4% of FBS, followed by washing and counting of fluorescent signal from cells using cellometer. Data are presented as mean±St.D. The two-tailed unpaired Student's t-test was used to calculate p-levels.

Symmetric, c[(WE)$_4$WC] (SEQ ID NO: 2), and asymmetric, c[E$_4$W$_5$C] (SEQ ID NO: 5), cyclic peptides were evaluated for their ability to move polar cargo across the membrane. As a polar cargo, amanitin was used, which is a cell-impermeable cyclic peptide Amantin is a deadly toxin, which inhibits RNA polymerase II, if transferred across the lipid bilayer of the plasma membrane. pH- and concentration-dependent cell death was observed after treatment of HeLa cells with up to 4 µM of c[(WE)$_4$WC]—S—S-amanitin (c[(WE)$_4$WC]-SPDP-amanitin, FIG. 10A) and c[E$_4$W$_5$C]—S—S-amanitin (c[E$_4$W$_5$C]-SPDP-amanitin, FIG. 10B) for just 3 h. A previous report showed that amanitin alone does not induce cell death at the concentrations used and for the duration of treatment of 2-4 h (Moshnikova et al. (2013) *Biochemistry* 52(7):1171-1178). Another construct, where amanitin was conjugated to the asymmetric c[E$_4$W$_5$C] (SEQ ID NO: 5) cyclic peptide via non-cleavable bond (c[E$_4$W$_5$C]-GMBS-amanitin, FIG. 10C), was also tested. The cytotoxic effect for the non-cleavable construct was reduced significantly at both pHs. This might indicate that the equilibrium is shifted toward a peptide membrane-bound form, and cleavage of amanitin from the peptide is required to allow amanitin to reach RNA polymerase II in the nucleus. Alternatively, if the cyclic peptide-amanitin is translocated into cytoplasm, the cleavage of amanitin might be required, since affinity of the peptide-amanitin to the RNA polymerase II might be reduced compared to the affinity of free amanitin to the RNA polymerase II. Based on the obtained results, it was proposed that at high/normal pH an asymmetric cyclic peptide is mostly located at the outer leaflet of the bilayer. In the result of pH drop, protonation of Glu residues leads to the enhancement of peptide hydrophobicity and partition into bilayer, where it is mostly concentrated on the inner leaflet since Glu residues could be de-protonated in the cytoplasm of cells. This assumption was further confirmed by quenching of fluorescence of FITC-labeled asymmetric cyclic peptide by cell impermeable Trypan Blue (FIG. 10C). Trypan Blue is used to quench the fluorescence of FITC located in the extracellular space (Nuutila J & Lilius E M (2005) *Cytometry A* 65(2):93-102). Cells treated with the FITC-labeled peptide at low pH followed by Trypan Blue quenching show a higher level of the fluorescent signal compared to the cells treated with the FITC-labeled peptide at normal pH followed by Trypan Blue quenching. This result indicates that at normal pH FITC is more exposed to extracellular space (to Trypan Blue) in contrast to low pH.

Figure 11:
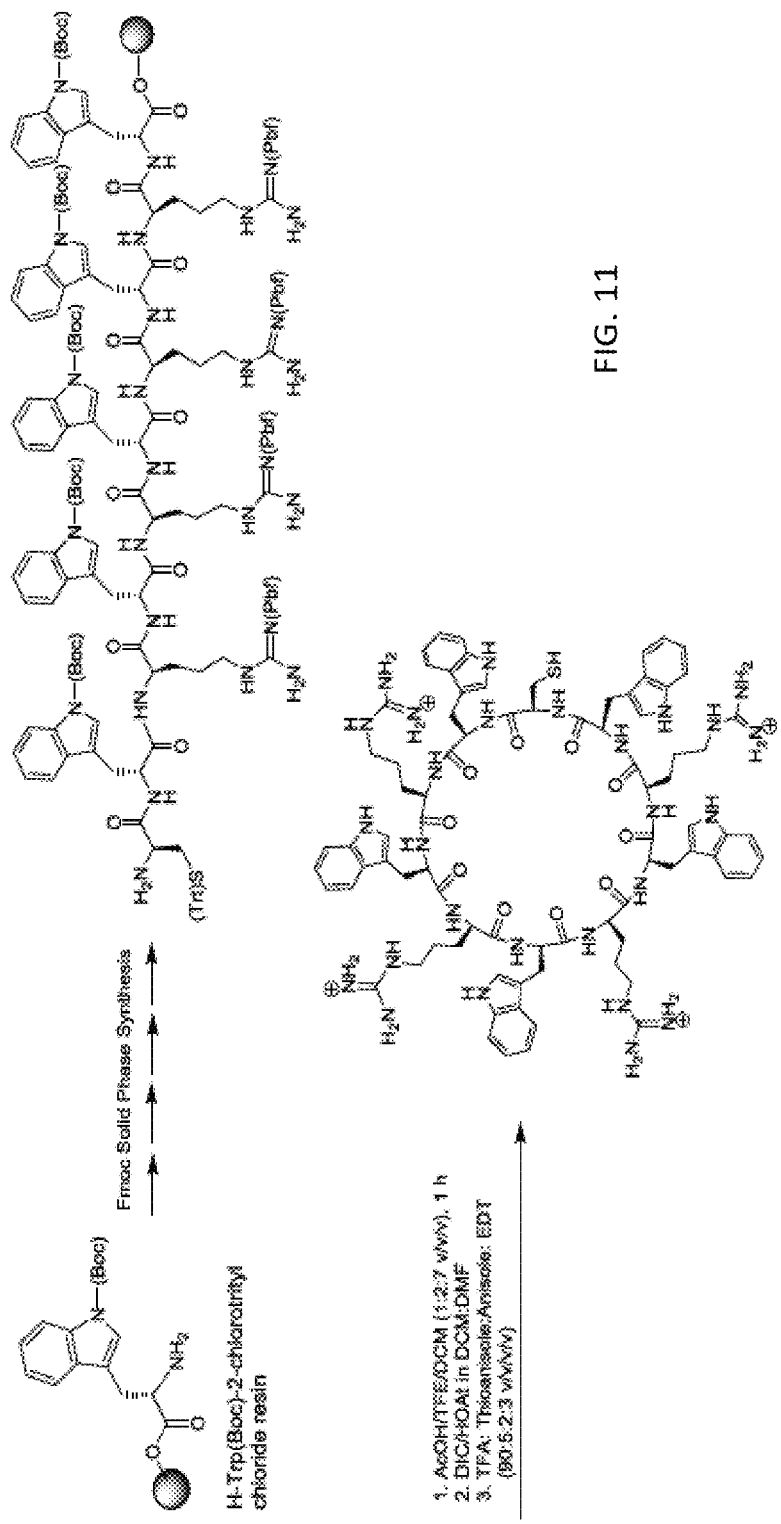
FIG. 11 is a schematic showing synthesis of c[R$_4$W$_5$C] (SEQ ID NO: 224).
Figure 12B:
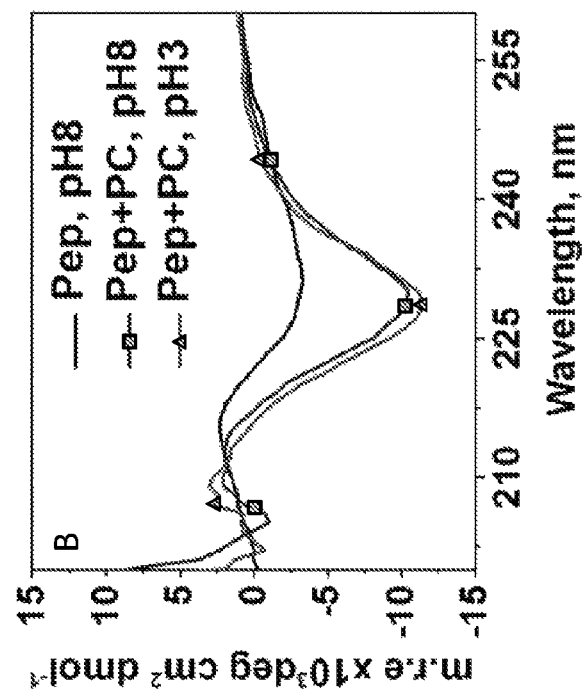
FIGS. 12A and B are a set of graphs showing the fluorescence (A) and CD (B) of positively-charged asymmetric cyclic peptide, c[R$_4$W$_5$C] (SEQ ID NO: 219), in phosphate buffer at pH 8 (black lines) and in the presence of POPC liposomes at pH 8 (blue lines with squares) and pH 3 (red lines with triangles). The excitation wavelength was 280 nm.
Figure 12A:
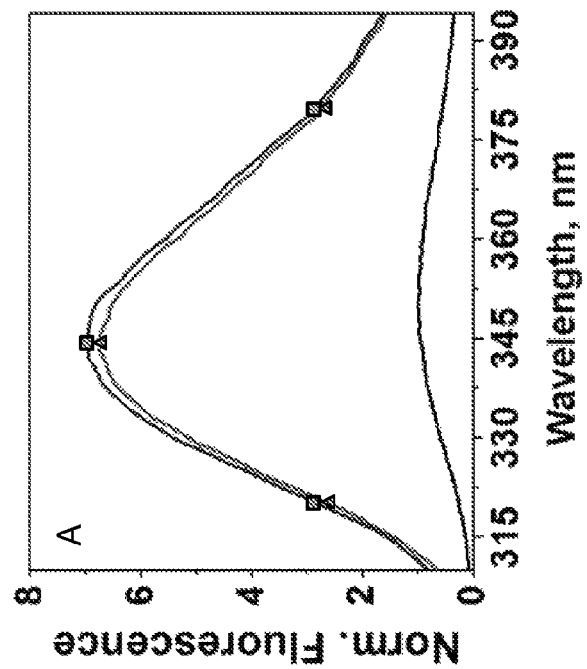

Next, a positively-charged asymmetric cyclic peptide was synthesized: c[$R_4W_5$C] (SEQ ID NO: 219), where Glu residues were replaced by Arg residues (see scheme in FIG. 11). This WR-peptide interacts with the lipid bilayer of the membrane at high pH (FIG. 12) due to the presence of Trp residues. At the same time, it does not exhibit pH-dependent changes in interaction with the lipid bilayer of membrane (FIG. 12), thus it can serve as a pH-insensitive control for pH-sensitive WE-cyclic asymmetric peptide, c[$E_4W_5$C] (SEQ ID NO: 5).

Cellular uptake of Alexa546-labeled pH-senstive, c[$E_4W_5$C] (SEQ ID NO: 5), and pH-insensitive, c[$R_4W_5$C] (SEQ ID NO: 219), peptide conjugates was tested in absence and presence of FBS at normal and low pHs. The cellular uptake was measured on a cellometer. The cellular uptake of Alexa546-labeled pH-senstive c[$E_4W_5$C] (SEQ ID NO: 5) peptide conjugate at both pHs in presence and absence of FBS is shown on FIG. 10E. A statistically significant difference was observed in cellular uptake of peptide at normal and low pHs (in contrast to the uptake of the pH-insensitive peptide, which exhibits higher uptake at normal pH than at low), and no significant reduction of the uptake in the presence of FBS.

Figure 13B:
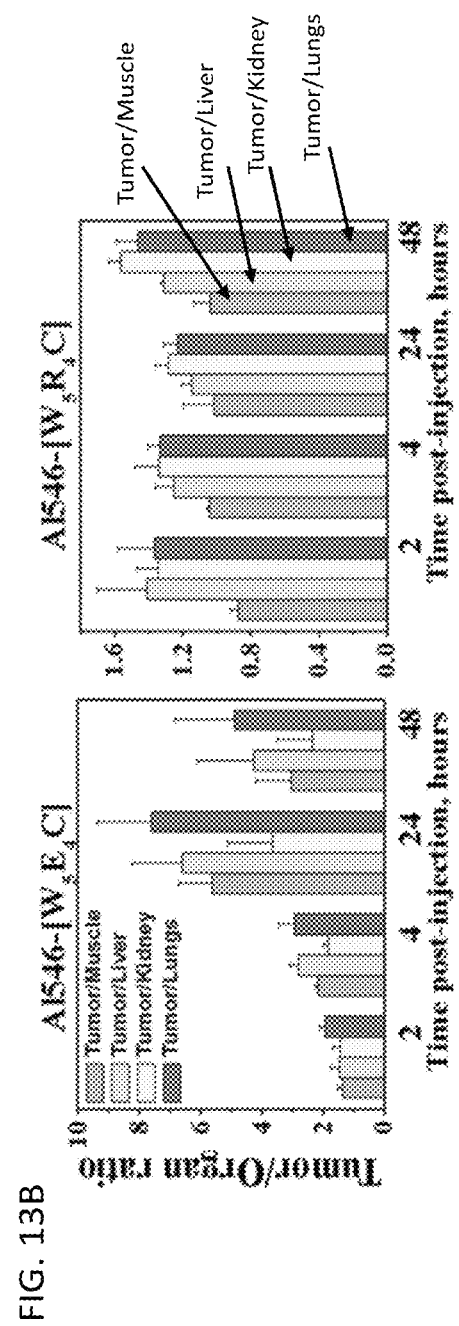
Figure 14:
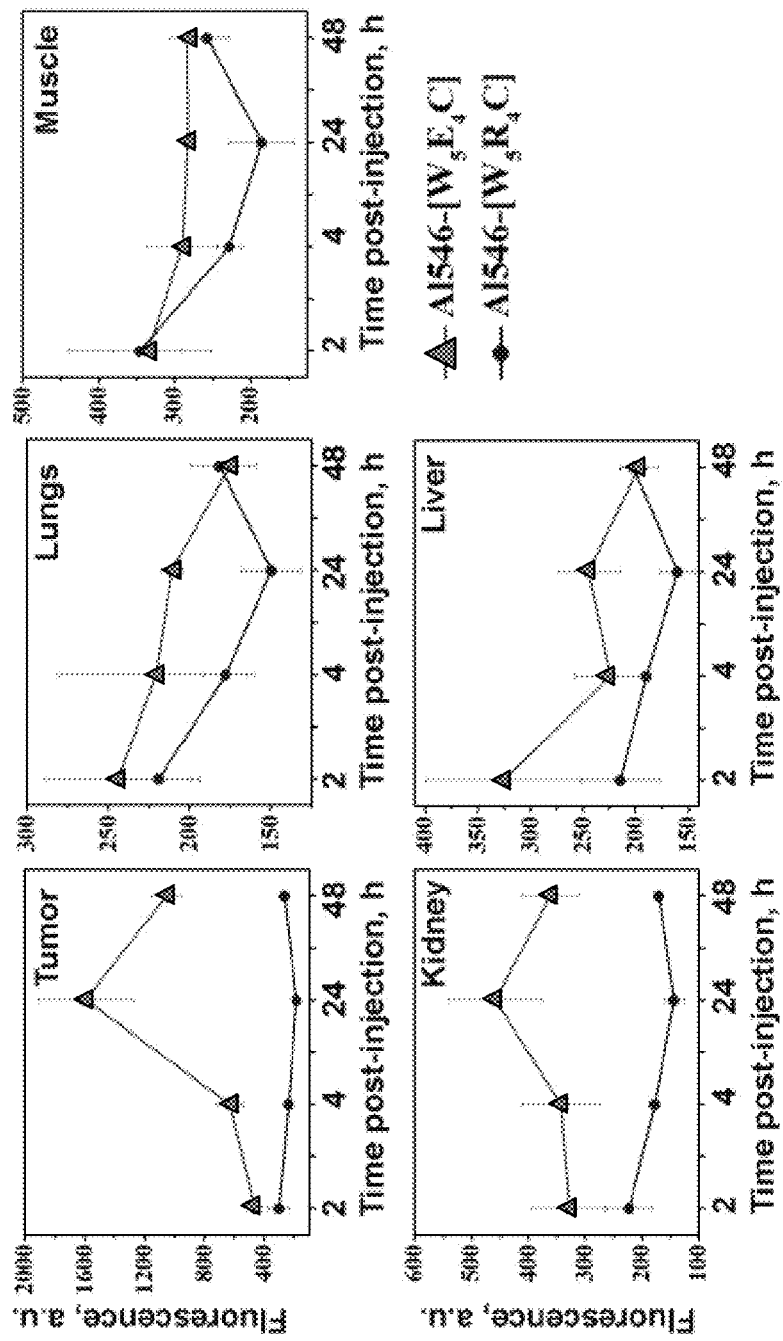
FIG. 14 is a set of graphs showing the kinetics of fluorescent signal changes in tumor, lungs, muscle, kidney and liver at different time points after IV administration of pH-sensitive, c[E$_4$W$_5$C] (SEQ ID NO: 5), and pH-insensitive, c[R$_4$W$_5$C] (SEQ ID NO: 219), cyclic peptides. This data supplements FIG. 13.

Side-by-side 4T1 tumor targeting and biodistribution investigation of asymmetric pH-sensitive, c[$E_4W_5$C] (SEQ ID NO: 5), and pH-insensitive, c[$R_4W_5$C] (SEQ ID NO: 219), peptides was also performed. A significant difference in tumor targeting was observed at all time points after IV administration of the constructs (FIG. 13A, note the difference in scale and FIG. 14). It is resulted in the significant difference between tumor/organ ratios for pH-sensitive and insensitive peptides (FIG. 13B and Table 9). The accumulation of the pH-insensitive peptide in tumor and other organs was very minimal. Tumor to organs ratios for pH-sensitive c[$E_4W_5$C] (SEQ ID NO: 5) peptide increases and reaches a maximum at 24 h post-injection. At the same time, tumor to organ ratios for pH-insensitive c[$R_4W_5$C] (SEQ ID NO: 219) peptide vary in the range of 0.8 to 1.6 values, which could be attributed to passive diffusion with blood flow.

TABLE 9

Tumor/Organ ratios shown on FIG. 13B.

| | Tumor/Muscle | Tumor/Liver | Tumor/Kidney | Tumor/Lung |
|---|---|---|---|---|
| A1546-c[$E_4W_5$C] | | | | |
| 2 hours | 1.39 ± 0.14 | 1.47 ± 0.30 | 1.45 ± 0.25 | 1.93 ± 0.19 |
| 4 hours | 2.19 ± 0.10 | 2.83 ± 0.26 | 1.86 ± 0.15 | 2.95 ± 0.51 |
| 24 hours | 5.64 ± 1.11 | 6.61 ± 1.62 | 3.66 ± 1.46 | 7.60 ± 1.77 |
| 48 hours | 3.05 ± 1.17 | 4.29 ± 1.85 | 2.37 ± 1.15 | 4.91 ± 1.94 |
| A1546-c[$R_4W_5$C] | | | | |
| 2 hours | 0.88 ± 0.04 | 1.42 ± 0.29 | 1.35 ± 0.12 | 1.37 ± 0.21 |
| 4 hours | 1.05 ± 0.01 | 1.26 ± 0.11 | 1.34 ± 0.14 | 1.34 ± 0.07 |
| 24 hours | 1.02 ± 0.18 | 1.15 ± 0.06 | 1.29 ± 0.07 | 1.24 ± 0.08 |
| 48 hours | 1.04 ± 0.10 | 1.31 ± 0.02 | 1.56 ± 0.07 | 1.47 ± 0.12 |

Figure 15:
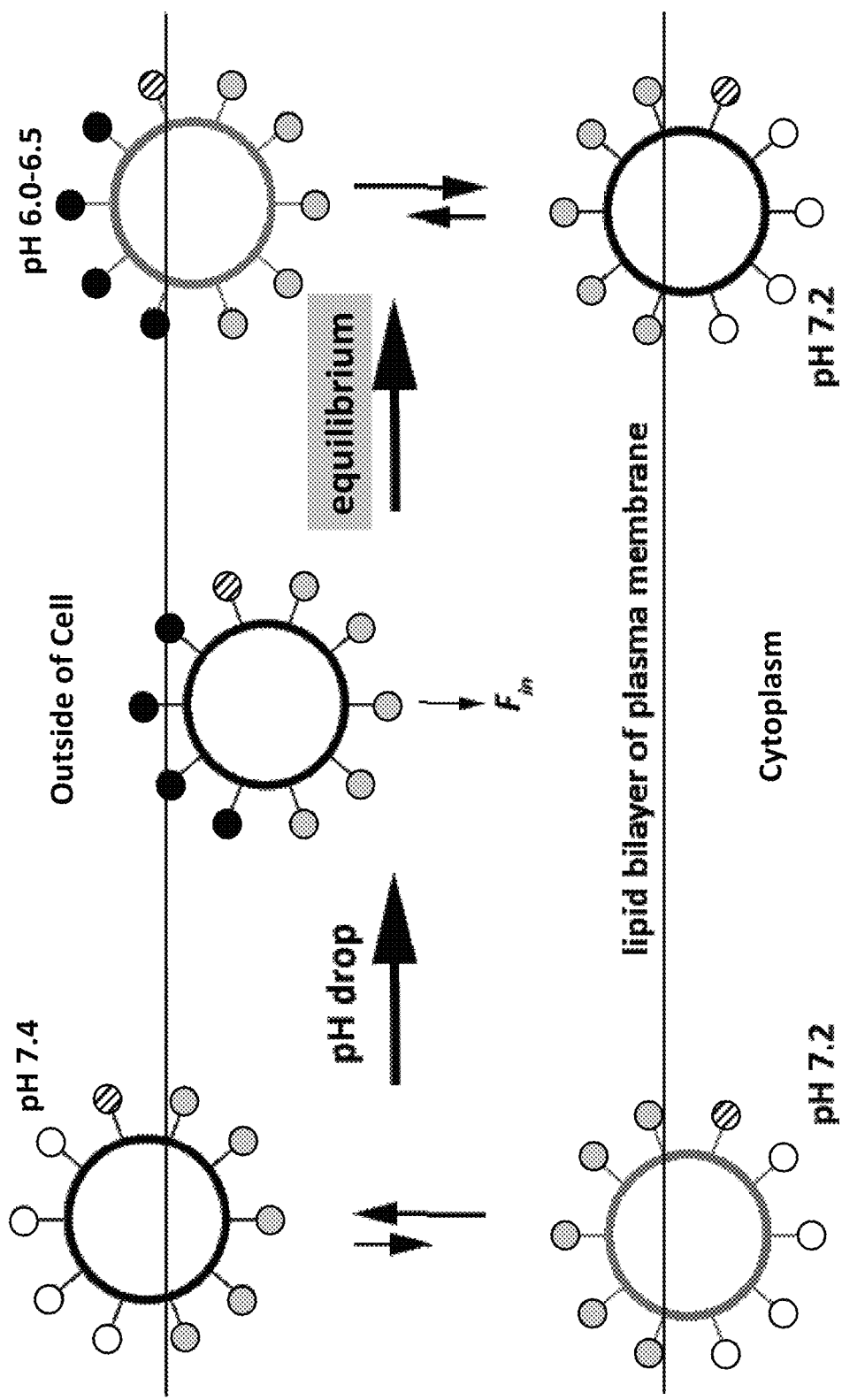
FIG. 15 is a cartoon illustrating peptide distribution between the outer and inner leaflets of the lipid bilayer of the membrane. At neutral and high pHs, Glu residues are negatively-charged (white circles). Trp residues (gray circles) interact with polar headgroups. Cys residues (e.g. patterned circles) could be directed into the bilayer or away depending on hydrophobic or hydrophilic cargo is conjugated with it. More cyclic peptides may be found on the outer monolayer of a cell membrane compared to the inner monolayer due to the small pH gradient (pHe=7.4 and pHi=7.2). A drop of the external pH leads to the protonation of Glu residues (black circles), which enhances peptide hydrophobicity and induces partitioning into the bilayer. In various embodiments, the cyclic peptides are not released from the membrane in to the cytoplasm, i.e., they remain within the membrane.
Figure 16:
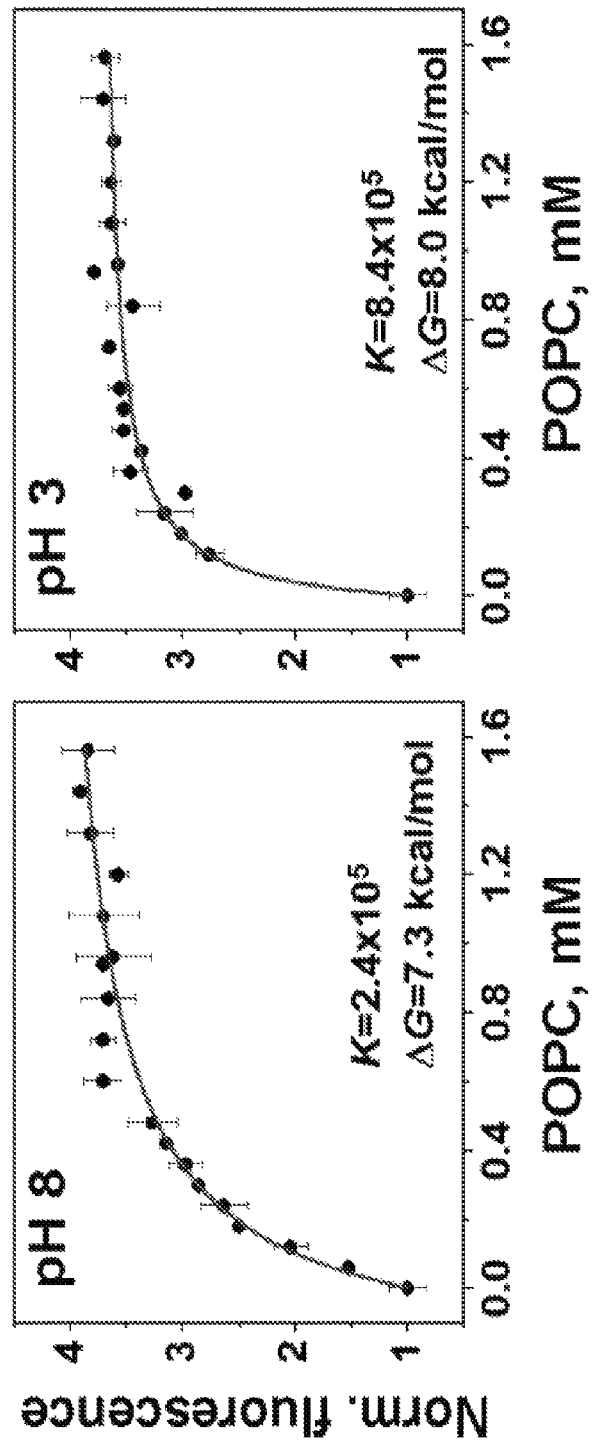
FIG. 16 is a set of graphs showing the partition of asymmetric cyclic c[E$_4$W$_5$C] (SEQ ID NO: 5) peptide in the lipid bilayer. The partitioning of an asymmetric cyclic c[E$_4$W$_5$C] (SEQ ID NO: 5) peptide to the lipid bilayer of POPC liposomes was investigated at high and low pHs. Nonlinear least squares curve fitting was performed using the Levenberg-Marquardt algorithm.
Figure 18:
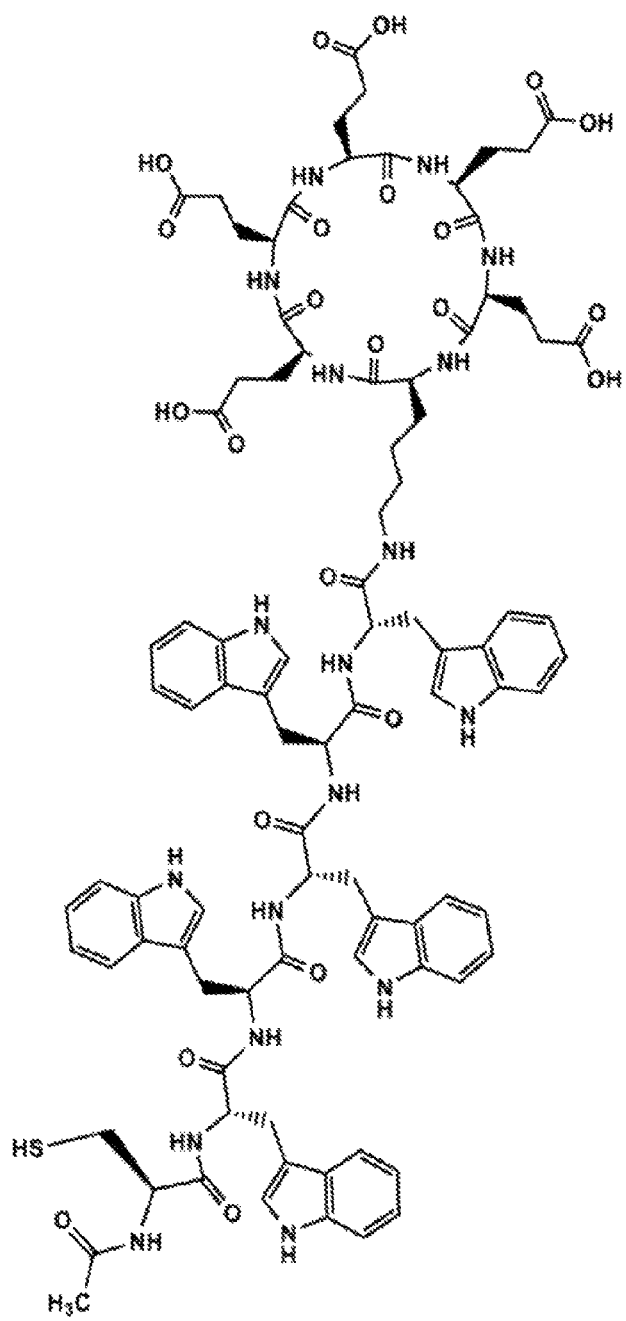
FIG. 18 shows an exemplary cyclic peptide with a tail. The exact mass and elemental analysis may vary depending on the specific isotopes that are present in a structure such as that shown in this figure.

The obtained data clearly indicated that tumor targeting by asymmetric c[$E_4W_5$C] (SEQ ID NO: 5) peptide is a pH-driven. However, the interaction of asymmetric cyclic peptide, c[$E_4W_5$C] (SEQ ID NO: 5), with membrane lipid bilayers has different mechanism compared to the action of linear pH-sensitive peptides (such as pHLIPs). Negatively charged Glu residues of asymmetric cyclic peptide are exposed to the aqueous solution at pH 8 and indole rings of Trp residues most probably interact with the lipid headgroups (FIG. 15). It was demonstrated previously that aromatic Trp has high affinity to lipid headgroups (Johansson A C & Lindahl E (2006) *Biophys J* 91(12):4450-4463; Killian J A & von Heijne G (2000) *Trends Biochem Sci* 25(9):429-434; van der Wel et al. (2007) *Biochemistry* 46(25):7514-7524; van der Wel et al. (2000) *Biochemistry* 39(11):3124-3133; MacCallum et al. (2008) *Biophys J* 94(9):3393-3404 33-36). The biophysical titration data provided herein indicate that c[$E_4W_5$C] (SEQ ID NO: 5) cyclic peptide partitions to the lipid bilayer at pH 8 and about 7.3 kcal/mol free Gibbs energy is released during the process (FIG. 16), which indicates on strong interactions of the peptide with membrane, which explains long-circulation time in mice. When pH is lowered, Glu residues are protonated. The pKa of protonation is higher due to the proximity to the hydrophobic membrane (Petkova et al. (1999) *Biochemistry* 38(5): 1562-1572; Harris T K & Turner G J (2002) *IUBMB Life* 53(2):85-98; Johansson A C & Lindahl E (2006) *Biophys J* 91(12):4450-4463; Karabadzhak et al. (2012) *Biophys J* 102(8):1846-1855). Protonation leads to the increase of hydrophobicity of the peptide, which promotes partition of the peptide into the bilayer. As a result, about 0.7 kcal/mol of additional free energy is released at low pH (FIG. 16), which is used to move cell-impermeable cargo, such as amanitin, across membrane and target acidic tumors. Because Trp residues have higher affinity to the headgroups region compared to the central hydrophobic part of the bilayer, the peptide is equilibrated in the region of headgroups between inner and outer leaflets of the bilayer. Reports have shown that pH equilibrates fast inside a liposome (Karabadzhak et al. (2012) *Biophys J* 102(8):1846-1855; Elamrani K & Blume A (1983) *Biochim Biophys Acta* 727(1):22-30). Thus, an equal amount of peptide molecules are distributed between both leaflets of the liposomal membrane with low pH outside and inside of it. However, in the case of cells, pH inside cells in healthy tissue and tumors is normal (around 7.2). At the same time, extracellular pH in the vicinity of cancer cells is low (6.2-6.5). Thus, peptides reaching inner leaflet of the bilayer might expose their Glu residues to the cytoplasm, where they would be de-protonated and became charged again. This would reduce the rate of the peptide diffusion back into the membrane and should lead to the shift of the equilibrium toward accumulation of the peptides at inner leaflet of bilayer of plasma membrane of cells (FIG. 15).

Thus, cyclic peptides could be considered as a weak acid with multiple protonated groups, which diffuse across the bilayer. For weak acids, the intracellular-extracellular distribution, $C_i/C_e$, should be calculated according to the following equation:

$$\frac{C_i}{C_e} = \frac{1 + 10^{pH_i - pK_a}}{1 + 10^{pH_e - pK_a}}$$

where $pH_i$ and $pH_e$ are the intracellular and extracellular pH values, respectively. Since the cyclic peptides have affinity to the membrane, $C_i$ and $C_e$ are considered as the concentrations of the peptide on inner and outer leaflets, respectively. pKa of membrane partition for the asymmetric cyclic peptide was established to be 5.7. The calculation shows that at pHe=7.4 (healthy tissue) and pHi=7.2 the concentration ratio on inner and outer leaflets for asymmetric cyclic peptides is 0.6. However, the same ratio increases to 4.5, 7.8, and 10.9 if extracellular pHe would be 6.5, 6.2 and 6.0, respectively. It is assumed that the symmetrical WE peptides have the same mechanism of action as asymmetric peptide, however they have less favorable localization of Trp and Glu residues, which in some instances may reduce their ability to accumulate at inner leaflet of bilayer of cellular membranes and target acidic tumors. Leu-containing peptides are less advantageous due to their reduced affinity to the headgroup part of the bilayer and high affinity to the center of the membrane.

The novel class of pH-sensitive cyclic peptides containing tryptophan and glutamic acid residues shows potential applications for targeting tumors and translocation of polar cargo molecules across the cell membrane.

This study shows that negatively charged pH-sensitive cyclic peptides (cyclic peptides) are useful for targeting acidic tumors and other pathological states associated with acidity. Additionally, the pH sensitivity of cyclic peptides makes them useful for diagnostic and cosmetic applications, e.g., modulation of dermal cells and tissues.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pH triggered cyclic peptide, wherein said cyclic peptide comprises the sequence c[E4W5C] (SEQ ID NO: 5).

2. The cyclic peptide of claim 1, (a) wherein the cyclic peptide has a net negative charge at a pH of about 7, 7.25, 7.5, or 7.75 in water; (b) wherein the cyclic peptide has an acid dissociation constant at logarithmic scale (pKa) of less than about 4.0, 4.5, 5.0, 5.5, 6.0, 6.5, or 7; (c) wherein less than 1, 2, 3, 4, or 5 of the amino acids in the cyclic peptide have a net positive charge at a pH of 7, 7.25, 7.5, or 7.75 in water; or (d) wherein the cyclic peptide comprises 0 amino acids having a net positive charge at a pH of about 7, 7.25, 7.5, or 7.75 in water.

3. The cyclic peptide of claim 1, comprising
   (i) 11, 12, 13, 14, 15, 16, 17, 18, 19, or 20 or more amino acids;
   (ii) 11 to 15 amino acids;
   (iii) 11 to 12 amino acids;
   (iv) less than about 20 amino acids;
   (v) less than 12, 13, 14, or 15 amino acids; or
   (vi) less than 15 amino acids.

4. The cyclic peptide of claim 1, comprising a functional group to which a cargo compound may be attached.

5. The cyclic peptide of claim 4, (a) wherein the functional group is a side chain of an amino acid of the cyclic peptide; (b) wherein the functional group is an amino acid side chain to which a cargo compound may be attached via a disulfide bond; (c) wherein the functional group to which a cargo compound may be attached comprises a free sulfhydryl (SH) or selenohydryl (SeH) group; (d) wherein the functional group comprises a cysteine, homocysteine, selenocysteine, or homoselenocysteine; or (e) wherein the functional group comprises a primary amine.

6. The cyclic peptide of claim 1, comprising about 6, 7, 8, 9, 10 or more aromatic amino acids.

7. The cyclic peptide of claim 6, wherein the aromatic amino acid is a tryptophan, a tyrosine, a phenylalanine, or an artificial aromatic amino acid.

8. The cyclic peptide of claim 1, comprising
   at least 5, 6, 7, 8, 9, 10 or more protonatable amino acids, wherein the protonatable amino acids comprise one or more of aspartic acid, glutamic acid, and gamma-carboxyglutamic acid.

9. The cyclic peptide of claim 8, comprising at least 5, 6, 7, 8, 9, 10 or more protonatable amino acids, wherein the protonatable amino acids comprise aspartic acid, glutamic acid, gamma-carboxyglutamic acid, or any combination thereof.

10. The cyclic peptide of claim 1, comprising at least 4, 5, 6, 7, 8, 9, 10, 11, 12, 13, 14, or 15 carboxyl groups.

11. The cyclic peptide of claim 1, comprising at least 1, 2, 3, 4, 5, 6, 7, 8, 9, 10, 11, 12, 13, 14, 15, 16, 17, 18, 19, or 20 artificial amino acids.

12. The cyclic peptide of claim 11, comprising at least 1, 2, 3, 4, 5, 6, 7, 8, 9, 10, 11, 12, 13, 14, 15, 16, 17, 18, 19, or 20 D-amino acids.

13. The cyclic peptide of claim 11, comprising at least 1 artificial amino acid, wherein the artificial amino acid is a cysteine derivative, an aspartic acid derivative, a glutamic acid derivative, a phenylalanine derivative, a tyrosine derivative, or a tryptophan derivative.

14. The cyclic peptide of claim 13, comprising
   (i) a cysteine derivative selected from the group consisting of D-Ethionine, Seleno-L-cystine, S-(2-Thiazolyl)-L-cysteine, and S-(4-Tolyl)-L-cysteine;
   (ii) an aspartic acid derivative which is a N-phenyl (benzyl)amino derivative of aspartic acid;
   (iii) a glutamic acid derivative selected from the group consisting of y-Carboxy-DL-glutamic acid, 4-Fluoro-DL-glutamic acid, and (4S)-4-(4-Trifluoromethyl-benzyl)-L-glutamic acid;
   (iv) a phenylalanine derivative selected from the group consisting of (S)-N-acetyl-4-bromophenylalanine, N-Acetyl-2-fluoro-DL-phenylalanine, N-Acetyl-4-fluoro-DL-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, 4-(Hydroxymethyl)-D-phenylalanine, N-(3-Indolylacetyl)-L-phenylalanine, p-Iodo-D-phenylalanine, a-Methyl-DL-phenylalanine, 4-Nitro-DL-phenylalanine, and 4-(Trifluoromethyl)-D-phenylalanine;
   (v) a tyrosine derivative selected from the group consisting of a-Methyl-DL-tyrosine, 3-Chloro-L-tyrosine, 3-Nitro-L-tyrosine, and DL-o-Tyrosine; and/or (vi) a tryptophan derivative selected from the group consisting of 5-Fluoro-L-tryptophan, 5-Fluoro-DL-tryptophan, 5-Hydroxy-L-tryptophan, 5-Methoxy-DL-tryptophan, or 5-Methyl-DL-tryptophan.

15. The cyclic peptide of claim 1, comprising at least 10 amino acids, wherein at least 6 of the at least 10 amino acids of said cyclic peptide are non-polar, and at least 1 or 2 of the at least 10 amino acids of said cyclic peptide is protonatable.

16. The cyclic peptide of claim 1, wherein the cyclic peptide is asymmetric on either side of an axis drawn from the functional group through the center of the cyclic peptide.

17. The cyclic peptide of claim 1, comprisinq the sequence c[XmYkZm], wherein,
   X is tryptophan, phenylalanine, tyrosine, or any combination thereof;
   Y is aspartic acid, glutamic acid, or any combination thereof;
   Z is a functional group to which a cargo compound may be attached;
   m is an integer from 1 to 5; and
   k is an integer from 1 to 10.

18. The cyclic peptide of claim 1, which is linked to a cargo compound.

19. The cyclic peptide of claim 1, which is directly linked to a cargo compound by a covalent bond.

20. The cyclic peptide of claim 18, wherein (a) the cargo has a weight of at least about 15 kDa; (b) the cargo is polar or nonpolar; (c) the cargo is a marker; (d) the cargo is a therapeutic, diagnostic, radiation-enhancing, radiation-sensitizing, imaging, gene regulation, cytotoxic, apoptotic, or research reagent; (e) the cargo comprises a dye, a fluorescent dye, a fluorescent protein, a nanoparticle, or a radioactive isotope; (f) the cargo comprises phalloidin, phallo toxin, amanitin toxin, a DNA intercalator, or a peptide nucleic acid; (g) the cargo comprises a magnetic resonance, positron emission tomography, x-ray contrast agent, single photon emission computed tomography, or fluorescence imaging agent; (h) the cargo is a compound that treats, reverses, or reduces, hair loss; or (i) the cargo is a chemotherapeutic compound.

21. The cyclic peptide of claim 4, comprising one or more cargo molecules attached to said functional group used as a therapeutic, diagnostic, imaging, immune activation, gene regulation or cell function regulation agent, radiation-enhancing agent, radiation-sensitizing agent, or as a research tool.

22. The cyclic peptide of claim 1, wherein 1 or more of the amino acid side chains of the cyclic peptide are chemically modified to be radioactive or detectable by probing radiation or wherein one or more atoms are replaced by a radioactive isotope or a stable isotope.

23. The cyclic peptide of claim 20, wherein the compound that treats, reverses, or reduces hair loss is a vasodilator, a 5-alpha-reductase inhibitor, finasteride, dutasteride, fluridil, spironolactone latanoprost, bimatoprost, minoxidil, tretinoin, ketoconazole, alfatradiol, topilutamide, or melatonin.

24. A method of treating a subject afflicted with hair loss comprising administering an effective amount of the cyclic peptide of claim 20 (h) to the scalp of the subject.

25. A diagnostic conjugate comprising the cyclic peptide of claim 1 and a pharmaceutically acceptable detectable marker linked thereto.

26. The cyclic peptide of claim 4, wherein the cargo compound is a cosmetic or antimicrobial compound.

27. A method for altering the appearance of skin or controlling a microbial infection of skin or mucous membrane comprising applying the cyclic peptide of claim 1 to the surface of the skin.

\* \* \* \* \*

UNITED STATES PATENT AND TRADEMARK OFFICE
CERTIFICATE OF CORRECTION

| | |
|---|---|
| PATENT NO. | : 11,274,126 B2 |
| APPLICATION NO. | : 16/087628 |
| DATED | : March 15, 2022 |
| INVENTOR(S) | : Yana K. Reshetnyak et al. |

It is certified that error appears in the above-identified patent and that said Letters Patent is hereby corrected as shown below:

In the Claims

Claim 17, Column 162, Line 30, replace "comprisinq" with --comprising--

Claim 20, Column 162, Line 57, delete the "," between "reduces" and "hair loss"

Signed and Sealed this
Twenty-fourth Day of May, 2022

Katherine Kelly Vidal
*Director of the United States Patent and Trademark Office*

SEQUENCE LISTING

```
<160> NUMBER OF SEQ ID NOS: 224

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Trp Glu Trp Glu Trp Glu Trp Cys
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Trp Glu Trp Glu Trp Glu Trp Glu Trp Cys
1               5                   10

<210> SEQ ID NO 3
<211> LENGTH: 12
<212> TYPE: PRT
<213> ORGANISM: Artificial Sequence
<220> FEATURE:
```

<223> OTHER INFORMATION: Synthetic construct

<400> SEQUENCE: 3

Trp Glu Trp Glu Trp Glu Trp Glu Trp Glu Trp Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct

<400> SEQUENCE: 4

Leu Glu Leu Glu Leu Glu Leu Glu Trp Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Glu Glu Glu Glu Trp Trp Trp Trp Trp Cys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Glu Glu Glu Trp Trp Trp Trp Trp Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Glu Trp Glu Trp Trp Trp Trp Glu Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

Glu Trp Trp Glu Trp Trp Trp Glu Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic construct

<400> SEQUENCE: 9

Glu Trp Trp Trp Glu Trp Trp Glu Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Glu Trp Trp Trp Trp Glu Trp Glu Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Glu Trp Trp Trp Trp Trp Glu Glu Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic construct

<400> SEQUENCE: 12

Glu Trp Glu Glu Trp Trp Trp Trp Cys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Glu Trp Trp Glu Glu Trp Trp Trp Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Glu Trp Trp Trp Glu Glu Trp Trp Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 15

Glu Trp Trp Trp Trp Glu Glu Trp Cys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Trp Glu Glu Glu Trp Trp Trp Trp Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Trp Trp Glu Glu Glu Trp Trp Trp Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Trp Trp Trp Glu Glu Glu Trp Trp Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic construct

<400> SEQUENCE: 19

Trp Trp Trp Trp Glu Glu Glu Trp Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic construct

<400> SEQUENCE: 20

Trp Glu Trp Glu Glu Trp Trp Trp Cys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic construct

<400> SEQUENCE: 21
```

```
Trp Glu Trp Trp Glu Glu Trp Trp Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Trp Glu Trp Trp Trp Glu Glu Trp Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic construct

<400> SEQUENCE: 23

Trp Glu Trp Trp Trp Trp Glu Glu Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic construct

<400> SEQUENCE: 24

Glu Glu Glu Trp Trp Trp Trp Trp
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic construct

<400> SEQUENCE: 25

Glu Trp Glu Trp Trp Trp Trp Glu
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic construct

<400> SEQUENCE: 26

Glu Trp Trp Glu Trp Trp Trp Glu
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic construct

<400> SEQUENCE: 27
```

```
Glu Trp Trp Trp Glu Trp Trp Glu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic construct

<400> SEQUENCE: 28

Glu Trp Trp Trp Trp Glu Trp Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic construct

<400> SEQUENCE: 29

Glu Trp Trp Trp Trp Trp Glu Glu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct

<400> SEQUENCE: 30

Glu Trp Glu Glu Trp Trp Trp Trp
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic construct

<400> SEQUENCE: 31

Glu Trp Trp Glu Glu Trp Trp Trp
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct

<400> SEQUENCE: 32

Glu Trp Trp Trp Glu Glu Trp Trp
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic construct

<400> SEQUENCE: 33

Glu Trp Trp Trp Trp Glu Glu Trp
```

```
1               5
```

<210> SEQ ID NO 34
<211> LENGTH: 8
<212> TYPE: PRT
<213> ORGANISM: Artificial Sequence
<220> FEATURE:
<223> OTHER INFORMATION: Synthetic construct

<400> SEQUENCE: 34

```
Trp Glu Glu Glu Trp Trp Trp Trp
1               5
```

<210> SEQ ID NO 35
<211> LENGTH: 8
<212> TYPE: PRT
<213> ORGANISM: Artificial Sequence
<220> FEATURE:
<223> OTHER INFORMATION: Synthetic construct

<400> SEQUENCE: 35

```
Trp Trp Glu Glu Glu Trp Trp Trp
1               5
```

<210> SEQ ID NO 36
<211> LENGTH: 8
<212> TYPE: PRT
<213> ORGANISM: Artificial Sequence
<220> FEATURE:
<223> OTHER INFORMATION: Synthetic construct

<400> SEQUENCE: 36

```
Trp Trp Trp Glu Glu Glu Trp Trp
1               5
```

<210> SEQ ID NO 37
<211> LENGTH: 8
<212> TYPE: PRT
<213> ORGANISM: Artificial Sequence
<220> FEATURE:
<223> OTHER INFORMATION: Synthetic construct

<400> SEQUENCE: 37

```
Trp Trp Trp Trp Glu Glu Glu Trp
1               5
```

<210> SEQ ID NO 38
<211> LENGTH: 8
<212> TYPE: PRT
<213> ORGANISM: Artificial Sequence
<220> FEATURE:
<223> OTHER INFORMATION: Synthetic construct

<400> SEQUENCE: 38

```
Trp Glu Trp Glu Glu Trp Trp Trp
1               5
```

<210> SEQ ID NO 39
<211> LENGTH: 8
<212> TYPE: PRT
<213> ORGANISM: Artificial Sequence
<220> FEATURE:
<223> OTHER INFORMATION: Synthetic construct

<400> SEQUENCE: 39

```
Trp Glu Trp Trp Glu Glu Trp Trp
1               5
```

```
<210> SEQ ID NO 40
<211> LENGTH: 8
<212> TYPE: PRT
<213> ORGANISM: Artificial Sequence
<220> FEATURE:
<223> OTHER INFORMATION: Synthetic construct

<400> SEQUENCE: 40

Trp Glu Trp Trp Trp Glu Glu Trp
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic construct

<400> SEQUENCE: 41

Trp Glu Trp Trp Trp Trp Glu Glu
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

Asp Asp Asp Trp Trp Trp Trp Trp Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic construct

<400> SEQUENCE: 43

Asp Trp Asp Trp Trp Trp Trp Asp Cys
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic construct

<400> SEQUENCE: 44

Asp Trp Trp Asp Trp Trp Trp Asp Cys
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic construct

<400> SEQUENCE: 45

Asp Trp Trp Trp Asp Trp Trp Asp Cys
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic construct

<400> SEQUENCE: 46

Asp Trp Trp Trp Trp Asp Trp Asp Cys
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic construct

<400> SEQUENCE: 47

Asp Trp Trp Trp Trp Trp Asp Asp Cys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic construct

<400> SEQUENCE: 48

Asp Trp Asp Asp Trp Trp Trp Trp Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic construct

<400> SEQUENCE: 49

Asp Trp Trp Asp Asp Trp Trp Trp Cys
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic construct

<400> SEQUENCE: 50

Asp Trp Trp Trp Asp Asp Trp Trp Cys
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic construct

<400> SEQUENCE: 51

Asp Trp Trp Trp Trp Asp Asp Trp Cys
1               5

```
<210> SEQ ID NO 52
<211> LENGTH: 9
<212> TYPE: PRT
<213> ORGANISM: Artificial Sequence
<220> FEATURE:
<223> OTHER INFORMATION: Synthetic construct

<400> SEQUENCE: 52

Trp Asp Asp Asp Trp Trp Trp Trp Cys
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic construct

<400> SEQUENCE: 53

Trp Trp Asp Asp Asp Trp Trp Trp Cys
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic construct

<400> SEQUENCE: 54

Trp Trp Trp Asp Asp Asp Trp Trp Cys
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic construct

<400> SEQUENCE: 55

Trp Trp Trp Trp Asp Asp Asp Trp Cys
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic construct

<400> SEQUENCE: 56

Trp Asp Trp Asp Asp Trp Trp Trp Cys
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic construct

<400> SEQUENCE: 57

Trp Asp Trp Trp Asp Asp Trp Trp Cys
1               5

<210> SEQ ID NO 58
```

<211> LENGTH: 9
<212> TYPE: PRT
<213> ORGANISM: Artificial Sequence
<220> FEATURE:
<223> OTHER INFORMATION: Synthetic construct

<400> SEQUENCE: 58

Trp Asp Trp Trp Trp Asp Asp Trp Cys
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic construct

<400> SEQUENCE: 59

Trp Asp Trp Trp Trp Trp Asp Asp Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic construct

<400> SEQUENCE: 60

Asp Asp Asp Trp Trp Trp Trp Trp
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic construct

<400> SEQUENCE: 61

Asp Trp Asp Trp Trp Trp Trp Asp
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic construct

<400> SEQUENCE: 62

Asp Trp Trp Asp Trp Trp Trp Asp
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic construct

<400> SEQUENCE: 63

Asp Trp Trp Trp Asp Trp Trp Asp
1               5

<210> SEQ ID NO 64
<211> LENGTH: 8

```
<212> TYPE: PRT
<213> ORGANISM: Artificial Sequence
<220> FEATURE:
<223> OTHER INFORMATION: Synthetic construct

<400> SEQUENCE: 64

Asp Trp Trp Trp Trp Asp Trp Asp
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic construct

<400> SEQUENCE: 65

Asp Trp Trp Trp Trp Trp Asp Asp
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic construct

<400> SEQUENCE: 66

Asp Trp Asp Asp Trp Trp Trp Trp
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic construct

<400> SEQUENCE: 67

Asp Trp Trp Asp Asp Trp Trp Trp
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic construct

<400> SEQUENCE: 68

Asp Trp Trp Trp Asp Asp Trp Trp
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic construct

<400> SEQUENCE: 69

Asp Trp Trp Trp Trp Asp Asp Trp
1               5

<210> SEQ ID NO 70
<211> LENGTH: 8
<212> TYPE: PRT
```

```
<213> ORGANISM: Artificial Sequence
<220> FEATURE:
<223> OTHER INFORMATION: Synthetic construct

<400> SEQUENCE: 70

Trp Asp Asp Asp Trp Trp Trp Trp
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic construct

<400> SEQUENCE: 71

Trp Trp Asp Asp Asp Trp Trp Trp
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic construct

<400> SEQUENCE: 72

Trp Trp Trp Asp Asp Asp Trp Trp
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic construct

<400> SEQUENCE: 73

Trp Trp Trp Trp Asp Asp Asp Trp
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic construct

<400> SEQUENCE: 74

Trp Asp Trp Asp Asp Trp Trp Trp
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic construct

<400> SEQUENCE: 75

Trp Asp Trp Trp Asp Asp Trp Trp
1               5

<210> SEQ ID NO 76
<211> LENGTH: 8
<212> TYPE: PRT
<213> ORGANISM: Artificial Sequence
```

```
<220> FEATURE:
<223> OTHER INFORMATION: Synthetic construct

<400> SEQUENCE: 76

Trp Asp Trp Trp Trp Asp Asp Trp
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic construct

<400> SEQUENCE: 77

Trp Asp Trp Trp Trp Trp Asp Asp
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(3)
<223> OTHER INFORMATION: X= gamma-carboxyglutamic acid

<400> SEQUENCE: 78

Xaa Xaa Xaa Trp Trp Trp Trp Trp
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (3)..(3)
<223> OTHER INFORMATION: X= gamma-carboxyglutamic acid
<220> FEATURE:
<221> NAME/KEY: MOD_RES
<222> LOCATION: (8)..(8)
<223> OTHER INFORMATION: X= gamma-carboxyglutamic acid

<400> SEQUENCE: 79

Xaa Trp Xaa Trp Trp Trp Trp Xaa
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (4)..(4)
<223> OTHER INFORMATION: X= gamma-carboxyglutamic acid
<220> FEATURE:
```

```
<221> NAME/KEY: MOD_RES
<222> LOCATION: (8)..(8)
<223> OTHER INFORMATION: X= gamma-carboxyglutamic acid

<400> SEQUENCE: 80

Xaa Trp Trp Xaa Trp Trp Trp Xaa
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (5)..(5)
<223> OTHER INFORMATION: X= gamma-carboxyglutamic acid
<220> FEATURE:
<221> NAME/KEY: MOD_RES
<222> LOCATION: (8)..(8)
<223> OTHER INFORMATION: X= gamma-carboxyglutamic acid

<400> SEQUENCE: 81

Xaa Trp Trp Trp Xaa Trp Trp Xaa
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (6)..(6)
<223> OTHER INFORMATION: X= gamma-carboxyglutamic acid
<220> FEATURE:
<221> NAME/KEY: MOD_RES
<222> LOCATION: (8)..(8)
<223> OTHER INFORMATION: X= gamma-carboxyglutamic acid

<400> SEQUENCE: 82

Xaa Trp Trp Trp Trp Xaa Trp Xaa
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (7)..(8)
<223> OTHER INFORMATION: X= gamma-carboxyglutamic acid

<400> SEQUENCE: 83

Xaa Trp Trp Trp Trp Trp Xaa Xaa
1               5
```

```
<210> SEQ ID NO 84
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (3)..(4)
<223> OTHER INFORMATION: X= gamma-carboxyglutamic acid

<400> SEQUENCE: 84

Xaa Trp Xaa Xaa Trp Trp Trp Trp
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (4)..(5)
<223> OTHER INFORMATION: X= gamma-carboxyglutamic acid

<400> SEQUENCE: 85

Xaa Trp Trp Xaa Xaa Trp Trp Trp
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (5)..(6)
<223> OTHER INFORMATION: X= gamma-carboxyglutamic acid

<400> SEQUENCE: 86

Xaa Trp Trp Trp Xaa Xaa Trp Trp
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (6)..(7)
<223> OTHER INFORMATION: X= gamma-carboxyglutamic acid
```

<400> SEQUENCE: 87

Xaa Trp Trp Trp Trp Xaa Xaa Trp
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(4)
<223> OTHER INFORMATION: X= gamma-carboxyglutamic acid

<400> SEQUENCE: 88

Trp Xaa Xaa Xaa Trp Trp Trp Trp
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (3)..(5)
<223> OTHER INFORMATION: X= gamma-carboxyglutamic acid

<400> SEQUENCE: 89

Trp Trp Xaa Xaa Xaa Trp Trp Trp
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (4)..(6)
<223> OTHER INFORMATION: X= gamma-carboxyglutamic acid

<400> SEQUENCE: 90

Trp Trp Trp Xaa Xaa Xaa Trp Trp
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (5)..(7)
<223> OTHER INFORMATION: X= gamma-carboxyglutamic acid

<400> SEQUENCE: 91

Trp Trp Trp Trp Xaa Xaa Xaa Trp
1               5

<210> SEQ ID NO 92
<211> LENGTH: 8
<212> TYPE: PRT
<213> ORGANISM: Artificial Sequence

```
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (4)..(5)
<223> OTHER INFORMATION: X= gamma-carboxyglutamic acid

<400> SEQUENCE: 92

Trp Xaa Trp Xaa Xaa Trp Trp Trp
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (5)..(6)
<223> OTHER INFORMATION: X= gamma-carboxyglutamic acid

<400> SEQUENCE: 93

Trp Xaa Trp Trp Xaa Xaa Trp Trp
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (6)..(7)
<223> OTHER INFORMATION: X= gamma-carboxyglutamic acid

<400> SEQUENCE: 94

Trp Xaa Trp Trp Trp Xaa Xaa Trp
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (7)..(8)
<223> OTHER INFORMATION: X= gamma-carboxyglutamic acid

<400> SEQUENCE: 95

Trp Xaa Trp Trp Trp Trp Xaa Xaa
1               5
```

<210> SEQ ID NO 96
<211> LENGTH: 8
<212> TYPE: PRT
<213> ORGANISM: Artificial Sequence
<220> FEATURE:
<223> OTHER INFORMATION: Synthetic construct

<400> SEQUENCE: 96

Glu Glu Glu Trp Trp Trp Trp Cys
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic construct

<400> SEQUENCE: 97

Glu Trp Glu Trp Trp Trp Glu Cys
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic construct

<400> SEQUENCE: 98

Glu Trp Trp Glu Trp Trp Glu Cys
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic construct

<400> SEQUENCE: 99

Glu Trp Trp Trp Glu Trp Glu Cys
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic construct

<400> SEQUENCE: 100

Glu Trp Trp Trp Trp Glu Glu Cys
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic construct

<400> SEQUENCE: 101

Glu Trp Glu Glu Trp Trp Trp Cys
1               5

```
<210> SEQ ID NO 102
<211> LENGTH: 8
<212> TYPE: PRT
<213> ORGANISM: Artificial Sequence
<220> FEATURE:
<223> OTHER INFORMATION: Synthetic construct

<400> SEQUENCE: 102

Glu Trp Trp Glu Glu Trp Trp Cys
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic construct

<400> SEQUENCE: 103

Glu Trp Trp Trp Glu Glu Trp Cys
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic construct

<400> SEQUENCE: 104

Glu Trp Trp Trp Trp Glu Glu Cys
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic construct

<400> SEQUENCE: 105

Trp Glu Glu Glu Trp Trp Trp Cys
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic construct

<400> SEQUENCE: 106

Trp Trp Glu Glu Glu Trp Trp Cys
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic construct

<400> SEQUENCE: 107

Trp Trp Trp Glu Glu Glu Trp Cys
1               5

<210> SEQ ID NO 108
```

<211> LENGTH: 8
<212> TYPE: PRT
<213> ORGANISM: Artificial Sequence
<220> FEATURE:
<223> OTHER INFORMATION: Synthetic construct

<400> SEQUENCE: 108

Trp Trp Trp Trp Glu Glu Glu Cys
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic construct

<400> SEQUENCE: 109

Trp Glu Trp Glu Glu Trp Trp Cys
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic construct

<400> SEQUENCE: 110

Trp Glu Trp Trp Glu Glu Trp Cys
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic construct

<400> SEQUENCE: 111

Trp Glu Trp Trp Trp Glu Glu Cys
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic construct

<400> SEQUENCE: 112

Glu Glu Glu Trp Trp Trp Trp
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic construct

<400> SEQUENCE: 113

Glu Trp Glu Trp Trp Trp Glu
1               5

<210> SEQ ID NO 114
<211> LENGTH: 7

<212> TYPE: PRT
<213> ORGANISM: Artificial Sequence
<220> FEATURE:
<223> OTHER INFORMATION: Synthetic construct

<400> SEQUENCE: 114

Glu Trp Trp Glu Trp Trp Glu
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic construct

<400> SEQUENCE: 115

Glu Trp Trp Trp Glu Trp Glu
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic construct

<400> SEQUENCE: 116

Glu Trp Trp Trp Trp Glu Glu
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic construct

<400> SEQUENCE: 117

Glu Trp Glu Glu Trp Trp Trp
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic construct

<400> SEQUENCE: 118

Glu Trp Trp Glu Glu Trp Trp
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic construct

<400> SEQUENCE: 119

Glu Trp Trp Trp Glu Glu Trp
1               5

<210> SEQ ID NO 120
<211> LENGTH: 7
<212> TYPE: PRT

<213> ORGANISM: Artificial Sequence
<220> FEATURE:
<223> OTHER INFORMATION: Synthetic construct

<400> SEQUENCE: 120

Glu Trp Trp Trp Trp Glu Glu
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic construct

<400> SEQUENCE: 121

Trp Glu Glu Glu Trp Trp Trp
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic construct

<400> SEQUENCE: 122

Trp Trp Glu Glu Glu Trp Trp
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic construct

<400> SEQUENCE: 123

Trp Trp Trp Glu Glu Glu Trp
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic construct

<400> SEQUENCE: 124

Trp Trp Trp Trp Glu Glu Glu
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct

<400> SEQUENCE: 125

Trp Glu Trp Glu Glu Trp Trp
1               5

<210> SEQ ID NO 126
<211> LENGTH: 7
<212> TYPE: PRT
<213> ORGANISM: Artificial Sequence

```
<220> FEATURE:
<223> OTHER INFORMATION: Synthetic construct

<400> SEQUENCE: 126

Trp Glu Trp Trp Glu Glu Trp
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic construct

<400> SEQUENCE: 127

Trp Glu Trp Trp Trp Glu Glu
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic construct

<400> SEQUENCE: 128

Asp Asp Asp Trp Trp Trp Trp Cys
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic construct

<400> SEQUENCE: 129

Asp Trp Asp Trp Trp Trp Asp Cys
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic construct

<400> SEQUENCE: 130

Asp Trp Trp Asp Trp Trp Asp Cys
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic construct

<400> SEQUENCE: 131

Asp Trp Trp Trp Asp Trp Asp Cys
1               5

<210> SEQ ID NO 132
<211> LENGTH: 8
<212> TYPE: PRT
<213> ORGANISM: Artificial Sequence
<220> FEATURE:
```

<223> OTHER INFORMATION: Synthetic construct

<400> SEQUENCE: 132

Asp Trp Trp Trp Trp Asp Asp Cys
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic construct

<400> SEQUENCE: 133

Asp Trp Asp Asp Trp Trp Trp Cys
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic construct

<400> SEQUENCE: 134

Asp Trp Trp Asp Asp Trp Trp Cys
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic construct

<400> SEQUENCE: 135

Asp Trp Trp Trp Asp Asp Trp Cys
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic construct

<400> SEQUENCE: 136

Asp Trp Trp Trp Trp Asp Asp Cys
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic construct

<400> SEQUENCE: 137

Trp Asp Asp Asp Trp Trp Trp Cys
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic construct

<400> SEQUENCE: 138

Trp Trp Asp Asp Asp Trp Trp Cys
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic construct

<400> SEQUENCE: 139

Trp Trp Trp Asp Asp Asp Trp Cys
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic construct

<400> SEQUENCE: 140

Trp Trp Trp Trp Asp Asp Asp Cys
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic construct

<400> SEQUENCE: 141

Trp Asp Trp Asp Asp Trp Trp Cys
1               5

<210> SEQ ID NO 142
<211> LENGTH: 8
<212> TYPE: PRT
<213> ORGANISM: Artificial Sequence
<220> FEATURE:
<223> OTHER INFORMATION: Synthetic construct

<400> SEQUENCE: 142

Trp Asp Trp Trp Asp Asp Trp Cys
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic construct

<400> SEQUENCE: 143

Trp Asp Trp Trp Trp Asp Asp Cys
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 144

Asp Asp Asp Trp Trp Trp Trp
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic construct

<400> SEQUENCE: 145

Asp Trp Asp Trp Trp Trp Asp
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic construct

<400> SEQUENCE: 146

Asp Trp Trp Asp Trp Trp Asp
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic construct

<400> SEQUENCE: 147

Asp Trp Trp Trp Asp Trp Asp
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic construct

<400> SEQUENCE: 148

Asp Trp Trp Trp Trp Asp Asp
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic construct

<400> SEQUENCE: 149

Asp Trp Asp Asp Trp Trp Trp
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic construct

<400> SEQUENCE: 150
```

```
Asp Trp Trp Asp Asp Trp Trp
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic construct

<400> SEQUENCE: 151

Asp Trp Trp Trp Asp Asp Trp
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic construct

<400> SEQUENCE: 152

Asp Trp Trp Trp Trp Asp Asp
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic construct

<400> SEQUENCE: 153

Trp Asp Asp Asp Trp Trp Trp
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic construct

<400> SEQUENCE: 154

Trp Trp Asp Asp Asp Trp Trp
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic construct

<400> SEQUENCE: 155

Trp Trp Trp Asp Asp Asp Trp
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic construct

<400> SEQUENCE: 156
```

```
Trp Trp Trp Trp Asp Asp Asp
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic construct

<400> SEQUENCE: 157

Trp Asp Trp Asp Asp Trp Trp
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic construct

<400> SEQUENCE: 158

Trp Asp Trp Trp Asp Asp Trp
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic construct

<400> SEQUENCE: 159

Trp Asp Trp Trp Trp Asp Asp
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(3)
<223> OTHER INFORMATION: X= gamma-carboxyglutamic acid

<400> SEQUENCE: 160

Xaa Xaa Xaa Trp Trp Trp Trp
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (3)..(3)
<223> OTHER INFORMATION: X= gamma-carboxyglutamic acid
<220> FEATURE:
<221> NAME/KEY: MOD_RES
<222> LOCATION: (7)..(7)
<223> OTHER INFORMATION: X= gamma-carboxyglutamic acid
```

<400> SEQUENCE: 161

Xaa Trp Xaa Trp Trp Trp Xaa
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (4)..(4)
<223> OTHER INFORMATION: X= gamma-carboxyglutamic acid
<220> FEATURE:
<221> NAME/KEY: MOD_RES
<222> LOCATION: (7)..(7)
<223> OTHER INFORMATION: X= gamma-carboxyglutamic acid

<400> SEQUENCE: 162

Xaa Trp Trp Xaa Trp Trp Xaa
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (5)..(5)
<223> OTHER INFORMATION: X= gamma-carboxyglutamic acid
<220> FEATURE:
<221> NAME/KEY: MOD_RES
<222> LOCATION: (7)..(7)
<223> OTHER INFORMATION: X= gamma-carboxyglutamic acid

<400> SEQUENCE: 163

Xaa Trp Trp Trp Xaa Trp Xaa
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (6)..(7)
<223> OTHER INFORMATION: X= gamma-carboxyglutamic acid

<400> SEQUENCE: 164

Xaa Trp Trp Trp Trp Xaa Xaa
1               5

<210> SEQ ID NO 165
<211> LENGTH: 7

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (3)..(4)
<223> OTHER INFORMATION: X= gamma-carboxyglutamic acid

<400> SEQUENCE: 165

Xaa Trp Xaa Xaa Trp Trp Trp
1               5

<210> SEQ ID NO 166
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (4)..(5)
<223> OTHER INFORMATION: X= gamma-carboxyglutamic acid

<400> SEQUENCE: 166

Xaa Trp Trp Xaa Xaa Trp Trp
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (5)..(6)
<223> OTHER INFORMATION: X= gamma-carboxyglutamic acid

<400> SEQUENCE: 167

Xaa Trp Trp Trp Xaa Xaa Trp
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (6)..(7)
<223> OTHER INFORMATION: X= gamma-carboxyglutamic acid

<400> SEQUENCE: 168

Xaa Trp Trp Trp Trp Xaa Xaa
```

```
1               5
```

<210> SEQ ID NO 169
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(4)
<223> OTHER INFORMATION: X= gamma-carboxyglutamic acid

<400> SEQUENCE: 169

```
Trp Xaa Xaa Xaa Trp Trp Trp
1               5
```

<210> SEQ ID NO 170
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (3)..(5)
<223> OTHER INFORMATION: X= gamma-carboxyglutamic acid

<400> SEQUENCE: 170

```
Trp Trp Xaa Xaa Xaa Trp Trp
1               5
```

<210> SEQ ID NO 171
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (4)..(6)
<223> OTHER INFORMATION: X= gamma-carboxyglutamic acid

<400> SEQUENCE: 171

```
Trp Trp Trp Xaa Xaa Xaa Trp
1               5
```

<210> SEQ ID NO 172
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (5)..(7)
<223> OTHER INFORMATION: X= gamma-carboxyglutamic acid

<400> SEQUENCE: 172

```
Trp Trp Trp Trp Xaa Xaa Xaa
1               5
```

<210> SEQ ID NO 173
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES

```
<222> LOCATION: (2)..(2)
<223> OTHER INFORMATION: X= gamma-carboxyglutamic acid
<220> FEATURE:
<221> NAME/KEY: MOD_RES
<222> LOCATION: (4)..(5)
<223> OTHER INFORMATION: X= gamma-carboxyglutamic acid

<400> SEQUENCE: 173

Trp Xaa Trp Xaa Xaa Trp Trp
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (5)..(6)
<223> OTHER INFORMATION: X= gamma-carboxyglutamic acid

<400> SEQUENCE: 174

Trp Xaa Trp Trp Xaa Xaa Trp
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (6)..(7)
<223> OTHER INFORMATION: X= gamma-carboxyglutamic acid

<400> SEQUENCE: 175

Trp Xaa Trp Trp Trp Xaa Xaa
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic construct

<400> SEQUENCE: 176

Trp Glu Trp Glu Trp Glu Trp Cys
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic construct

<400> SEQUENCE: 177

Glu Trp Glu Trp Glu Trp Trp Cys
1               5
```

```
<210> SEQ ID NO 178
<211> LENGTH: 8
<212> TYPE: PRT
<213> ORGANISM: Artificial Sequence
<220> FEATURE:
<223> OTHER INFORMATION: Synthetic construct

<400> SEQUENCE: 178

Trp Asp Trp Asp Trp Asp Trp Cys
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic construct

<400> SEQUENCE: 179

Asp Trp Asp Trp Asp Trp Trp Cys
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (4)..(4)
<223> OTHER INFORMATION: X= gamma-carboxyglutamic acid
<220> FEATURE:
<221> NAME/KEY: MOD_RES
<222> LOCATION: (6)..(6)
<223> OTHER INFORMATION: X= gamma-carboxyglutamic acid

<400> SEQUENCE: 180

Trp Xaa Trp Xaa Trp Xaa Trp Cys
1               5

<210> SEQ ID NO 181
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X= gamma-carboxyglutamic acid
<220> FEATURE:
<221> NAME/KEY: MOD_RES
<222> LOCATION: (3)..(3)
<223> OTHER INFORMATION: X= gamma-carboxyglutamic acid
<220> FEATURE:
<221> NAME/KEY: MOD_RES
<222> LOCATION: (5)..(5)
<223> OTHER INFORMATION: X= gamma-carboxyglutamic acid

<400> SEQUENCE: 181

Xaa Trp Xaa Trp Xaa Trp Trp Cys
1               5

<210> SEQ ID NO 182
```

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 182

Trp Glu Trp Glu Trp Glu Trp Glu
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic construct

<400> SEQUENCE: 183

Glu Trp Glu Trp Glu Trp Glu Trp
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic construct

<400> SEQUENCE: 184

Trp Asp Trp Asp Trp Asp Trp Asp
1               5

<210> SEQ ID NO 185
<211> LENGTH: 8
<212> TYPE: PRT
<213> ORGANISM: Artificial Sequence
<220> FEATURE:
<223> OTHER INFORMATION: Synthetic construct

<400> SEQUENCE: 185

Asp Trp Asp Trp Asp Trp Asp Trp
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X=gamma-carboxyglutamic acid
<220> FEATURE:
<221> NAME/KEY: MOD_RES
<222> LOCATION: (4)..(4)
<223> OTHER INFORMATION: X=gamma-carboxyglutamic acid
<220> FEATURE:
<221> NAME/KEY: MOD_RES
<222> LOCATION: (6)..(6)
<223> OTHER INFORMATION: X=gamma-carboxyglutamic acid
<220> FEATURE:
<221> NAME/KEY: MOD_RES
<222> LOCATION: (8)..(8)
<223> OTHER INFORMATION: X=gamma-carboxyglutamic acid

<400> SEQUENCE: 186

Trp Xaa Trp Xaa Trp Xaa Trp Xaa
1               5
```

```
<210> SEQ ID NO 187
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X=gamma-carboxyglutamic acid
<220> FEATURE:
<221> NAME/KEY: MOD_RES
<222> LOCATION: (3)..(3)
<223> OTHER INFORMATION: X=gamma-carboxyglutamic acid
<220> FEATURE:
<221> NAME/KEY: MOD_RES
<222> LOCATION: (5)..(5)
<223> OTHER INFORMATION: X=gamma-carboxyglutamic acid
<220> FEATURE:
<221> NAME/KEY: MOD_RES
<222> LOCATION: (7)..(7)
<223> OTHER INFORMATION: X=gamma-carboxyglutamic acid

<400> SEQUENCE: 187

Xaa Trp Xaa Trp Xaa Trp Xaa Trp
1               5

<210> SEQ ID NO 188
<211> LENGTH: 10
<212> TYPE: PRT
<213> ORGANISM: Artificial Sequence
<220> FEATURE:
<223> OTHER INFORMATION: Synthetic construct

<400> SEQUENCE: 188

Cys Trp Glu Trp Glu Trp Glu Trp Glu Trp
1               5                   10

<210> SEQ ID NO 189
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: X= gamma-carboxyglutamic acid
<220> FEATURE:
<221> NAME/KEY: MOD_RES
<222> LOCATION: (4)..(4)
<223> OTHER INFORMATION: X= gamma-carboxyglutamic acid

<400> SEQUENCE: 189

Trp Xaa Trp Xaa Trp Asp Trp Cys
1               5

<210> SEQ ID NO 190
<211> LENGTH: 8
<212> TYPE: PRT
<213> ORGANISM: Artificial Sequence
<220> FEATURE:
<223> OTHER INFORMATION: Synthetic construct

<400> SEQUENCE: 190

Glu Trp Glu Trp Glu Trp Glu Cys
1               5

<210> SEQ ID NO 191
<211> LENGTH: 8
```

```
<212> TYPE: PRT
<213> ORGANISM: Artificial Sequence
<220> FEATURE:
<223> OTHER INFORMATION: Synthetic construct

<400> SEQUENCE: 191

Asp Trp Asp Trp Asp Trp Asp Cys
1               5

<210> SEQ ID NO 192
<211> LENGTH: 12
<212> TYPE: PRT
<213> ORGANISM: Artificial Sequence
<220> FEATURE:
<223> OTHER INFORMATION: Synthetic construct

<400> SEQUENCE: 192

Glu Glu Glu Glu Glu Lys Trp Trp Trp Trp Trp Cys
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Synthetic construct

<400> SEQUENCE: 193

Glu Glu Glu Glu Lys Trp Trp Trp Trp Trp Cys
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Synthetic construct

<400> SEQUENCE: 194

Glu Glu Glu Glu Glu Lys Trp Trp Trp Trp Cys
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Synthetic construct

<400> SEQUENCE: 195

Glu Glu Glu Glu Lys Trp Trp Trp Trp Cys
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic construct

<400> SEQUENCE: 196

Glu Glu Glu Glu Glu Lys Trp Trp Trp Trp Trp
1               5                   10

<210> SEQ ID NO 197
<211> LENGTH: 10
<212> TYPE: PRT
```

<213> ORGANISM: Artificial Sequence
<220> FEATURE:
<223> OTHER INFORMATION: Synthetic construct

<400> SEQUENCE: 197

Glu Glu Glu Glu Lys Trp Trp Trp Trp Trp
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Synthetic construct

<400> SEQUENCE: 198

Glu Glu Glu Glu Glu Lys Trp Trp Trp Trp
1               5                   10

<210> SEQ ID NO 199
<211> LENGTH: 9
<212> TYPE: PRT
<213> ORGANISM: Artificial Sequence
<220> FEATURE:
<223> OTHER INFORMATION: Synthetic construct

<400> SEQUENCE: 199

Glu Glu Glu Glu Lys Trp Trp Trp Trp
1               5

<210> SEQ ID NO 200
<211> LENGTH: 12
<212> TYPE: PRT
<213> ORGANISM: Artificial Sequence
<220> FEATURE:
<223> OTHER INFORMATION: Synthetic construct

<400> SEQUENCE: 200

Asp Asp Asp Asp Asp Lys Trp Trp Trp Trp Trp Cys
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Synthetic construct

<400> SEQUENCE: 201

Asp Asp Asp Asp Lys Trp Trp Trp Trp Trp Cys
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Synthetic construct

<400> SEQUENCE: 202

Asp Asp Asp Asp Asp Lys Trp Trp Trp Trp Cys
1               5                   10

<210> SEQ ID NO 203
<211> LENGTH: 10
<212> TYPE: PRT
<213> ORGANISM: Artificial Sequence

```
<220> FEATURE:
<223> OTHER INFORMATION: Synthetic construct

<400> SEQUENCE: 203

Asp Asp Asp Asp Lys Trp Trp Trp Trp Cys
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Synthetic construct

<400> SEQUENCE: 204

Asp Asp Asp Asp Asp Lys Trp Trp Trp Trp Trp
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Synthetic construct

<400> SEQUENCE: 205

Asp Asp Asp Asp Lys Trp Trp Trp Trp Trp
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Synthetic construct

<400> SEQUENCE: 206

Asp Asp Asp Asp Asp Lys Trp Trp Trp Trp
1               5                   10

<210> SEQ ID NO 207
<211> LENGTH: 9
<212> TYPE: PRT
<213> ORGANISM: Artificial Sequence
<220> FEATURE:
<223> OTHER INFORMATION: Synthetic construct

<400> SEQUENCE: 207

Asp Asp Asp Asp Lys Trp Trp Trp Trp
1               5

<210> SEQ ID NO 208
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(5)
<223> OTHER INFORMATION: X=gamma-carboxyglutamic acid

<400> SEQUENCE: 208

Xaa Xaa Xaa Xaa Xaa Lys Trp Trp Trp Trp Trp Cys
1               5                   10

<210> SEQ ID NO 209
```

```
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(4)
<223> OTHER INFORMATION: X=gamma-carboxyglutamic acid

<400> SEQUENCE: 209

Xaa Xaa Xaa Xaa Lys Trp Trp Trp Trp Trp Cys
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(5)
<223> OTHER INFORMATION: X=gamma-carboxyglutamic acid

<400> SEQUENCE: 210

Xaa Xaa Xaa Xaa Xaa Lys Trp Trp Trp Trp Cys
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(4)
<223> OTHER INFORMATION: X=gamma-carboxyglutamic acid

<400> SEQUENCE: 211

Xaa Xaa Xaa Xaa Lys Trp Trp Trp Trp Cys
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(5)
<223> OTHER INFORMATION: X=gamma-carboxyglutamic acid

<400> SEQUENCE: 212

Xaa Xaa Xaa Xaa Xaa Lys Trp Trp Trp Trp Trp
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(4)
<223> OTHER INFORMATION: X=gamma-carboxyglutamic acid

<400> SEQUENCE: 213
```

```
Xaa Xaa Xaa Xaa Lys Trp Trp Trp Trp Trp
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(5)
<223> OTHER INFORMATION: X=gamma-carboxyglutamic acid

<400> SEQUENCE: 214

Xaa Xaa Xaa Xaa Xaa Lys Trp Trp Trp Trp
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(4)
<223> OTHER INFORMATION: X=gamma-carboxyglutamic acid

<400> SEQUENCE: 215

Xaa Xaa Xaa Xaa Lys Trp Trp Trp Trp
1               5

<210> SEQ ID NO 216
<211> LENGTH: 11
<212> TYPE: PRT
<213> ORGANISM: Artificial Sequence
<220> FEATURE:
<223> OTHER INFORMATION: Synthetic construct

<400> SEQUENCE: 216

Glu Glu Glu Glu Glu Trp Trp Trp Trp Trp Cys
1               5                   10

<210> SEQ ID NO 217
<211> LENGTH: 9
<212> TYPE: PRT
<213> ORGANISM: Artificial Sequence
<220> FEATURE:
<223> OTHER INFORMATION: Synthetic construct

<400> SEQUENCE: 217

Glu Glu Glu Glu Trp Trp Trp Trp Cys
1               5

<210> SEQ ID NO 218
<211> LENGTH: 10
<212> TYPE: PRT
<213> ORGANISM: Artificial Sequence
<220> FEATURE:
<223> OTHER INFORMATION: Synthetic construct

<400> SEQUENCE: 218

Trp Glu Trp Glu Trp Glu Trp Glu Cys Trp
1               5                   10

<210> SEQ ID NO 219
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 219

Arg Arg Arg Arg Trp Trp Trp Trp Trp Cys
1               5                   10

<210> SEQ ID NO 220
<211> LENGTH: 6
<212> TYPE: PRT
<213> ORGANISM: Artificial Sequence
<220> FEATURE:
<223> OTHER INFORMATION: Synthetic construct

<400> SEQUENCE: 220

Trp Trp Trp Trp Trp Cys
1               5

<210> SEQ ID NO 221
<211> LENGTH: 5
<212> TYPE: PRT
<213> ORGANISM: Artificial Sequence
<220> FEATURE:
<223> OTHER INFORMATION: Synthetic construct

<400> SEQUENCE: 221

Trp Trp Trp Trp Cys
1               5

<210> SEQ ID NO 222
<211> LENGTH: 5
<212> TYPE: PRT
<213> ORGANISM: Artificial Sequence
<220> FEATURE:
<223> OTHER INFORMATION: Synthetic construct

<400> SEQUENCE: 222

Trp Trp Trp Trp Trp
1               5

<210> SEQ ID NO 223
<211> LENGTH: 4
<212> TYPE: PRT
<213> ORGANISM: Artificial Sequence
<220> FEATURE:
<223> OTHER INFORMATION: Synthetic construct

<400> SEQUENCE: 223

Trp Trp Trp Trp
1

<210> SEQ ID NO 224
<211> LENGTH: 10
<212> TYPE: PRT
<213> ORGANISM: Artificial Sequence
<220> FEATURE:
<223> OTHER INFORMATION: Synthetic construct

<400> SEQUENCE: 224

Trp Arg Trp Arg Trp Arg Trp Arg Trp Cys
1               5                   10
```